US010934337B2

(12) United States Patent
Zhang et al.

(10) Patent No.: US 10,934,337 B2
(45) Date of Patent: Mar. 2, 2021

(54) ANTI-BCMA CHIMERIC ANTIGEN RECEPTORS

(71) Applicant: Cartesian Therapeutics, Inc., Gaithersburg, MD (US)

(72) Inventors: Yi Zhang, Gaithersburg, MD (US); C. Andrew Stewart, Frederick, MD (US); Metin Kurtoglu, Bethesda, MD (US); Murat V. Kalayoglu, Silver Spring, MD (US); Michael S. Singer, Chestnut Hill, MA (US)

(73) Assignee: Cartesian Therapeutics, Inc., Gaithersburg, MD (US)

( * ) Notice: Subject to any disclaimer, the term of this patent is extended or adjusted under 35 U.S.C. 154(b) by 0 days.

(21) Appl. No.: 16/825,996

(22) Filed: Mar. 20, 2020

(65) Prior Publication Data

US 2020/0291087 A1  Sep. 17, 2020

Related U.S. Application Data

(63) Continuation of application No. PCT/US2020/022671, filed on Mar. 13, 2020.

(60) Provisional application No. 62/819,068, filed on Mar. 15, 2019.

(51) Int. Cl.
| | |
|---|---|
| *C07K 16/28* | (2006.01) |
| *C07K 16/30* | (2006.01) |
| *C07K 14/705* | (2006.01) |
| *A61K 39/395* | (2006.01) |
| *A61K 39/00* | (2006.01) |

(52) U.S. Cl.
CPC .... *C07K 14/70517* (2013.01); *A61K 39/3955* (2013.01); *A61K 39/39558* (2013.01); *C07K 16/2878* (2013.01); *C07K 16/2896* (2013.01); *C07K 16/30* (2013.01); *A61K 2039/505* (2013.01); *C07K 2317/24* (2013.01); *C07K 2317/53* (2013.01); *C07K 2317/565* (2013.01); *C07K 2317/622* (2013.01); *C07K 2317/73* (2013.01); *C07K 2317/76* (2013.01); *C07K 2319/03* (2013.01)

(58) Field of Classification Search
CPC .......... A61K 2039/505; A61K 39/0011; A61K 2039/5158; A61K 39/3955; A61K 39/395; A61K 39/001102; A61K 39/001129; A61K 39/001117; C07K 2319/03; C07K 2317/24; C07K 2319/00; C07K 16/2896; C07K 2317/73; C07K 2317/92; C07K 2317/76; C07K 2319/30; C07K 14/70596; C07K 16/2866; C07K 16/28; C07K 16/2878; C07K 14/70578; C07K 14/7151; C07K 2317/56; C07K 14/705
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 5,199,942 A | 4/1993 | Gillis |
| 5,350,674 A | 9/1994 | Boenisch et al. |
| 5,399,346 A | 3/1995 | Anderson et al. |
| 5,413,923 A | 5/1995 | Kucherlapati et al. |
| 5,545,806 A | 8/1996 | Lonberg et al. |
| 5,569,825 A | 10/1996 | Lonberg et al. |
| 5,580,859 A | 12/1996 | Felgner et al. |
| 5,585,362 A | 12/1996 | Wilson et al. |
| 5,589,466 A | 12/1996 | Felgner et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,814,318 A | 9/1998 | Lonberg et al. |
| 5,858,358 A | 1/1999 | June et al. |
| 5,883,223 A | 3/1999 | Gray |
| 5,939,598 A | 8/1999 | Kucherlapati et al. |
| 6,120,766 A | 9/2000 | Hale et al. |
| 6,326,193 B1 | 12/2001 | Liu et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |

(Continued)

FOREIGN PATENT DOCUMENTS

| | | |
|---|---|---|
| WO | WO 90/05144 A1 | 5/1990 |
| WO | WO 91/10741 A1 | 7/1991 |

(Continued)

OTHER PUBLICATIONS

Casset al. A peptide mimetic of an anti-CD4 monoclonal antibody by rational design. Biochem Biophys Res Comm 307: 198-205, 2003.*

(Continued)

*Primary Examiner* — Bridget E Bunner

(74) *Attorney, Agent, or Firm* — Wolf, Greenfield & Sacks, P.C.

(57) ABSTRACT

Provided herein are chimeric antigen receptors (CARs), such as those specific for BCMA, that have improved properties, including increased CAR T cell binding to BCMA and improved CAR T cell killing of BCMA-expressing cancer cells. Use of the CARs in immune cells (e.g., T cells), compositions (e.g., CARs and nucleic acid constructs encoding the same), and methods are also contemplated.

30 Claims, 3 Drawing Sheets

Specification includes a Sequence Listing.

(56) References Cited

U.S. PATENT DOCUMENTS

| | | |
|---|---|---|
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 9,765,342 B2 | 9/2017 | Kochenderfer |
| 10,174,095 B2 | 1/2019 | Brogdon et al. |
| 2004/0101519 A1 | 5/2004 | June et al. |
| 2005/0100543 A1 | 5/2005 | Hansen et al. |
| 2005/0113564 A1 | 5/2005 | Campana et al. |
| 2005/0175606 A1 | 8/2005 | Huang et al. |
| 2006/0034810 A1 | 2/2006 | Riley et al. |
| 2006/0121005 A1 | 6/2006 | Berenson et al. |
| 2007/0014794 A1 | 1/2007 | Carter et al. |
| 2014/0287509 A1 | 9/2014 | Sharei et al. |
| 2015/0051266 A1 | 2/2015 | Kochenderfer et al. |
| 2017/0226216 A1 | 8/2017 | Morgan et al. |

FOREIGN PATENT DOCUMENTS

| | | | |
|---|---|---|---|
| WO | WO 96/33735 A1 | 10/1996 | |
| WO | WO 96/34096 A1 | 10/1996 | |
| WO | WO 98/16654 A1 | 4/1998 | |
| WO | WO 98/24893 A2 | 6/1998 | |
| WO | WO 98/46645 A2 | 10/1998 | |
| WO | WO 98/50433 A2 | 11/1998 | |
| WO | WO 2001/029058 A1 | 4/2001 | |
| WO | WO 2001/096584 A2 | 12/2001 | |
| WO | WO 2006/020258 A2 | 2/2006 | |
| WO | WO 2007/024715 A2 | 3/2007 | |
| WO | WO 2014/055771 A1 | 4/2014 | |
| WO | WO-2018237022 A1 | * | 12/2018 |

OTHER PUBLICATIONS

Chen et al. Selection and analysis of an optimized anti-VEGF antibody: crystal structure of an affinity-matured Fab in complex with antigen. J Mol Biol 293: 865-881, 1999.*

De Pascalis et al. Grafting and "abbreviated" complementarity-determining regions containing specificity-determining residues essential for ligand contact to engineer a less immunogenic humanized monoclonal antibody. J Immunol 169: 3076-3084, 2002.*

Dotti et al. Design and development of therapies using chimeric angigen receptor-expressing T cells. Immunol Rev 257: 107-126, 2014.*

Han et al. Chimeric antigen receptor-engineered T cells for cancer immunotherapy: progress and challenges. J Hematol Oncol 6: 47, 2013 (7 total pages).*

Holm et al. Functional mapping and single chain construction of the anti-cytokeratin 8 monoclonal antibody TS1. Mol Immunol 44: 1075-1084, 2007.*

Lloyd et al. Modelling the human immune response: performance of a 10×11 human antibody repertoire against a broad panel of therapeutically relevant antigens. Protein Engineer Design Selection 22(3): 159-168, 2009.*

MacCallum et al. Antibody-antigen interactions: contact analysis and binding site topography. J Mol Biol 262: 732-745, 1996.*

Paul, William E., Fundamental Immunology, 3rd Edition, Raven Press, New York, Chapt. 8, pp. 292-295 (1993).*

Rudikoff et al. Single amino acid substitution altering antigen-binding specificity. Proc Natl Acad Sci USA 79: 1979-1983, 1982.*

Vajdos et al. Comprehensive functional maps of the antigen-binding site of an anti-ErbB2 antibody obtained with shotgun scanning mutagenesis. J Mol Biol 320: 415-428, 2002.*

Invitation to Pay Additional Fees for PCT/US2020/022671, dated Jun. 4, 2020.

Ali et al. T cells expressing an anti-B-cell maturation antigen chimeric antigen receptor cause remissions of multiple myeloma. Blood. 2016;128(13):1688-1700. doi:10.1182/blood-2016-04-711903.

Altschul et al. Gapped BLAST and PSI-Blast: a new generation of protein database search programs. Nucleic Acids Res. 1997;25(17):3389-3402. doi:10.1093/nar/25.17.3389.

Altschul et al., Basic local alignment search tool. J Mol Biol. 1990;215(3):403-410. doi:10.1016/S0022-2836(05)80360-2.

Bierer et al., Cyclosporin A and FK506: molecular mechanisms of immunosuppression and probes for transplantation biology. Curr Opin Immunol. 1993;5(5):763-773. doi:10.1016/0952-7915(93)90135-f.

Bird et al. Single-chain antigen-binding proteins [published correction appears in Science Apr. 28, 1989;244(4903):409]. Science. 1988;242(4877):423-426. doi:10.1126/science.3140379.

Chothia et al., Structural repertoire of the human VH segments. J Mol Biol. 1992;227(3):799-817. doi:10.1016/0022-2836(92)90224-8.

Cougot et al., 'Cap-tabolism'. Trends Biochem Sci. 2004;29(8):436-444. doi:10.1016/j.tibs.2004.06.008.

Elango et al., Optimized transfection of mRNA transcribed from a d(A/T)100 tail-containing vector. Biochem Biophys Res Commun. 2005;330(3):958-966. doi:10.1016/j.bbrc.2005.03.067.

Ertl et al. Considerations for the clinical application of chimeric antigen receptor T cells: observations from a recombinant DNA Advisory Committee Symposium held Jun. 15, 2010 [published correction appears in Cancer Res. Jun. 15, 2011;71(12):4325]. Cancer Res. 2011;71(9):3175-3181. doi:10.1158/0008-5472.CAN-10-4035.

Eshhar et al., Specific activation and targeting of cytotoxic lymphocytes through chimeric single chains consisting of antibody-binding domains and the gamma or zeta subunits of the immunoglobulin and T-cell receptors. Proc Natl Acad Sci U S A. 1993;90(2):720-724. doi:10.1073/pnas.90.2.720.

Garland et al., The use of Teflon cell culture bags to expand functionally active CD8+ cytotoxic T lymphocytes. J Immunol Methods. 1999;227(1-2):53-63. doi:10.1016/s0022-1759(99)00068-x.

Haanen et al., Selective expansion of cross-reactive CD8(+) memory T cells by viral variants. J Exp Med. 1999;190(9):1319-1328. doi:10.1084/jem.190.9.1319.

Henderson et al., Comparison of the effects of FK-506, cyclosporin A and rapamycin on IL-2 production. Immunology. 1991;73(3):316-321.

Holliger et al., "Diabodies": small bivalent and bispecific antibody fragments. Proc Natl Acad Sci U S A. 1993;90(14):6444-6448. doi:10.1073/pnas.90.14.6444.

Huston et al., Protein engineering of antibody binding sites: recovery of specific activity in an anti-digoxin single-chain Fv analogue produced in *Escherichia coli*. Proc Natl Acad Sci U S A. 1988;85(16):5879-5883. doi:10.1073/pnas.85.16.5879.

Karlin et al., Applications and statistics for multiple high-scoring segments in molecular sequences. Proc Natl Acad Sci U S A. 1993;90(12):5873-5877. doi:10.1073/pnas.90.12.5873.

Karlin et al., Methods for assessing the statistical significance of molecular sequence features by using general scoring schemes. Proc Natl Acad Sci U S A. 1990;87(6):2264-2268. doi:10.1073/pnas.87.6.2264.

Lanzavecchia et al., the use of hybrid hybridomas to target human cytotoxic T lymphocytes. Eur J Immunol. 1987;17(1):105-111. doi:10.1002/eji.1830170118.

Lazar et al., A molecular immunology approach to antibody humanization and functional optimization. Mol Immunol. 2007;44(8):1986-1998. doi:10.1016/j.molimm.2006.09.029.

Lefranc et al. IMGT®, the international ImMunoGeneTics information system® 25 years on. Nucleic Acids Res. 2015;43(Database issue):D413-D422. doi:10.1093/nar/gku1056.

Liu et al., Calcineurin is a common target of cyclophilin-cyclosporin A and FKBP-FK506 complexes. Cell. 1991;66(4):807-815. doi:10.1016/0092-8674(91)90124-h.

Mumtaz et al., Design of liposomes for circumventing the reticuloendothelial cells. Glycobiology. 1991;1(5):505-510. doi:10.1093/glycob/1.5.505.

Nishikawa et al., Nonviral vectors in the new millennium: delivery barriers in gene transfer. Hum Gene Ther. 2001;12(8):861-870. doi:10.1089/104303401750195836.

(56) References Cited

OTHER PUBLICATIONS

Poljak, Production and structure of diabodies. Structure. 1994;2(12):1121-1123. doi:10.1016/s0969-2126(94)00113-8.

Rosenberg et al. Use of tumor-infiltrating lymphocytes and interleukin-2 in the immunotherapy of patients with metastatic melanoma. A preliminary report. N Engl J Med. 1988;319(25):1676-1680. doi:10.1056/NEJM198812223192527.

Sadelain et al., The basic principles of chimeric antigen receptor design. Cancer Discov. 2013;3(4):388-398. doi:10.1158/2159-8290.CD-12-0548.

Sadelain et al.,The promise and potential pitfalls of chimeric antigen receptors. Curr Opin Immunol. 2009;21(2):215-223. doi:10.1016/j.coi.2009.02.009.

Song et al., CD27 costimulation augments the survival and antitumor activity of redirected human T cells in vivo. Blood. 2012;119(3):696-706. doi:10.1182/blood-2011-03-344275.

Spiess et al., Alternative molecular formats and therapeutic applications for bispecific antibodies. Mol Immunol. 2015;67(2 Pt A):95-106. doi:10.1016/j.molimm.2015.01.003.

Stepinski et al., Synthesis and properties of mRNAs containing the novel "anti-reverse" cap analogs 7-methyl(3'-O-methyl)GpppG and 7-methyl (3'-deoxy)GpppG. RNA. 2001;7(10):1486-1495.

Ten Berge et al., Selective expansion of a peripheral blood CD8+ memory T cell subset expressing both granzyme B and L-selectin during primary viral infection in renal allograft recipients. Transplant Proc. 1998;30(8):3975-3977. doi:10.1016/s0041-1345(98)01309-8.

Tomlinson et al., The structural repertoire of the human V kappa domain. Embo J. 1995;14(18):4628-4638.

Ui-Tei et al., Sensitive assay of RNA interference in *Drosophila* and Chinese hamster cultured cells using firefly luciferase gene as target. FEBS Lett. 2000;479(3):79-82. doi:10.1016/s0014-5793(00)01883-4.

Ward et al., Binding activities of a repertoire of single immunoglobulin variable domains secreted from *Escherichia coli*. Nature. 1989;341(6242):544-546. doi:10.1038/341544a0.

Watanabe et al. Fine-tuning the CAR spacer improves T-cell potency. Oncoimmunology. 2016;5(12):e1253656. Published Nov. 8, 2016. doi:10.1080/2162402X.2016.1253656.

\* cited by examiner

SEQUENCE LISTING

```
<160> NUMBER OF SEQ ID NOS: 133

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 1

Asp Tyr Ser Ile Asn
```

-continued

```
<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 2

Ser Tyr Ser Ile Asn
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 3

Ser Tyr Asp Ile Asn
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 4

Trp Ile Asn Thr Glu Thr Arg Glu Pro Ala Tyr Ala Tyr Asp Phe Arg
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 5

Trp Ile Asn Thr Asn Thr Gly Asn Pro Thr Tyr Ala Gln Gly Phe Thr
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 6

Trp Ile Asn Thr Glu Thr Arg Glu Pro Ala Tyr Ala Gln Gly Phe Thr
1               5                   10                  15

Gly

<210> SEQ ID NO 7
<211> LENGTH: 8
<212> TYPE: PRT
<213> ORGANISM: Artificial Sequence
<220> FEATURE:
```

<223> OTHER INFORMATION: Synthetic Polypeptide

<400> SEQUENCE: 7

Asp Tyr Ser Tyr Ala Met Asp Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 8

Asp Tyr Thr Tyr Gly Met Asp Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 9

Asp Tyr Leu Tyr Ser Leu Asp Phe
1               5

<210> SEQ ID NO 10
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 10

Arg Ala Ser Glu Ser Val Thr Ile Leu Gly Ser His Leu Ile His
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 11

Arg Ala Ser Glu Ser Val Ser Phe Leu Gly Ile Asn Leu Ile His
1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 12

Gln Leu Ala Ser Asn Val Gln Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 13

Tyr Leu Ala Ser Asn Leu Glu Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 14

Tyr Ser Ala Ser Asn Leu Gln Ser
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 15

Asn Leu Ala Ser Asn Val Asn Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 16

Leu Gln Ser Arg Thr Ile Pro Arg Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 17

Leu Gln Ser Arg Thr Leu Pro Arg Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 18

Leu Gln Ser Lys Asn Phe Pro Arg Thr
1               5

<210> SEQ ID NO 19
<211> LENGTH: 503
<212> TYPE: PRT
<213> ORGANISM: Artificial Sequence
<220> FEATURE:
<223> OTHER INFORMATION: Synthetic Polypeptide

<400> SEQUENCE: 19

```
Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Pro Ser Leu
            20                  25                  30

Ala Met Ser Leu Gly Lys Arg Ala Thr Ile Ser Cys Arg Ala Ser Glu
        35                  40                  45

Ser Val Thr Ile Leu Gly Ser His Leu Ile His Trp Tyr Gln Gln Lys
    50                  55                  60

Pro Gly Gln Pro Pro Thr Leu Leu Ile Gln Leu Ala Ser Asn Val Gln
65                  70                  75                  80

Thr Gly Val Pro Ala Arg Phe Ser Gly Ser Gly Ser Arg Thr Asp Phe
                85                  90                  95

Thr Leu Thr Ile Asp Pro Val Glu Glu Asp Asp Val Ala Val Tyr Tyr
            100                 105                 110

Cys Leu Gln Ser Arg Thr Ile Pro Arg Thr Phe Gly Gly Gly Thr Lys
        115                 120                 125

Leu Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Glu Thr Val Lys Ile Ser Cys Lys Ala Ser Gly
                165                 170                 175

Tyr Thr Phe Thr Asp Tyr Ser Ile Asn Trp Val Lys Arg Ala Pro Gly
            180                 185                 190

Lys Gly Leu Lys Trp Met Gly Trp Ile Asn Thr Glu Thr Arg Glu Pro
        195                 200                 205

Ala Tyr Ala Tyr Asp Phe Arg Gly Arg Phe Ala Phe Ser Leu Glu Thr
    210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
                245                 250                 255

Trp Gly Gln Gly Thr Ser Val Thr Val Ser Ser Phe Val Pro Val Phe
            260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Arg Ser
            340                 345                 350

Lys Arg Ser Arg Leu Leu His Ser Asp Tyr Met Asn Met Thr Pro Arg
        355                 360                 365

Arg Pro Gly Pro Thr Arg Lys His Tyr Gln Pro Tyr Ala Pro Pro Arg
    370                 375                 380

Asp Phe Ala Ala Tyr Arg Ser Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415
```

Leu Gly Arg Arg Glu Glu Tyr Asp Val Leu Asp Lys Arg Gly Arg
            420                 425                 430

Asp Pro Glu Met Gly Gly Lys Pro Arg Arg Lys Asn Pro Gln Glu Gly
            435                 440                 445

Leu Tyr Asn Glu Leu Gln Lys Asp Lys Met Ala Glu Ala Tyr Ser Glu
450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
            500

<210> SEQ ID NO 20
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 20

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
            20                  25                  30

Ala Val Ser Pro Gly Gln Arg Ala Thr Ile Thr Cys Arg Ala Ser Glu
        35                  40                  45

Ser Val Ser Phe Leu Gly Ile Asn Leu Ile His Trp Tyr Gln Gln Lys
    50                  55                  60

Pro Gly Gln Pro Pro Lys Leu Leu Ile Tyr Ser Ala Ser Asn Leu Gln
65                  70                  75                  80

Ser Gly Val Pro Ala Arg Phe Ser Gly Ser Gly Ser Gly Thr Asp Phe
                85                  90                  95

Thr Leu Thr Ile Ser Ser Val Glu Pro Glu Asp Thr Ala Asn Tyr Tyr
            100                 105                 110

Cys Leu Gln Ser Arg Thr Leu Pro Arg Thr Phe Gly Gln Gly Thr Lys
        115                 120                 125

Val Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Gly Ser Val Lys Ile Ser Cys Lys Ala Ser Gly
                165                 170                 175

Tyr Thr Phe Thr Ser Tyr Ser Ile Asn Trp Val Arg Gln Ala Pro Gly
            180                 185                 190

Lys Gly Leu Glu Trp Val Gly Trp Ile Asn Thr Glu Thr Arg Glu Pro
        195                 200                 205

Ala Tyr Ala Gln Gly Phe Thr Gly Arg Phe Thr Phe Ser Ala Asp Thr
    210                 215                 220

Ser Lys Ser Met Ala Tyr Leu Gln Ile Asn Ser Leu Arg Ala Glu Asp
225                 230                 235                 240

Thr Ala Val Tyr Tyr Cys Ala Leu Asp Tyr Leu Tyr Ser Leu Asp Phe
                245                 250                 255

Trp Gly Gln Gly Thr Leu Val Thr Val Ser Ser Phe Val Pro Val Phe
            260                 265                 270

```
Leu Pro Ala Lys Pro Thr Thr Pro Ala Pro Arg Pro Pro Thr Pro
        275                 280                 285

Ala Pro Thr Ile Ala Ser Gln Pro Leu Ser Leu Arg Pro Glu Ala Cys
290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Arg Val
                340                 345                 350

Lys Phe Ser Arg Ser Ala Asp Ala Pro Ala Tyr Gln Gln Gly Gln Asn
                355                 360                 365

Gln Leu Tyr Asn Glu Leu Asn Leu Gly Arg Arg Glu Glu Tyr Asp Val
            370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
                420                 425                 430

Gly Lys Gly His Asp Gly Leu Tyr Gln Gly Leu Ser Thr Ala Thr Lys
                435                 440                 445

Asp Thr Tyr Asp Ala Leu His Met Gln Ala Leu Pro Pro Arg
            450                 455                 460

<210> SEQ ID NO 21
<211> LENGTH: 504
<212> TYPE: PRT
<213> ORGANISM: Artificial Sequence
<220> FEATURE:
<223> OTHER INFORMATION: Synthetic Polypeptide

<400> SEQUENCE: 21

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
                20                  25                  30

Ala Val Ser Pro Gly Gln Arg Ala Thr Ile Thr Cys Arg Ala Ser Glu
            35                  40                  45

Ser Val Ser Phe Leu Gly Ile Asn Leu Ile His Trp Tyr Gln Gln Lys
        50                  55                  60

Pro Gly Gln Pro Pro Lys Leu Leu Ile Tyr Ser Ala Ser Asn Leu Gln
65                  70                  75                  80

Ser Gly Val Pro Ala Arg Phe Ser Gly Ser Gly Ser Gly Thr Asp Phe
                85                  90                  95

Thr Leu Thr Ile Ser Ser Val Glu Pro Glu Asp Thr Ala Asn Tyr Tyr
            100                 105                 110

Cys Leu Gln Ser Arg Thr Leu Pro Arg Thr Phe Gly Gln Gly Thr Lys
        115                 120                 125

Val Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Gly Ser Val Lys Ile Ser Cys Lys Ala Ser Gly
                165                 170                 175
```

Tyr Thr Phe Thr Ser Tyr Ser Ile Asn Trp Val Arg Gln Ala Pro Gly
            180                 185                 190

Lys Gly Leu Glu Trp Val Gly Trp Ile Asn Thr Glu Thr Arg Glu Pro
            195                 200                 205

Ala Tyr Ala Gln Gly Phe Thr Gly Arg Phe Thr Phe Ser Ala Asp Thr
            210                 215                 220

Ser Lys Ser Met Ala Tyr Leu Gln Ile Asn Ser Leu Arg Ala Glu Asp
225                 230                 235                 240

Thr Ala Val Tyr Tyr Cys Ala Leu Asp Tyr Leu Tyr Ser Leu Asp Phe
                245                 250                 255

Trp Gly Gln Gly Thr Leu Val Thr Val Ser Ser Phe Val Pro Val Phe
            260                 265                 270

Leu Pro Ala Lys Pro Thr Thr Thr Pro Ala Pro Arg Pro Pro Thr Pro
            275                 280                 285

Ala Pro Thr Ile Ala Ser Gln Pro Leu Ser Leu Arg Pro Glu Ala Cys
            290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Lys Arg
            340                 345                 350

Gly Arg Lys Lys Leu Leu Tyr Ile Phe Lys Gln Pro Phe Met Arg Pro
            355                 360                 365

Val Gln Thr Thr Gln Glu Glu Asp Gly Cys Ser Cys Arg Phe Pro Glu
            370                 375                 380

Glu Glu Glu Gly Gly Cys Glu Leu Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
            435                 440                 445

Gly Leu Tyr Asn Glu Leu Gln Lys Asp Lys Met Ala Glu Ala Tyr Ser
            450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500

<210> SEQ ID NO 22
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 22

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
            20                  25                  30

```
Ala Val Ser Pro Gly Gln Arg Ala Thr Ile Thr Cys Arg Ala Ser Glu
         35                   40                  45

Ser Val Ser Phe Leu Gly Ile Asn Leu Ile His Trp Tyr Gln Gln Lys
50                  55                  60

Pro Gly Gln Pro Pro Lys Leu Leu Ile Tyr Ser Ala Ser Asn Leu Gln
65                  70                  75                  80

Ser Gly Val Pro Ala Arg Phe Ser Gly Ser Gly Ser Gly Thr Asp Phe
                 85                  90                  95

Thr Leu Thr Ile Ser Ser Val Glu Pro Glu Asp Thr Ala Asn Tyr Tyr
             100                 105                 110

Cys Leu Gln Ser Lys Asn Phe Pro Arg Thr Phe Gly Gln Gly Thr Lys
             115                 120                 125

Val Glu Ile Lys Gly Ser Thr Ser Gly Ser Gly Lys Pro Gly Ser Gly
130                 135                 140

Glu Gly Ser Thr Lys Gly Gln Ile Gln Leu Val Gln Ser Gly Pro Glu
145                 150                 155                 160

Leu Lys Lys Pro Gly Ser Val Lys Ile Ser Cys Lys Ala Ser Gly
                 165                 170                 175

Tyr Thr Phe Thr Ser Tyr Ser Ile Asn Trp Val Arg Gln Ala Pro Gly
             180                 185                 190

Lys Gly Leu Glu Trp Val Gly Trp Ile Asn Thr Glu Thr Arg Glu Pro
             195                 200                 205

Ala Tyr Ala Gln Gly Phe Thr Gly Arg Phe Thr Phe Ser Ala Asp Thr
210                 215                 220

Ser Lys Ser Met Ala Tyr Leu Gln Ile Asn Ser Leu Arg Ala Glu Asp
225                 230                 235                 240

Thr Ala Val Tyr Tyr Cys Ala Leu Asp Tyr Leu Tyr Ser Leu Asp Phe
                 245                 250                 255

Trp Gly Gln Gly Thr Leu Val Thr Val Ser Ser Phe Val Pro Val Phe
             260                 265                 270

Leu Pro Ala Lys Pro Thr Thr Thr Pro Ala Pro Arg Pro Pro Thr Pro
             275                 280                 285

Ala Pro Thr Ile Ala Ser Gln Pro Leu Ser Leu Arg Pro Glu Ala Cys
             290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                 325                 330                 335

Leu Leu Ser Leu Val Ile Thr Leu Tyr Cys Asn His Arg Asn Arg Val
             340                 345                 350

Lys Phe Ser Arg Ser Ala Asp Ala Pro Ala Tyr Gln Gln Gly Gln Asn
             355                 360                 365

Gln Leu Tyr Asn Glu Leu Asn Leu Gly Arg Arg Glu Glu Tyr Asp Val
370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                 405                 410                 415

Met Ala Glu Ala Tyr Ser Glu Ile Gly Met Lys Gly Glu Arg Arg Arg
             420                 425                 430

Gly Lys Gly His Asp Gly Leu Tyr Gln Gly Leu Ser Thr Ala Thr Lys
             435                 440                 445
```

```
Asp Thr Tyr Asp Ala Leu His Met Gln Ala Leu Pro Pro Arg
    450                 455                 460
```

<210> SEQ ID NO 23
<211> LENGTH: 504
<212> TYPE: PRT
<213> ORGANISM: Artificial Sequence
<220> FEATURE:
<223> OTHER INFORMATION: Synthetic Polypeptide

<400> SEQUENCE: 23

```
Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
            20                  25                  30

Ala Val Ser Pro Gly Gln Arg Ala Thr Ile Thr Cys Arg Ala Ser Glu
        35                  40                  45

Ser Val Ser Phe Leu Gly Ile Asn Leu Ile His Trp Tyr Gln Gln Lys
    50                  55                  60

Pro Gly Gln Pro Pro Lys Leu Leu Ile Tyr Ser Ala Ser Asn Leu Gln
65                  70                  75                  80

Ser Gly Val Pro Ala Arg Phe Ser Gly Ser Gly Ser Gly Thr Asp Phe
                85                  90                  95

Thr Leu Thr Ile Ser Ser Val Glu Pro Glu Asp Thr Ala Asn Tyr Tyr
            100                 105                 110

Cys Leu Gln Ser Lys Asn Phe Pro Arg Thr Phe Gly Gln Gly Thr Lys
        115                 120                 125

Val Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Gly Ser Val Lys Ile Ser Cys Lys Ala Ser Gly
                165                 170                 175

Tyr Thr Phe Thr Ser Tyr Ser Ile Asn Trp Val Arg Gln Ala Pro Gly
            180                 185                 190

Lys Gly Leu Glu Trp Val Gly Trp Ile Asn Thr Glu Thr Arg Glu Pro
        195                 200                 205

Ala Tyr Ala Gln Gly Phe Thr Gly Arg Phe Thr Phe Ser Ala Asp Thr
    210                 215                 220

Ser Lys Ser Met Ala Tyr Leu Gln Ile Asn Ser Leu Arg Ala Glu Asp
225                 230                 235                 240

Thr Ala Val Tyr Tyr Cys Ala Leu Asp Tyr Leu Tyr Ser Leu Asp Phe
                245                 250                 255

Trp Gly Gln Gly Thr Leu Val Thr Val Ser Ser Phe Val Pro Val Phe
            260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Lys Arg
            340                 345                 350
```

Gly Arg Lys Lys Leu Leu Tyr Ile Phe Lys Gln Pro Phe Met Arg Pro
            355                 360                 365

Val Gln Thr Thr Gln Glu Glu Asp Gly Cys Ser Cys Arg Phe Pro Glu
    370                 375                 380

Glu Glu Glu Gly Gly Cys Glu Leu Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500

<210> SEQ ID NO 24
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 24

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
            20                  25                  30

Ala Val Ser Pro Gly Gln Arg Ala Thr Ile Thr Cys Arg Ala Ser Glu
        35                  40                  45

Ser Val Thr Ile Leu Gly Ser His Leu Ile His Trp Tyr Gln Gln Lys
    50                  55                  60

Pro Gly Gln Pro Pro Lys Leu Leu Ile Asn Leu Ala Ser Asn Val Asn
65                  70                  75                  80

Thr Gly Val Pro Ala Arg Phe Ser Gly Ser Gly Ser Gly Thr Asp Phe
                85                  90                  95

Thr Leu Thr Ile Ser Ser Val Glu Pro Glu Asp Thr Ala Asn Tyr Tyr
            100                 105                 110

Cys Leu Gln Ser Arg Thr Leu Pro Arg Thr Phe Gly Gln Gly Thr Lys
        115                 120                 125

Val Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Gly Ser Val Lys Ile Ser Cys Lys Ala Ser Gly
                165                 170                 175

Tyr Thr Phe Thr Asp Tyr Ser Ile Asn Trp Val Arg Gln Ala Pro Gly
            180                 185                 190

Lys Gly Leu Glu Trp Val Gly Trp Ile Asn Thr Glu Thr Arg Glu Pro
        195                 200                 205

Ala Tyr Ala Tyr Asp Phe Thr Gly Arg Phe Thr Phe Ser Ala Asp Thr
            210                 215                 220

Ser Lys Ser Met Ala Tyr Leu Gln Ile Asn Ser Leu Arg Ala Glu Asp
225                 230                 235                 240

Thr Ala Val Tyr Tyr Cys Ala Leu Asp Tyr Thr Tyr Gly Met Asp Tyr
                245                 250                 255

Trp Gly Gln Gly Thr Leu Val Thr Val Ser Ser Phe Val Pro Val Phe
            260                 265                 270

Leu Pro Ala Lys Pro Thr Thr Thr Pro Ala Pro Arg Pro Pro Thr Pro
            275                 280                 285

Ala Pro Thr Ile Ala Ser Gln Pro Leu Ser Leu Arg Pro Glu Ala Cys
            290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Arg Val
            340                 345                 350

Lys Phe Ser Arg Ser Ala Asp Ala Pro Ala Tyr Gln Gln Gly Gln Asn
            355                 360                 365

Gln Leu Tyr Asn Glu Leu Asn Leu Gly Arg Arg Glu Glu Tyr Asp Val
            370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
            435                 440                 445

Asp Thr Tyr Asp Ala Leu His Met Gln Ala Leu Pro Pro Arg
            450                 455                 460

<210> SEQ ID NO 25
<211> LENGTH: 504
<212> TYPE: PRT
<213> ORGANISM: Artificial Sequence
<220> FEATURE:
<223> OTHER INFORMATION: Synthetic Polypeptide

<400> SEQUENCE: 25

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
            20                  25                  30

Ala Val Ser Pro Gly Gln Arg Ala Thr Ile Thr Cys Arg Ala Ser Glu
        35                  40                  45

Ser Val Thr Ile Leu Gly Ser His Leu Ile His Trp Tyr Gln Gln Lys
    50                  55                  60

Pro Gly Gln Pro Pro Lys Leu Leu Ile Asn Leu Ala Ser Asn Val Asn
65                  70                  75                  80

Thr Gly Val Pro Ala Arg Phe Ser Gly Ser Gly Ser Gly Thr Asp Phe
                85                  90                  95

Thr Leu Thr Ile Ser Ser Val Glu Pro Glu Asp Thr Ala Asn Tyr Tyr
            100                 105                 110

Cys Leu Gln Ser Arg Thr Leu Pro Arg Thr Phe Gly Gln Gly Thr Lys
            115                 120                 125

Val Glu Ile Lys Gly Ser Thr Gly Ser Gly Lys Pro Gly Ser Gly
130                 135                 140

Glu Gly Ser Thr Lys Gly Gln Ile Gln Leu Val Gln Ser Gly Pro Glu
145                 150                 155                 160

Leu Lys Lys Pro Gly Gly Ser Val Lys Ile Ser Cys Lys Ala Ser Gly
                165                 170                 175

Tyr Thr Phe Thr Asp Tyr Ser Ile Asn Trp Val Arg Gln Ala Pro Gly
            180                 185                 190

Lys Gly Leu Glu Trp Val Gly Trp Ile Asn Thr Glu Thr Arg Glu Pro
        195                 200                 205

Ala Tyr Ala Tyr Asp Phe Thr Gly Arg Phe Thr Phe Ser Ala Asp Thr
    210                 215                 220

Ser Lys Ser Met Ala Tyr Leu Gln Ile Asn Ser Leu Arg Ala Glu Asp
225                 230                 235                 240

Thr Ala Val Tyr Tyr Cys Ala Leu Asp Tyr Thr Tyr Gly Met Asp Tyr
                245                 250                 255

Trp Gly Gln Gly Thr Leu Val Thr Val Ser Ser Phe Val Pro Val Phe
            260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Lys Arg
            340                 345                 350

Gly Arg Lys Lys Leu Leu Tyr Ile Phe Lys Gln Pro Phe Met Arg Pro
        355                 360                 365

Val Gln Thr Thr Gln Glu Glu Asp Gly Cys Ser Cys Arg Phe Pro Glu
    370                 375                 380

Glu Glu Glu Gly Gly Cys Glu Leu Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500

<210> SEQ ID NO 26
<211> LENGTH: 462
<212> TYPE: PRT

<213> ORGANISM: Artificial Sequence
<220> FEATURE:
<223> OTHER INFORMATION: Synthetic Polypeptide

<400> SEQUENCE: 26

```
Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ser Ser Leu
            20                  25                  30

Ser Ala Ser Val Gly Asp Arg Ala Thr Ile Ser Cys Arg Ala Ser Glu
        35                  40                  45

Ser Val Thr Ile Leu Gly Ser His Leu Ile His Trp Tyr Gln Gln Lys
    50                  55                  60

Pro Gly Gln Ala Pro Lys Leu Leu Ile Gln Leu Ala Ser Asn Val Gln
65                  70                  75                  80

Thr Gly Val Pro Ala Arg Phe Ser Gly Ser Gly Ser Gly Thr Asp Phe
                85                  90                  95

Thr Leu Thr Ile Ser Ser Val Glu Pro Glu Asp Val Ala Val Tyr Tyr
            100                 105                 110

Cys Leu Gln Ser Arg Thr Ile Pro Arg Thr Phe Gly Gln Gly Thr Lys
        115                 120                 125

Val Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Gly Ser Val Lys Ile Ser Cys Ala Ala Ser Gly
                165                 170                 175

Tyr Thr Phe Thr Asp Tyr Ser Ile Asn Trp Val Arg Gln Ala Pro Gly
            180                 185                 190

Lys Gly Leu Glu Trp Val Gly Trp Ile Asn Thr Glu Thr Arg Glu Pro
        195                 200                 205

Ala Tyr Ala Tyr Asp Phe Arg Gly Arg Phe Thr Phe Ser Ala Asp Thr
    210                 215                 220

Ser Lys Ser Thr Ala Tyr Leu Gln Met Asn Ser Leu Arg Ala Glu Asp
225                 230                 235                 240

Thr Ala Val Tyr Tyr Cys Ala Leu Asp Tyr Ser Tyr Ala Met Asp Tyr
                245                 250                 255

Trp Gly Gln Gly Thr Leu Val Thr Val Ser Ser Phe Val Pro Val Phe
            260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
```

```
                385                 390                 395                 400
Arg Lys Asn Pro Gln Glu Gly Leu Tyr Asn Glu Leu Gln Lys Asp Lys
                    405                 410                 415

Met Ala Glu Ala Tyr Ser Glu Ile Gly Met Lys Gly Glu Arg Arg Arg
                    420                 425                 430

Gly Lys Gly His Asp Gly Leu Tyr Gln Gly Leu Ser Thr Ala Thr Lys
                    435                 440                 445

Asp Thr Tyr Asp Ala Leu His Met Gln Ala Leu Pro Pro Arg
                    450                 455                 460

<210> SEQ ID NO 27
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 27

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ser Ser Leu
                20                  25                  30

Ser Ala Ser Val Gly Asp Arg Ala Thr Ile Ser Cys Arg Ala Ser Glu
            35                  40                  45

Ser Val Thr Ile Leu Gly Ser His Leu Ile His Trp Tyr Gln Gln Lys
        50                  55                  60

Pro Gly Gln Ala Pro Lys Leu Leu Ile Gln Leu Ala Ser Asn Val Gln
65                  70                  75                  80

Thr Gly Val Pro Ala Arg Phe Ser Gly Ser Gly Ser Gly Thr Asp Phe
                85                  90                  95

Thr Leu Thr Ile Ser Ser Val Glu Pro Glu Asp Val Ala Val Tyr Tyr
            100                 105                 110

Cys Leu Gln Ser Arg Thr Ile Pro Arg Thr Phe Gly Gln Gly Thr Lys
        115                 120                 125

Val Glu Ile Lys Gly Ser Thr Ser Gly Ser Gly Lys Pro Gly Ser Gly
130                 135                 140

Glu Gly Ser Thr Lys Gly Gln Ile Gln Leu Val Gln Ser Gly Pro Glu
145                 150                 155                 160

Leu Lys Lys Pro Gly Ser Val Lys Ile Ser Cys Ala Ala Ser Gly
                165                 170                 175

Tyr Thr Phe Thr Asp Tyr Ser Ile Asn Trp Val Arg Gln Ala Pro Gly
            180                 185                 190

Lys Gly Leu Glu Trp Val Gly Trp Ile Asn Thr Glu Thr Arg Glu Pro
        195                 200                 205

Ala Tyr Ala Tyr Asp Phe Arg Gly Arg Phe Thr Phe Ser Ala Asp Thr
    210                 215                 220

Ser Lys Ser Thr Ala Tyr Leu Gln Met Asn Ser Leu Arg Ala Glu Asp
225                 230                 235                 240

Thr Ala Val Tyr Tyr Cys Ala Leu Asp Tyr Ser Tyr Ala Met Asp Tyr
                245                 250                 255

Trp Gly Gln Gly Thr Leu Val Thr Val Ser Ser Phe Val Pro Val Phe
            260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
```

```
            290                 295                 300
Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Arg Val
                340                 345                 350

Lys Phe Ser Arg Ser Ala Asp Ala Pro Ala Tyr Gln Gln Gly Gln Asn
                355                 360                 365

Gln Leu Tyr Asn Glu Leu Asn Leu Gly Arg Arg Glu Glu Tyr Asp Val
            370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
                420                 425                 430

Gly Lys Gly His Asp Gly Leu Tyr Gln Gly Leu Ser Thr Ala Thr Lys
                435                 440                 445

Asp Thr Tyr Asp Ala Leu His Met Gln Ala Leu Pro Pro Arg
                450                 455                 460

<210> SEQ ID NO 28
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 28

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
                20                  25                  30

Ala Val Ser Pro Gly Gln Arg Ala Thr Ile Thr Cys Arg Ala Ser Glu
            35                  40                  45

Ser Val Thr Ile Leu Gly Ser His Leu Ile His Trp Tyr Gln Gln Lys
50                  55                  60

Pro Gly Gln Pro Pro Lys Leu Leu Ile Gln Leu Ala Ser Asn Val Gln
65                  70                  75                  80

Thr Gly Val Pro Ala Arg Phe Ser Gly Ser Gly Ser Gly Thr Asp Phe
                85                  90                  95

Thr Leu Thr Ile Ser Ser Val Glu Pro Glu Asp Thr Ala Asn Tyr Tyr
                100                 105                 110

Cys Leu Gln Ser Arg Thr Ile Pro Arg Thr Phe Gly Gln Gly Thr Lys
                115                 120                 125

Val Glu Ile Lys Gly Ser Thr Ser Gly Ser Gly Lys Pro Gly Ser Gly
            130                 135                 140

Glu Gly Ser Thr Lys Gly Gln Ile Gln Leu Val Gln Ser Gly Pro Glu
145                 150                 155                 160

Leu Lys Lys Pro Gly Gly Ser Val Lys Ile Ser Cys Lys Ala Ser Gly
                165                 170                 175

Tyr Thr Phe Thr Asp Tyr Ser Ile Asn Trp Val Arg Gln Ala Pro Gly
                180                 185                 190

Lys Gly Leu Glu Trp Val Gly Trp Ile Asn Thr Glu Thr Arg Glu Pro
```

```
                195                 200                 205
Ala Tyr Ala Tyr Asp Phe Thr Gly Arg Phe Thr Phe Ser Ala Asp Thr
    210                 215                 220

Ser Lys Ser Met Ala Tyr Leu Gln Ile Asn Ser Leu Arg Ala Glu Asp
225                 230                 235                 240

Thr Ala Val Tyr Tyr Cys Ala Leu Asp Tyr Ser Tyr Ala Met Asp Tyr
                245                 250                 255

Trp Gly Gln Gly Thr Leu Val Thr Val Ser Ser Phe Val Pro Val Phe
            260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 29
<211> LENGTH: 1753
<212> TYPE: DNA
<213> ORGANISM: Artificial Sequence
<220> FEATURE:
<223> OTHER INFORMATION: Synthetic Polynucleotide

<400> SEQUENCE: 29
aggaaataag agagaaaaga agagtaagaa gaaatataag agccaccatg gccctgcccg      60
tgacagctct gctgctccct ctggctctgc tgctgcacgc tgccagaccc gacatcgtgc     120
tgacacaaag cccccctagc ctggccatga gcctgggcaa gagggccaca atctcctgca     180
gggccagcga gtccgtgacc atcctgggca gccacctgat ccactggtac cagcagaagc     240
ctggccagcc ccctaccctg ctgatccagc tggcctccaa cgtgcagaca ggagtgcccg     300
ctaggttctc cggctccggc agcagaaccg acttcaccct gaccatcgac cccgtcgagg     360
aggacgacgt ggctgtctac tattgcctgc agagcaggac catccccagg accttcggag     420
cgggcacaaa gctggagatc aagggcagca ccagcggctc cggaaagcct ggcagcggag     480
aaggctccac caagggacag attcagctgg tgcagagcgg accagagctg aagaagcccg     540
gcgaaacagt caagatcagc tgcaaagctt ccggctacac cttcacagac tacagcatca     600
```

```
actgggtgaa aagggccccc ggcaagggcc tgaaatggat gggctggatc aacaccgaga      660
ccagggagcc cgcctacgcc tacgacttta ggggcaggtt cgccttcagc ctggagacat      720
ccgctagcac cgcttacctg caaattaata acctgaagta cgaggacacc gccacctatt      780
tttgtgccct ggactacagc tacgcaatgg actattgggg acagggaacc tccgtgaccg      840
tgagcagctt tgtgcccgtg ttcctgcccg ccaaacccac caccacacct gctcctaggc      900
cccctacacc tgcccctacc atcgcttccc agccctgag cctcagacct gaagcctgca       960
gacctgctgc tggaggcgcc gtccacacaa ggggactgga cttcgcctgt gacatctaca     1020
tctgggctcc tctcgccggc acctgtggag tgctgctgct gtccctggtc atcaccctgt     1080
actgcaacca caggaacagg agcaagaggt ccaggctgct gcatagcgac tacatgaaca     1140
tgaccccag aaggcccgga cccaccagga agcactacca gccctacgcc ccccctaggg      1200
attttgctgc ctacaggtcc agagtgaagt tcagcagatc cgctgatgcc cctgcctatc     1260
agcagggcca gaaccaactc tacaacgagc tgaacctggg aaggagggag gagtacgacg     1320
tgctcgacaa gagaagggga agggatcctg aaatgggcgg caagcccagg agaaagaacc     1380
ctcaggaggg cctgtacaac gaactgcaga aggataagat ggccgaggcc tacagcgaaa     1440
tcggcatgaa aggcgagaga aggagaggca agggccacga cggactgtac cagggcctgt     1500
ccaccgccac caaagacacc tacgatgccc tgcacatgca ggccctgccc ccaggtgag      1560
cggccgctta ttaagctgc cttctgcggg gcttgccttc tggccatgcc cttcttctct      1620
cccttgcacc tgtacctctt ggtctttgaa taaagcctga gtaggaagtc tagaaaaaaa     1680
aaaaaaaaaa aaaaaaaaaa aaaaaaaaaa aaaaaaaaaa aaaaaaaaaa aaaaaaaaaa     1740
aaaaaaaaaa aaa                                                        1753

<210> SEQ ID NO 30
<211> LENGTH: 1660
<212> TYPE: DNA
<213> ORGANISM: Artificial Sequence
<220> FEATURE:
<223> OTHER INFORMATION: Synthetic Polynucleotide
<400> SEQUENCE: 30
agacccaagc tggctagctc taaagaagcc cctgggagca cagctcatca ccatggcact       60
gccagtcaca gcactgctgc tgccactggc actgctgctc cacgccgcca gacccgacat      120
cgtgctgaca cagagcccag caagcctggc cgtgagccca ggccagagag ccacaatcac      180
atgcagagcc agcgagtccg tgtccttcct gggcatcaac ctgatccact ggtaccagca      240
gaagcccgga cagccacca aactgctgat ctactccgcc agcaacctgc agtcaggcgt       300
gccagccaga ttcagcggca gcggcagcgg aaccgacttc accctgacaa tcagctcagt      360
ggaaccagaa gacaccgcca actactactg cctgcagagc agaaccctgc cagaaccttt      420
cggccaaggc accaaggtcg aaatcaaggg ctccacaagc ggcagcggaa agcccggaag      480
cggcgaggga agcaccaagg ccagatcca gctggtgcag agcggccccg aactgaagaa      540
acccggcgga agcgtgaaaa tctcctgcaa ggccagcggc tacaccttca cctcctacag      600
catcaactgg gtgcgccagg ccccaggcaa gggcctggaa tgggtcggct ggatcaacac      660
cgagacaaga gagcccgcct acgcccaggg cttcacaggc agattcacct tcagcgcaga      720
cacaagcaag agcatggcct acctgcagat caactccctg agagcagagg acaccgccgt      780
ctactactgc gccctggact acctctactc cctggacttc tggggccagg gcaccctcgt      840
```

```
gaccgtgtcc agcttcgtgc ccgtgttcct gccagccaag ccaaccacaa caccagcacc      900
cagaccacca acaccagcac caacaatcgc cagccagcca ctgtccctga ggccagaggc      960
atgcagacca gcagcaggcg gagccgtgca ccagagga ctggacttcg cctgcgacat       1020
ctacatctgg gcaccactgg ccggaacatg cggcgtgctg ctgctgagcc tggtcatcac     1080
cctgtactgc aaccaccgga acagagtgaa gttcagcaga tccgccgacg caccagccta    1140
ccagcaggga cagaaccagc tgtacaacga gctgaacctg gggagaagag aagagtacga    1200
cgtgctggat aagcggagag cagagaccc tgagatgggc ggcaagccca dacggaagaa     1260
cccacaagag ggcctgtaca cgagctgca gaaagacaag atggccgagg cctacagcga     1320
gatcggaatg aagggcgagc gcagaagagg caagggacac gacggactgt accagggcct    1380
gagcacagcc accaaggata cctacgatgc cctgcacatg caggccctgc accaagatg     1440 actatgaaga aggaaggcat ccagaccaga aaccgaaaaa tgtctagcaa atccaaaaag    1500
tgcaaaaaag tgcatgactc actggaggac ttccccaaga acagtcgtt taacccggcc    1560 gccctctcca gacacatgtc ctccctgagc acatctcgc ccttcagcca ctccagccac    1620
atgctgacca cgcccacgcc gatgcacccg ccatccagca                          1660

<210> SEQ ID NO 31
<211> LENGTH: 1786
<212> TYPE: DNA
<213> ORGANISM: Artificial Sequence
<220> FEATURE:
<223> OTHER INFORMATION: Synthetic Polynucleotide

<400> SEQUENCE: 31
agacccaagc tggctagctc taaagaagcc cctgggagca cagctcatca ccatggcact      60
gccagtcaca gcactgctgc tgccactggc actgctgctc cacgccgcca gacccgacat     120
cgtgctgaca cagagcccag caagcctggc cgtgagccca ggccagagag ccacaatcac     180
atgcagagcc agcgagtccg tgtccttcct gggcatcaac ctgatccact ggtaccagca     240
gaagcccgga cagccacccca aactgctgat ctactccgcc agcaacctgc agtcaggcgt     300
gccagccaga ttcagcggca gcggcagcgg aaccgacttc accctgacaa tcagctcagt     360
ggaaccagaa gacaccgcca actactactg cctgcagagc agaaccctgc cagaaccttt     420
cggccaaggc accaaggtcg aaatcaaggg ctccacaagc ggcagcggaa agcccggaag     480
cggcgaggga agcaccaagg ccagatcca gctggtgcag agcggccccg aactgaagaa     540
acccggcgga agcgtgaaaa tctcctgcaa ggccagcggc tacaccttca cctcctacag     600
catcaactgg gtgcgccagg cccaggcaa gggcctggaa tgggtcggct ggatcaacac     660
cgagacaaga gagcccgcct acgcccaggg cttcacaggc agattcaccct tcagcgcaga     720 cacaagcaag agcatggcct acctgcagat caactccctg agagcagagg acaccgccgt     780
ctactactgc gccctggact accctctactc cctggacttc tggggccagg gcaccctcgt     840
gaccgtgtcc agcttcgtgc ccgtgttcct gccagccaag ccaaccacaa caccagcacc     900
cagaccacca acaccagcac caacaatcgc cagccagcca ctgtccctga ggccagaggc     960
atgcagacca gcagcaggcg gagccgtgca ccagagga ctggacttcg cctgcgacat      1020
ctacatctgg gcaccactgg ccggaacatg cggcgtgctg ctgctgagcc tggtcatcac    1080
cctgtactgc aaccaccgga acaaacgcgg gagaaaaaag ctcctctaca tcttcaagca    1140
accattcatg cgcccagtcc aaaccacaca ggaggaagac ggatgcagct gcaggttccc    1200
cgaagaggag gaaggcggat gcgagctcag agtgaagttc agcagatccg ccgacgcacc    1260
```

```
agcctaccag cagggacaga accagctgta caacgagctg aacctgggga gaagagaaga    1320
gtacgacgtg ctggataagc ggagaggcag agaccctgag atgggcggca agcccagacg    1380
gaagaaccca caagagggcc tgtacaacga gctgcagaaa gacaagatgg ccgaggccta    1440
cagcgagatc ggaatgaagg gcgagcgcag aagaggcaag gacacgacg gactgtacca     1500 gggcctgagc acagccacca aggatacca cgatgccctg cacatgcagg ccctgccacc     1560
aagatgacta tgaagaagga aggcatccag accagaaacc gaaaaatgtc tagcaaatcc    1620
aaaaagtgca aaaagtgca tgactcactg gaggacttcc ccaagaacag ctcgtttaac     1680
ccggccgccc tctccagaca catgtcctcc ctgagccaca tctcgccctt cagccactcc    1740
agccacatgc tgaccacgcc cacgccgatg cacccgccat ccagca                   1786
```

<210> SEQ ID NO 32
<211> LENGTH: 1660
<212> TYPE: DNA
<213> ORGANISM: Artificial Sequence
<220> FEATURE:
<223> OTHER INFORMATION: Synthetic Polynucleotide

<400> SEQUENCE: 32

```
agacccaagc tggctagctc taaagaagcc cctgggagca cagctcatca ccatggcact      60
gccagtcaca gcactgctgc tgccactggc actgctgctc cacgccgcca gacccgacat     120
cgtgctgaca cagagcccag caagcctggc cgtgagccca ggccagagag ccacaatcac     180
atgcagagcc agcgagtccg tgtccttcct gggcatcaac ctgatccact ggtaccagca     240
gaagcccgga cagccacccca aactgctgat ctactccgcc agcaacctgc agtcaggcgt    300
gccagccaga ttcagcggca gcggcagcgg aaccgacttc accctgacaa tcagctcagt    360
ggaaccagaa gacaccgcca actactactg cctgcagagc aagaacttcc ccagaacctt    420
cggccaaggc accaaggtcg aaatcaaggg ctccacaagc ggcagcggaa agcccggaag    480
cggcgaggga agcaccaagg gccagatcca gctggtgcag agcggccccg aactgaagaa    540
acccggcgga agcgtgaaaa tctcctgcaa ggccagcggc tacaccttca cctcctacag    600
catcaactgg gtgcgccagg ccccaggcaa gggcctggaa tgggtcggct ggatcaacac    660
cgagacaaga gagcccgcct acgcccaggg cttcacaggc agattcaccc tcagcgcaga   720
cacaagcaag agcatggcct acctgcagat caactccctg agagcagagg acaccgccgt    780
ctactactgc gccctggact acctctactc cctggacttc tggggccagg gcaccctcgt    840
gaccgtgtcc agcttcgtgc ccgtgttcct gccagccaag ccaaccacaa caccagcacc    900
cagaccacca acaccagcac caacaatcgc cagccagcca ctgtccctga ggccagaggc    960
atgcagacca gcagcaggcg gagccgtgca caccagagga ctggacttcg cctgcgacat   1020
ctacatctgg gcaccactgg ccggaacatg cggcgtgctg ctgctgagcc tggtcatcac   1080
cctgtactgc aaccaccgga acagagtgaa gttcagcaga tccgccgacg caccagccta   1140
ccagcaggga cagaaccagc tgtacaacga gctgaacctg ggagaagag aagagtacga   1200 cgtgctggat aagcggagag gcagagaccc tgagatgggc ggcaagccca gacgaagaa   1260 cccacaagag ggcctgtaca cgagctgca gaaagacaag atggccgagg cctacagcga   1320
gatcggaatg aaggcgagc gcagaagagg caagggacac gacggactgt accagggcct   1380
gagcacagcc accaaggata cctacgatgc cctgcacatg caggccctgc caccaagatg   1440
actatgaaga aggaaggcat ccagaccaga aaccgaaaaa tgtctagcaa atccaaaaag   1500
```

-continued

| | |
|---|---|
| tgcaaaaaag tgcatgactc actggaggac ttccccaaga acagctcgtt taacccggcc | 1560 |
| gccctctcca gacacatgtc ctccctgagc cacatctcgc ccttcagcca ctccagccac | 1620 |
| atgctgacca cgcccacgcc gatgcacccg ccatccagca | 1660 |

<210> SEQ ID NO 33
<211> LENGTH: 1786
<212> TYPE: DNA
<213> ORGANISM: Artificial Sequence
<220> FEATURE:
<223> OTHER INFORMATION: Synthetic Polynucleotide

<400> SEQUENCE: 33

| | |
|---|---|
| agacccaagc tggctagctc taaagaagcc cctgggagca cagctcatca ccatggcact | 60 |
| gccagtcaca gcactgctgc tgccactggc actgctgctc cacgccgcca gacccgacat | 120 |
| cgtgctgaca cagagcccag caagcctggc cgtgagccca ggccagagag ccacaatcac | 180 |
| atgcagagcc agcgagtccg tgtccttcct gggcatcaac ctgatccact ggtaccagca | 240 |
| gaagcccgga cagccaccca aactgctgat ctactccgcc agcaacctgc agtcaggcgt | 300 |
| gccagccaga ttcagcggca gcggcagcgg aaccgacttc accctgacaa tcagctcagt | 360 |
| ggaaccagaa gacaccgcca actactactg cctgcagagc aagaacttcc ccagaacctt | 420 |
| cggccaaggc accaaggtcg aaatcaaggg ctccacaagc ggcagcggaa agcccggaag | 480 |
| cggcgaggga agcaccaagg ccagatccag ctggtgcag agcggccccg aactgaagaa | 540 |
| acccggcgga agcgtgaaaa tctcctgcaa ggccagcggc tacaccttca cctcctacag | 600 |
| catcaactgg gtgcgccagg ccccaggcaa gggcctggaa tgggtcggct ggatcaacac | 660 |
| cgagacaaga gagcccgcct acgcccaggg cttcacaggc agattcacct tcagcgcaga | 720 |
| cacaagcaag agcatggcct acctgcagat caactccctg agagcagagg acaccgccgt | 780 |
| ctactactgc gccctggact acctctactc cctggacttc tggggccagg gcaccctcgt | 840 |
| gaccgtgtcc agcttcgtgc ccgtgttcct gccagccaag ccaaccacaa caccagcacc | 900 |
| cagaccacca acaccagcac caacaatcgc cagccagcca ctgtccctga ggccagaggc | 960 |
| atgcagacca gcagcaggcg gagccgtgca caccagagga ctggacttcg cctgcgacat | 1020 |
| ctacatctgg gcaccactgg ccggaacatg cggcgtgctg ctgctgagcc tggtcatcac | 1080 |
| cctgtactgc aaccaccgga caaaacgcgg gagaaaaaag ctcctctaca tcttcaagca | 1140 |
| accattcatg cgcccagtcc aaaccacaca ggaggaagac ggatgcagct gcaggttccc | 1200 |
| cgaagaggag gaaggcggat gcgagctcag agtgaagttc agcagatccg ccgacgcacc | 1260 |
| agcctaccag cagggacaga accagctgta caacgagctg aacctgggga agagaagaa | 1320 |
| gtacgacgtg ctggataagc ggagaggcag agaccctgag atgggcggca agcccagacg | 1380 |
| gaagaaccca caagagggcc tgtacaacga gctgcagaaa gacaagatgg ccgaggccta | 1440 |
| cagcgagatc ggaatgaagg gcgagcgcag aagaggcaag ggacacgacg gactgtacca | 1500 |
| gggcctgagc acagccacca aggataccta cgatgccctg cacatgcagg ccctgccacc | 1560 |
| aagatgacta tgaagaagga aggcatccag accagaaacc gaaaaatgtc tagcaaatcc | 1620 |
| aaaaagtgca aaaagtgca tgactcactg gaggacttcc ccaagaacag ctcgtttaac | 1680 |
| ccggccgccc tctccagaca catgtcctcc ctgagccaca tctcgccctt cagccactcc | 1740 |
| agccacatgc tgaccacgcc cacgccgatg cacccgccat ccagca | 1786 |

<210> SEQ ID NO 34
<211> LENGTH: 1660

```
<212> TYPE: DNA
<213> ORGANISM: Artificial Sequence
<220> FEATURE:
<223> OTHER INFORMATION: Synthetic Polynucleotide

<400> SEQUENCE: 34
agacccaagc tggctagctc taaagaagcc cctgggagca cagctcatca ccatggcact      60
gccagtcaca gcactgctgc tgccactggc actgctgctc cacgccgcca gacccgacat     120
cgtgctgaca cagagcccag caagcctggc cgtgagccca ggccagagag ccacaatcac     180
atgcagagcc agcgagtccg tgacaatcct gggctcccac ctgatccact ggtaccagca     240
gaagcccgga cagccaccca aactgctgat caacctggcc agcaacgtga acacaggcgt     300
gccagccaga ttcagcggca gcggcagcgg aaccgacttc accctgacaa tcagctcagt     360
ggaaccagaa gacaccgcca actactactg cctgcagagc agaacactgc cagaaccttt     420
cggccaaggc accaaggtcg aaatcaaggg ctccacaagc ggcagcggaa agcccggaag     480
cggcgaggga agcaccaagg ccagatccag gctggtgcag agcggccccg aactgaagaa     540
acccggcgga agcgtgaaaa tctcctgcaa ggccagcggc tacaccttca ccgactacag     600
catcaactgg gtgcgccagg ccccaggcaa gggcctggaa tgggtcggct ggatcaacac     660
cgagacaaga gagcccgcct acgcctacga cttcacaggc agattcacct tcagcgcaga     720
cacaagcaag agcatggcct acctgcagat caactccctg agagcagagg acaccgccgt     780
ctactactgc gccctggact acacctacgg catggactac tggggccagg gcaccctcgt     840
gaccgtgtcc agcttcgtgc ccgtgttcct gccagccaag ccaaccacaa caccagcacc     900
cagaccacca acaccagcac caacaatcgc cagccagcca ctgtccctga ggccagaggc     960
atgcagacca gcagcaggcg gagccgtgca caccagagga ctggacttcg cctgcgacat    1020
ctacatctgg gcaccactgg ccggaacatg cggcgtgctg ctgctgagcc tggtcatcac    1080
cctgtactgc aaccaccgga acagagtgaa gttcagcaga tccgccgacg caccagccta    1140
ccagcaggga cagaaccagc tgtacaacga gctgaacctg gggagaagag aagagtacga    1200
cgtgctggat aagcggagag cagagaccct tgagatgggc ggcaagccca gacgaaagaa    1260
cccacaagag ggcctgtaca acgagctgca gaaagacaag atggccgagg cctacagcga    1320
gatcggaatg aagggcgagc gcagaagagg caagggacac gacggactgt accagggcct    1380
gagcacagcc accaaggata cctacgatgc cctgcacatg caggccctgc caccaagatg    1440
actatgaaga aggaaggcat ccagaccaga aaccgaaaaa tgtctagcaa atccaaaaag    1500
tgcaaaaaag tgcatgactc actggaggac ttccccaaga acagctcgtt taacccggcc    1560
gccctctcca gacacatgtc ctccctgagc cacatctcgc ccttcagcca ctccagccac    1620
atgctgacca cgcccacgcc gatgcacccg ccatccagca                          1660

<210> SEQ ID NO 35
<211> LENGTH: 1786
<212> TYPE: DNA
<213> ORGANISM: Artificial Sequence
<220> FEATURE:
<223> OTHER INFORMATION: Synthetic Polynucleotide

<400> SEQUENCE: 35
agacccaagc tggctagctc taaagaagcc cctgggagca cagctcatca ccatggcact      60
gccagtcaca gcactgctgc tgccactggc actgctgctc cacgccgcca gacccgacat     120
cgtgctgaca cagagcccag caagcctggc cgtgagccca ggccagagag ccacaatcac     180
```

| | |
|---|---|
| atgcagagcc agcgagtccg tgacaatcct gggctcccac ctgatccact ggtaccagca | 240 |
| gaagcccgga cagccaccca aactgctgat caacctggcc agcaacgtga acacaggcgt | 300 |
| gccagccaga ttcagcggca gcggcagcgg aaccgacttc accctgacaa tcagctcagt | 360 |
| ggaaccagaa gacaccgcca actactactg cctgcagagc agaacactgc cagaaccttt | 420 |
| cggccaaggc accaaggtcg aaatcaaggg ctccacaagc ggcagcggaa agcccggaag | 480 |
| cggcgaggga agcaccaagg ccagatccag ctggtgcag agcggccccg aactgaagaa | 540 |
| acccggcgga agcgtgaaaa tctcctgcaa ggccagcggc tacaccttca ccgactacag | 600 |
| catcaactgg gtgcgccagg ccccaggcaa gggcctggaa tgggtcggct ggatcaacac | 660 |
| cgagacaaga gagcccgcct acgcctacga cttcacaggc agattcacct tcagcgcaga | 720 |
| cacaagcaag agcatggcct acctgcagat caactccctg agagcagagg acaccgccgt | 780 |
| ctactactgc gccctggact acacctacgg catggactac tggggccagg gcaccctcgt | 840 |
| gaccgtgtcc agcttcgtgc ccgtgttcct gccagccaag ccaaccacaa caccagcacc | 900 |
| cagaccacca acaccagcac caacaatcgc cagccagcca ctgtccctga ggccagaggc | 960 |
| atgcagacca gcagcaggcg gagccgtgca caccagagga ctggacttcg cctgcgacat | 1020 |
| ctacatctgg gcaccactgg ccggaacatg cggcgtgctg ctgctgagcc tggtcatcac | 1080 |
| cctgtactgc aaccaccgga caaaacgcgg gagaaaaaag ctcctctaca tcttcaagca | 1140 |
| accattcatg cgcccagtcc aaaccacaca ggaggaagac ggatgcagct gcaggttccc | 1200 |
| cgaagaggag gaaggcggat gcgagctcag agtgaagttc agcagatccg ccgacgcacc | 1260 |
| agcctaccag cagggacaga accagctgta caacagctg aacctgggga agagaagaa | 1320 |
| gtacgacgtg ctggataagc ggagaggcag agaccctgag atgggcggca agcccagacg | 1380 |
| gaagaaccca agagggccc tgtacaacga gctgcagaaa gacaagatgg ccgaggccta | 1440 |
| cagcgagatc ggaatgaagg gcgagcgcag aagaggcaag ggacacgacg gactgtacca | 1500 |
| gggcctgagc acagccacca ggataccta cgatgccctg cacatgcagg ccctgccacc | 1560 |
| aagatgacta tgaagaagga aggcatccag accagaaacc gaaaaatgtc tagcaaatcc | 1620 |
| aaaaagtgca aaaagtgca tgactcactg gaggacttcc ccaagaacag ctcgtttaac | 1680 |
| ccggccgccc tctccagaca catgtcctcc ctgagccaca tctcgcccctt cagccactcc | 1740 |
| agccacatgc tgaccacgcc cacgccgatg cacccgccat ccagca | 1786 |

<210> SEQ ID NO 36
<211> LENGTH: 1739
<212> TYPE: DNA
<213> ORGANISM: Artificial Sequence
<220> FEATURE:
<223> OTHER INFORMATION: Synthetic Polynucleotide

<400> SEQUENCE: 36

| | |
|---|---|
| agacccaagc tggctagctc taaagaagcc cctgggagca cagctcatca ccatggctct | 60 |
| gccggtaaca gcgcttcttc tcccgcttgc cctcctcttg cacgctgctc ggccagatat | 120 |
| tgtcctcaca cagagcccgt cctcactttc agcgagcgtc ggggaccgcg ctaccatcag | 180 |
| ttgtcgagcc agtgaaagcg tcactattct ggggagccac cttatacatt ggtatcaaca | 240 |
| aaagccaggc caggccccca aactgctgat tcagctcgca tctaatgttc agactggagt | 300 |
| gcctgcaagg tttagcggta gtgggtcagg acagatttc accttgacca ttagctcagt | 360 |
| tgagcctgaa gatgtggccg tttattactg cctccaaagc cgcactatac ctcggacctt | 420 |
| cggccaggga acaaaggtgg agattaaggg tagtacctca ggtagtggca agccagggag | 480 |

```
cggcgagggg tctacaaagg gtcaaattca attggtgcag tccggaccag aactgaaaaa      540
accgggcggg agcgtcaaga tttcctgtgc agcatcaggc tatacattta ctgattacag      600
tattaactgg gtgagacaag cgcctggaaa gggccttgag tgggtgggtt ggattaacac      660
ggagactaga gaacccgcgt acgcctacga ttttagaggc cggttcactt tctccgccga      720
tacaagtaaa tccacagcat atctccaaat gaatagcctt agagcggagg ataccgccgt      780
gtattattgc gcgctcgact attcttacgc aatggactac tggggcaggg tactctcgt       840 caccgtatcc tcatttgttc ccgtattttt gcccgccaag ccgaccacta ctccggcccc      900
tcgacctccg acccctgctc cgactattgc gagtcaacca ttgagccttc ggcctgaggc      960
atgtagaccg gcagctggtg gcgcagtcca tacacgaggg cttgattttg cgtgcgacat     1020
ctatatatgg gcgccattgg ctgggacgtg cggcgtcctt ctcttgtcac tcgtgataac     1080
tctgtactgc aatcacagaa accgcgtgaa gttttccaga agcgcggacg cgccggccta     1140
tcaacaaggg cagaatcagc tgtacaacga actcaatttg gggcgaaggg aggagtatga     1200
tgttttggac aaaaggcgag gccgcgaccc tgaaatgggc ggtaagccac gcagaaaaaa     1260
cccccaagag ggattgtaca atgaactgca aaaagacaag atggctgagg catacagtga     1320
gataggaatg aaaggtgaac ggcgccgggg aaaaggacat gacgggttgt accagggtct     1380
tagcactgca acgaaagata cctatgacgc cctgcacatg caagcattgc ccccacggtg     1440
actatgaaga aggaaggcat ccagaccaga aaccgaaaaa tgtctagcaa atccaaaaag     1500
tgcaaaaaag tgcatgactc actggaggac ttccccaaga acagctcgtt taacccggcc     1560
gccctctcca gacacatgtc ctccctgagc cacatctcgc ccttcagcca ctccagccac     1620
atgctgacca cgcccacgcc gatgcacccg ccatccagca aaaaaaaaaa aaaaaaaaa      1680 aaaaaaaaaa aaaaaaaaaa aaaaaaaaaa aaaaaaaaaa aaaaaaaaaa aaaaaaaa       1739
```

<210> SEQ ID NO 37
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 37

```
agacccaagc tggctagctc taaagaagcc cctgggagca cagctcatca ccatggcact       60
gccggtaaca gcgctcctcc tcccgctcgc cctcctcctc cacgcagcac ggccagacat      120
cgtcctcaca cagagcccga gcagcctcag cgcgagcgtc ggggaccgcg caaccatcag      180
ctgccgagcc agcgaaagcg tcacaatcct cgggagccac ctgatacact ggtaccaaca      240
aaagccaggc caggccccca aactgctgat ccagctcgca agcaacgtcc agacaggagt      300
gccagcaagg ttcagcggaa gcgggagcgg aacagacttc accctcacca tcagcagcgt      360
cgagccagaa gatgtggccg tctactactg cctccaaagc cgcacaatac cacgaccctt      420
cggccaggga acaaaggtgg agatcaaggg aagcaccagc ggaagcggca agccagggag      480
cggcgagggg agcacaaagg gacaaatcca actcgtgcag agcggaccag aactgaaaaa      540
gccgggcgga agcgtcaaga tcagctgcgc agcaagcggc tacacattca cagactacag      600
catcaactgg gtgagacaag cgccaggaaa gggcctcgaa tgggtgggat ggatcaacac      660
ggagacaaga gaacccgcat acgcctacga cttcagaggc cggttcacat tcagcgccga      720
cacaagcaag agcacagcat acctccaaat gaacagcctc agagcggagg acaccgccgt      780
```

```
gtactactgc gcgctcgact acagctacgc aatggactac tggggacagg gaacactcgt    840
caccgtaagc agcttcgtac ccgtattcct ccccgccaag ccgaccacaa caccggcccc    900
acgaccacca acaccagccc cgacaatcgc gagccaacca ctcagcctcc ggccagaggc    960
gtgcagaccg gcagcaggag gcgcagtcca cacacgagga ctcgacttcg cgtgcgacat   1020
atacatctgg gcaccactcg caggaacgtg cggcgtcctc ctcctcagcc tcgtgataac   1080
actgtactgc aaccacagaa accgcgtgaa gttcagcaga agcgcggacg cgccggccta   1140
ccaacaagga cagaaccagc tgtacaacga actcaacctc ggacgaaggg aggagtacga   1200
cgtcctcgac aaaaggcgag gccgcgaccc agaaatgggc ggaaagccac gcagaaaaaa   1260
cccccaagag ggactctaca acgaactgca aaaggacaag atggcagagg catacagcga   1320
gataggaatg aaaggagaac ggcgccgggg aaaaggacac gacgggctct accagggact   1380
cagcacagca acgaaagaca cctacgacgc cctgcacatg caagcactcc ccccacggtg   1440
aacctgagac tggtggcttc tagaagcagc cattaccaac tgtaccttcc cttcttgctc   1500
agccaataaa tatatcctct ttcactcag                                     1529

<210> SEQ ID NO 38
<211> LENGTH: 1724
<212> TYPE: DNA
<213> ORGANISM: Artificial Sequence
<220> FEATURE:
<223> OTHER INFORMATION: Synthetic Polynucleotide

<400> SEQUENCE: 38
gggagaccca agctggctag cctcgcagtt cggcggtccc gcgggtctgt ctgttgcttc     60
aacagtgttt ggacggaaca gatccgggga ctctcttcca gccatggcac tgcctgttac    120
agctctgctg ctgcctctgg cactgctgct tcatgccgcc agacctgaca ttgttctgac    180
acagtcccct tctagtttga gcgcgagtgt tggcgaccga gctacgataa gctgtcgagc    240
tagcgaaagc gtgacgatcc tgggttccca ccttattcat tggtatcaac agaaaccagg    300
gcaggctcct aaacttctca tacagttggc cagcaatgtt caaaccggtg tgcccgcacg    360
cttcagcgga tcagggtcag gaaccgattt cacgctcaca attagcagtg tggagcctga    420
tgacgtagcc gtgtactact gtctgcaaag ccgcaccatc ccgagaacgt ttgggggcgg    480
cacgaaattg gaaattaaag gaagcacttc cgggagtggg aagcctggga gtggcgaagg    540
gtcaacaaag gggcagatac agttggtcca gagcgggccc gagttgaaaa agccaggtgg    600
atcagttaaa atttcttgtg ctgcgtccgg atatactttt actgactatt ctatcaactg    660
ggtcaaacaa gctcccggta aaggattgga atgggtcgga tggataaaca ctgaaacccg    720
cgagcctgct tatgcttacg attttcgagg tagattcacc ttctcacttg atacatccaa    780
aagtacggct tacctgcaaa tgaactcact gagagcagaa gataccgccg tttactattg    840
tgccctcgac tatagttacg ccatggatta ttggggacaa gggactctcg tgaccgtaag    900
tagctttgtg cctgtgttcc tgcctgccaa gcctaccaca acaccagctc ctagacctcc    960
aactcctgct cctacaatcg cctctcagcc actgtctctg aggcctgaag cttgtagacc   1020
tgctgctggc ggagccgtgc ataccagagg actggatttc gcctgcgaca tctacatctg   1080
ggctcctctg gctggaacat gtggcgtgct gctgctgagc ctggtcatca ccctgtactg   1140
caaccaccgg aacagagtga agttcagcag atccgccgat gctcctgcct accagcaggg   1200
acagaaccag ctgtacaacg agctgaacct ggggagaaga gaagagtacg acgtgctgga   1260 taagcgggaga ggcagagatc ctgagatggg cggcaagccc agacgaagga atcctcaaga   1320
```

```
gggcctgtat aatgagctgc agaaagacaa gatggccgag gcctacacgcg agatcggaat    1380 gaagggcgag cgcagaagag gcaagggaca cgatggactg taccagggcc tgagcacagc    1440
caccaaggat acctatgatg ccctgcacat gcaggccctg cctccaagat gagggcccgt    1500
ttaaacccgc tggctcgctt tcttgctgtc caatttctat taaaggttcc tttgttccgt    1560
aagtccaact actaaactgg gggatattat gaagggcctt gagcatctgg attctgccta    1620
ataaaaaaca tttattttca ttgcaaaaaa aaaaaaaaaa aaaaaaaaaa aaaaaaaaaa    1680
aaaaaaaaaa aaaaaaaaaa aaaaaaaaaa aaaaaaaaaa aaaa                      1724

<210> SEQ ID NO 39
<211> LENGTH: 1660
<212> TYPE: DNA
<213> ORGANISM: Artificial Sequence
<220> FEATURE:
<223> OTHER INFORMATION: Synthetic Polynucleotide

<400> SEQUENCE: 39
agacccaagc tggctagctc taaagaagcc cctgggagca cagctcatca ccatggctct       60
gccggtaaca gcgcttcttc tcccgcttgc cctcctcttg cacgctgctc ggccagacat      120
agtattgacg caatccccccg cctctctcgc agtctctccc ggacaacggg ccactataac     180
ttgcagggca agtgagagtg tgacaatcct gggatcacac ctgatacatt ggtatcagca      240
aaagccgggt caaccccccta agttgctgat acaactggca tctaatgtac aaacgggagt    300
ccccgcacgg ttctctggtt ctggttctgg cactgacttc acattgacaa tctcaagtgt     360
tgaacctgag gacacagcca attattattg cttgcaatct cgaacaattc ctcgcacttt     420
cggtcagggc acgaaggttg aaattaaagg tagtacctca ggtagtggca agccagggag      480
cggcgagggg tctacaaagg gtcaaatcca gcttgtgcaa tctggcccgg agctgaaaaa      540
acccggtgga tctgtgaaaa ttagctgcaa agcgtcagga tatacattca cagactatag     600
catcaactgg gtccggcagg cacccggtaa gggtctggaa tgggttggtt ggattaacac      660
tgagacccgt gagcccgcct atgcatacga ttttacggga cggtttactt tcagcgccga    720
cacgagcaag agcatggcgt acctccagat taacagtctg agggcggagg acacagccgt     780
ctactattgc gcgttggatt atagctacgc gatggactac tgggggcaag gtacacttgt      840
cacggtgtca tcttttgttc ccgtattttt gcccgccaag ccgaccacta ctccggcccc      900
tcgacctccg accctgctc cgactattgc gagtcaacca ttgagccttc ggcctgaggc      960
atgtagaccg gcagctggtg gcgcagtcca tacacgaggc cttgattttg cgtgcgacat    1020
ctatatatgg gcgccattgg ctgggacgtg cggcgtcctt ctcttgtcac tcgtgataac    1080
tctgtactgc aatcacagaa accgcgtgaa gttttccaga agcgcggacg cgccggccta    1140
tcaacaaggg cagaatcagc tgtacaacga actcaatttg gggcgaaggg aggagtatga    1200
tgttttggac aaaaggcgag gccgcgaccc tgaaatgggc ggtaagccac gcagaaaaaa    1260 ccccccaagag ggattgtaca atgaactgca aaaagacaag atggctgagg catacagtga    1320
gataggaatg aaaggtgaac ggcgccgggg aaaaggacat gacgggttgt accagggtct    1380
tagcactgca acgaaagata cctatgacgc cctgcacatg caagcattgc ccccacggtg    1440
actatgaaga aggaaggcat ccagaccaga aaccgaaaaa tgtctagcaa atccaaaaag    1500
tgcaaaaaag tgcatgactc actggaggac ttccccaaga acagctcgtt taacccggcc    1560
gccctctcca gacacatgtc ctccctgagc cacatctcgc ccttcagcca ctccagccac    1620
```

| atgctgacca cgcccacgcc gatgcacccg ccatccagca | 1660 |

<210> SEQ ID NO 40
<211> LENGTH: 1660
<212> TYPE: DNA
<213> ORGANISM: Artificial Sequence
<220> FEATURE:
<223> OTHER INFORMATION: Synthetic Polynucleotide

<400> SEQUENCE: 40

| agacccaagc tggctagctc taaagaagcc cctgggagca cagctcatca ccatggcact | 60 |
|---|---|
| gccagtcaca gcactgctgc tgccactggc actgctgctc cacgccgcca gacccgacat | 120 |
| cgtgctgaca cagagcccag caagcctggc cgtgagccca ggccagagag ccacaatcac | 180 |
| atgcagagcc agcgagtccg tgacaatcct gggctcccac ctgatccact ggtaccagca | 240 |
| gaagcccgga cagccaccca aactgctgat ccagctggcc agcaacgtgc agacaggcgt | 300 |
| gccagccaga ttcagcggca gcggcagcgg aaccgacttc accctgacaa tcagctcagt | 360 |
| ggaaccagaa gacaccgcca actactactg cctgcagagc agaacaatcc ccagaacctt | 420 |
| cggccaaggc accaaggtcg aaatcaaggg ctccacaagc ggcagcggaa agcccggaag | 480 |
| cggcgaggga agcaccaagg ccagatcca gctggtgcag agcggccccg aactgaagaa | 540 |
| acccggcgga agcgtgaaaa tctcctgcaa ggccagcggc tacaccttca ccgactacag | 600 |
| catcaactgg gtgcgccagg ccccaggcaa gggcctggaa tgggtcggct ggatcaacac | 660 |
| cgagacaaga gagcccgcct acgcctacga cttcacaggc agattcacct tcagcgcaga | 720 |
| cacaagcaag agcatggcct acctgcagat caactccctg agagcagagg acaccgccgt | 780 |
| ctactactgc gccctggact acagctacgc catggactac tggggccagg gcaccctcgt | 840 |
| gaccgtgtcc agcttcgtgc ccgtgttcct gccagccaag ccaaccacaa caccagcacc | 900 |
| cagaccacca acaccagcac caacaatcgc cagccagcca ctgtccctga ggccagaggc | 960 |
| atgcagacca gcagcaggcg gagccgtgca caccagagga ctggacttcg cctgcgacat | 1020 |
| ctacatctgg gcaccactgg ccggaacatg cggcgtgctg ctgctgagcc tggtcatcac | 1080 |
| cctgtactgc aaccaccgga acagagtgaa gttcagcaga tccgccgacg caccagccta | 1140 |
| ccagcaggga cagaaccagc tgtacaacga gctgaacctg ggagaagaag aagagtacga | 1200 |
| cgtgctggat aagcggagag cagagaccct tgagatgggc ggcaagccca gacgaagaa | 1260 |
| cccacaagag ggcctgtaca cgagctgca gaaagacaag atggccgagg cctacagcga | 1320 |
| gatcggaatg aagggcgagc gcagaagagg caagggacac gacggactgt accagggcct | 1380 |
| gagcacagcc accaaggata cctacgatgc cctgcacatg caggccctgc caccaagatg | 1440 |
| actatgaaga aggaaggcat ccagaccaga aaccgaaaaa tgtctagcaa atccaaaaag | 1500 |
| tgcaaaaaag tgcatgactc actggaggac ttccccaaga acagctcgtt taacccggcc | 1560 |
| gccctctcca gacacatgtc ctccctgagc cacatctcgc ccttcagcca ctccagccac | 1620 |
| atgctgacca cgcccacgcc gatgcacccg ccatccagca | 1660 |

<210> SEQ ID NO 41
<211> LENGTH: 1644
<212> TYPE: DNA
<213> ORGANISM: Artificial Sequence
<220> FEATURE:
<223> OTHER INFORMATION: Synthetic Polynucleotide

<400> SEQUENCE: 41

| gggagaccca agctggctag cctcgcagtt cggcggtccc gcgggtctgt ctgttgcttc | 60 |

| | |
|---|---|
| aacagtgttt ggacggaaca gatccgggga ctctcttcca gccatggctc tgcccgtaac | 120 |
| cgccctgctc ctgccactcg cactcctcct gcatgcggct aggccggata ttgtaatgac | 180 |
| gcaatcccct gactcactga gtgtgtcctt gggagagaga gccacgataa attgtcgggc | 240 |
| ctccgagtca gtcactatac tcggttctca cctgatccac tggtaccaac aaaagcctgg | 300 |
| gcagccaccg aaacttttga tacagttggc ctccaatgtc caaactgggg ttcccgaccg | 360 |
| ctttagcgga agcgggagcg gtaccgattt taccctcacc atatcatcac tccaagctga | 420 |
| ggacgtggcc gtttactact gtctccagtc aaggacaata ccgcgaacat tcggtggagg | 480 |
| tactaaagtt gaaataaaag gttccacaag tggctcaggg aagccaggga gtggtgaggg | 540 |
| aagcacaaaa ggccaaatac aactggtgca gtctggagca gaagtcaaga agccaggtgc | 600 |
| ctccgttaag atttcttgta aagcttccgg ctatacctt accgattaca gcattaattg | 660 |
| ggtccgccag gcccctgggc agggccttga gtggatgggc tggataaata cagagactag | 720 |
| agaacccgcg tatgcatacg attttcgagg ccgggtgact atgacgcgcg cacctccgc | 780 |
| gtctactgca tacctgcaga tcagtagcct gaaagccgaa gataccgccg tttacttctg | 840 |
| cgccctcgac tattcttacg caatggacta ctggggacaa ggttctctcg ttactgtatc | 900 |
| tagctttgtt ccagtgttcc tcccggcgaa acccaccact accccagccc ctcgcccacc | 960 |
| gactccggcg ccgacgattg ccagtcagcc gttgagcctc cgaccggagg cgtgtcgccc | 1020 |
| cgcggcagga ggggccgtgc atactagggg acttgatttt gcctgtgaca tatatatg | 1080 |
| ggccccttg gccggtacct gtggtgtcct gctgcttagt ttggtgataa cactctattg | 1140 |
| taaccatcgc aatcgagtta agttcagtcg gtcagctgat gctccggctt accagcaagg | 1200 |
| ccagaatcag ctgtacaatg agctcaacct gggtcggcga gaagagtatg atgtactgga | 1260 |
| caaacggaga ggtcgggatc ccgaaatggg gggtaaacca cgcaggaaga acccacaaga | 1320 |
| ggggttgtac aatgaactgc agaaagataa gatggccgag gcttacagtg aaatcgggat | 1380 |
| gaaaggagaa cggagacgag gtaaggggca cgacggactc tatcaaggac tcagcaccgc | 1440 |
| tacaaaggat acctatgatg cactccatat gcaagccctt cccccaaggt aggggcccgt | 1500 |
| ttaaacccgc tggctcgctt tcttgctgtc caatttctat taaaggttcc tttgttccgt | 1560 |
| aagtccaact actaaactgg gggatattat gaagggcctt gagcatctgg attctgccta | 1620 |
| ataaaaaaca tttattttca ttgc | 1644 |

<210> SEQ ID NO 42
<211> LENGTH: 1644
<212> TYPE: DNA
<213> ORGANISM: Artificial Sequence
<220> FEATURE:
<223> OTHER INFORMATION: Synthetic Polynucleotide

<400> SEQUENCE: 42

| | |
|---|---|
| gggagaccca agctggctag cctcgcagtt cggcggtccc gcgggtctgt ctgttgcttc | 60 |
| aacagtgttt ggacggaaca gatccgggga ctctcttcca gccatggcgc tcccagttac | 120 |
| agccttgttg ttgcccttgg ccctccttct ccacgctgca cgcccggaca tagttttgac | 180 |
| ccagagccct gcaagtttgg ctgtcagtct tggagagcga gctacaatta gttgcagagc | 240 |
| gtctgaaagc gtctccatat tgggcagtca ccttttgcac tggtaccaac agaagccagg | 300 |
| acagccacca aagctgctta tttacctcgc ctccaatttg caaactggag taccggctcg | 360 |
| attctccgga tctggttctg gaacagactt caccccttacg atatcaagtc tggaggctga | 420 |

```
ggatgtcgcg gtttactact gcctccaatc acgaacaata ccgagaacgt tcggccaggg    480
gactaaactt gaaatcaagg gtagtacgag tggaagtggg aaacctgggt ctggtgaggg    540
gtctacgaaa gggcaaatac agctggttca atcaggcgcc gaagtaaaaa aaccgggggc    600
atctgtgaaa atatcctgca aagcgtctgg atacacattt acagactatt ccatcaactg    660
ggtccgccag gcccccggcc aaggtctgga atggatgggc tggatcaaca cagaaacccg    720
ggaacctgca tacgcttacg attttcgcgc ccgggtcact atgacccgcg atacaagtgc    780
ctccaccgca tatctccaaa tctcatcttt gaaggcagaa gatacagccg tctacttttg    840
tgcactggac tatagctatg cgatggatta ctggggtcaa ggcagccttg ttactgtgtc    900
cagctttgtg cccgtatttc tcccggccaa gccaactact accccctgccc cgcgaccgcc    960 aacgccagcg cctaccattg cgagtcaacc actctcactg cggccagaag cctgccgacc   1020
tgccgccggg ggggcagtac acactcgcgg tcttgatttt gcttgcgaca tatatatctg   1080 ggcccccactg gctgggacgt gtggcgtttt gctgcttagt ttggtcataa ccctctattg   1140
caaccacaga atcgcgtta aatttagcag aagtgctgac gcacctgcat accagcaagg   1200
tcagaaccaa ctgtataatg aactgaattt gggacgcagg gaagagtatg acgtcttgga   1260
taaaagaaga ggacgcgatc cggagatggg tgggaaacct cgccgaaaga accccccaaga   1320 aggtttgtat aatgaactcc agaaggacaa aatggcggag cgtatagcg agattggaat    1380 gaaggggggaa agacgacgcg gcaaaggtca tgacggattg tatcagggcc tctctacggc   1440
tactaaagat acttatgatg ctctccatat gcaggcgttg ccaccaaggt gagggcccgt   1500
ttaaacccgc tggctcgctt tcttgctgtc caatttctat taaaggttcc tttgttccgt   1560
aagtccaact actaaactgg gggatattat gaagggcctt gagcatctgg attctgccta   1620
ataaaaaaca tttattttca ttgc                                         1644

<210> SEQ ID NO 43
<211> LENGTH: 1644
<212> TYPE: DNA
<213> ORGANISM: Artificial Sequence
<220> FEATURE:
<223> OTHER INFORMATION: Synthetic Polynucleotide

<400> SEQUENCE: 43
gggagaccca agctggctag cctcgcagtt cggcggtccc gcgggtctgt ctgttgcttc     60
aacagtgttt ggacggaaca gatccgggga ctctcttcca gccatggctc tgcccgtaac    120
cgcactgctt ctgccactcg ctctgttgct ccacgccgct agacctgaca tcgtgctgac    180
gcaaagcccg gcgtcactcg ccgttagttt gggaaaacgg gcgacaatat cttgtagagc    240
ttctgaaagc gtcactatcc tgggttcaca tctgatacac tggtaccagc agaagccagg    300
acagccaccc aaactgctga tatatcttgc ttctaatgta caaacaggcg taccagcccg    360
cttcagcggt tccgggtctg gtacagattt tactttgacc atatccagtt tggaggctga    420
ggacgttgcc gtctactact gtctccaaag tcggactata ccgaggacct ttggtcaggg    480
gacaaagctt gagataaaag ggtccacatc cgggtcagga aaacctggaa gtggggaggg    540
atctacaaaa gggcaggtac aactggtcca gtccggggcg aagtaaaaaa acccggggc    600 ctctgtaaaa atttcctgta aggcctctgg ttacacgttt accgactaca gtatcaattg    660
ggtgcggcaa gcccgggcc aagggttgga atggatgggt tggataaata ctgagacacg    720
ggaaccagca tacgcctacg attttcgggg tcgagtcaca atgacgagag atacttctgc    780
cagtactgct tatctccaga tcagttccct caaagcggaa gacaccgcag tatacttctg    840
```

```
tgccctcgac tattcatacg caatggatta ttggggtcaa ggctcacttg tgacggtgag      900
ttccttcgtc cccgtcttct tgccggcgaa gcccactact acgccggcac cacgccccc      960 cactcctgcg ccaactatag cttcacaacc cttgagcctg aggcctgagg cgtgtaggcc     1020
agcagcaggt ggggcagtgc acactagggg cctcgatttt gcctgcgata tctatatttg     1080
ggcaccgctc gcgggtacgt gcggcgttct tttgttgtcc ttggtcatca cactgtactg     1140
taaccatcgg aatcgcgtaa aattcagccg gagtgccgat gcaccggcgt accagcaagg     1200
tcaaaaccag ctctacaatg agctgaatct gggaagacgc gaagagtatg acgttcttga     1260
taagaggaga ggccgagacc ccgaaatggg ggggaagccc aggcgaaaga tccccagga     1320 gggtttgtac aatgagcttc aaaaagacaa gatggcagag gcctactccg aaatagggat     1380
gaaaggggaa agacggagag gcaagggtca tgacggactc tatcagggtc ttagcaccgc     1440
cacgaaggac acatacgatg cccttcatat gcaagcactc cccctagat gagggcccgt      1500 ttaaacccgc tggctcgctt tcttgctgtc caatttctat taaaggttcc tttgttccgt     1560
aagtccaact actaaactgg gggatattat gaagggcctt gagcatctgg attctgccta     1620
ataaaaaaca tttattttca ttgc                                            1644
```

<210> SEQ ID NO 44
<211> LENGTH: 1644
<212> TYPE: DNA
<213> ORGANISM: Artificial Sequence
<220> FEATURE:
<223> OTHER INFORMATION: Synthetic Polynucleotide

<400> SEQUENCE: 44

```
gggagaccca agctggctag cctcgcagtt cggcggtccc gcgggtctgt ctgttgcttc       60
aacagtgttt ggacggaaca gatccgggga ctctcttcca gccatggcgc ttccagtcac      120
cgctctcctt ttgccgctcg cactgcttct gcatgcggcc cgccccgata tcgttatgac      180
ccagtctcct gacagtctga gtgtcagtct cggagagcgg gcaacgatta attgtcgcgc      240
ctccgaaagc gttaccatac tcgggagcca tcttatccat tggtaccaac aaaagccagg      300
tcagcctcct aagttgttga ttcaacttgc tagcaacgtg caaacgggcg ttccagacag      360
gtttagcgga tccggaagcg gaacagactt cactctgacg atatcaagtt gcaagcgga      420 ggacgtagcg gtttactact gccttcgag taggacaatc cctagaacat cggcggcgg      480 gacaaaggtg gaaataaagg gatccaccag tggaagcggg aagccgggta gcggtgaagg     540
cagcactaag ggacaaatcc aactcgtaca gagtggggca gaggtgaaga acctggggga     600
gagtgtaaaa atttcttgca aagcctcagg ctacacattc acggattata gcattaattg     660
ggtgcgacag gcgcccggtc aaggacttaa gtggatgggc tggatcaaca cggaaacgcg     720
cgaaccggcg tatgcctatg actttcgagg aaggttcgca ttcagccttg acacgtccgc     780
atcaaccgcc taccttcaga tcagttcact caaagctgaa gatacggctg tgtattttg     840 cgcacttgat tatagctatg ccatggacta ctggggtcag ggaaccttgg ttactgtatc     900
ttctttcgta ccagtttttt tgccggctaa accgactacc acgccggcac cacggccccc     960
gacacccgct ccaacaatag cgtcccaacc cctttcactt aggccggagg cctgcagacc    1020
tgctgctggg ggagctgtcc atactcgggg acttgacttc gcgtgcgaca tatacatctg    1080
ggcgcctctt gccggcacct gtggtgtatt gttgttgtct cttgttatca ctctgtactg    1140
taaccaccgc aacagggtta agttcagccg ctccgcagat gctcctgcct accagcaggg    1200
```

| | |
|---|---:|
| acaaaatcaa ctttataacg aattgaacct tgggcgaagg gaggaatatg atgttcttga | 1260 |
| caaaaggcgc ggcagggatc cggagatggg aggtaagcca cgcaggaaga atccgcagga | 1320 |
| gggcttgtat aacgaactcc agaaagataa aatggcagaa gcctattccg agataggaat | 1380 |
| gaaggggggag cgaagacggg gaaaaggtca cgatgggctg tatcagggcc tctctaccgc | 1440 |
| cactaaggac acttatgacg cattgcacat gcaggcgttg ccaccacggt gagggcccgt | 1500 |
| ttaaacccgc tggctcgctt tcttgctgtc caatttctat taaaggttcc tttgttccgt | 1560 |
| aagtccaact actaaactgg gggatattat gaagggcctt gagcatctgg attctgccta | 1620 |
| ataaaaaaca tttattttca ttgc | 1644 |

<210> SEQ ID NO 45
<211> LENGTH: 1644
<212> TYPE: DNA
<213> ORGANISM: Artificial Sequence
<220> FEATURE:
<223> OTHER INFORMATION: Synthetic Polynucleotide

<400> SEQUENCE: 45

| | |
|---|---:|
| gggagaccca agctggctag cctcgcagtt cggcggtccc gcgggtctgt ctgttgcttc | 60 |
| aacagtgttt ggacggaaca gatccgggga ctctcttcca gccatggcac tcccagttac | 120 |
| ggctttgttg ctcccgctcg cgttgttgct gcatgctgct cgcccagaca tcgtcctcac | 180 |
| gcaaagtccc gcaagtctcg ccgtctcatt gggcgaaaga gcgacaatat cctgtcgagc | 240 |
| gtcagagtct gttagtatcc ttggcagcca ctatctggct tggtatcagc agaaaccagg | 300 |
| gcagcctccc aagctgctga tttatctcgc gagcaatctc cagacaggtg tcccagcacg | 360 |
| cttcagtgga tctggcagcg gaacagattt tacactcacg atttcttccc tggaggctga | 420 |
| agatgtggca gtgtactatt gtcaacagag cagaactatc ccgagaacat ttgggcaggg | 480 |
| cactaaactt gaaatcaaag ggagtacgag tggtagtgga aaaccgggat ccggcgaagg | 540 |
| ctccacaaag gggcaaatac agctggtcca gtctggagct gaggtgaaaa agcccggtga | 600 |
| gtctgtaaag atttcctgca aggcaagtgg ttacactttt acggattact caatcaattg | 660 |
| ggttcggcaa gcacctggac agggtttgaa gtggatggga tggataaata cagaaacaag | 720 |
| ggaacctgcc tatgcctatg actttcgggg tagattcgcc ttctcacttg acacaagtgc | 780 |
| cagtacagcc tatcttcaga tttcaagcct gaaggcggaa gatacggccg tctattttg | 840 |
| tgcgcttgac tatagttatg cgatggatta ttggggccaa ggcacactgg tcacagttag | 900 |
| ctcttttgtc cctgttttcc tcccagcaaa accaacaact acaccgcgc cgaggccgcc | 960 |
| caccccctgcc cctaccatcg cctcacagcc attgagcctc cgccccgagg catgcagacc | 1020 |
| ggcagctgga ggtgccgtac acactcgagg gctcgacttc gcatgtgata tttatatctg | 1080 |
| ggcgccattg gcgggtactt gcggtgtgct gctccttagc cttgtcataa ccctctactg | 1140 |
| caatcatcgc aatagggtca aattttcaag gtcagcagat gctccggcgt atcagcaggg | 1200 |
| gcaaaaccaa ctttacaatg agctcaacct gggtagacgc gaggagtacg acgtgctcga | 1260 |
| caaaaggagg ggtcgggatc cggaaatggg gggcaaaccc cgcaggaaga acccacagga | 1320 |
| aggactgtat aatgagctcc agaaagacaa aatggcagag gcatattctg agataggaat | 1380 |
| gaaaggcgag cggagaagag gtaaagggca cgacggactt tatcagggtc tttcaacagc | 1440 |
| gactaaggat acatatgacg cattgcacat gcaagctctc ccacctagat gagggcccgt | 1500 |
| ttaaacccgc tggctcgctt tcttgctgtc caatttctat taaaggttcc tttgttccgt | 1560 |
| aagtccaact actaaactgg gggatattat gaagggcctt gagcatctgg attctgccta | 1620 |

```
ataaaaaaca tttattttca ttgc                                       1644

<210> SEQ ID NO 46
<211> LENGTH: 1644
<212> TYPE: DNA
<213> ORGANISM: Artificial Sequence
<220> FEATURE:
<223> OTHER INFORMATION: Synthetic Polynucleotide

<400> SEQUENCE: 46
gggagaccca agctggctag cctcgcagtt cggcggtccc gcgggtctgt ctgttgcttc     60
aacagtgttt ggacggaaca gatccgggga ctctcttcca gccatggcac tgcctgttac    120
agctctgctg ctgcctctgg cactgctgct tcatgccgcc agacctgaca ttgttctgac    180
acagtcccct tctagtttga gcgcgagtgt tggcgaccga gctacgataa gctgtcgagc    240
tagcgaaagc gtgacgatcc tgggttccca ccttattcat tggtatcaac agaaaccagg    300
gcaggctcct aaacttctca tacagttggc cagcaatgtt caaaccggtg tgcccgcacg    360
cttcagcgga tcagggtcag gaaccgattt cacgctcaca attagcagtg tggagcctga    420
tgacgtagcc gtgtactact gtctgcaaag ccgcaccatc ccgagaacgt ttgggggcgg    480
cacgaaattg gaaattaaag gaagcacttc cgggagtggg aagcctggga gtggcgaagg    540
gtcaacaaag gggcagatac agttggtcca gagcgggccc gagttgaaaa agccaggtgg    600
atcagttaaa atttcttgtg ctgcgtccgg atatactttt actgactatt ctatcaactg    660
ggtcaaacaa gctcccggta aaggattgga atgggtcgga tggataaaca ctgaaacccg    720
cgagcctgct tatgcttacg attttcgagg tagattcacc ttctcacttg atacatccaa    780
aagtacggct tacctgcaaa tgaactcact gagagcagaa gataccgccg tttactattg    840
tgccctcgac tatagttacg ccatggatta ttggggacaa gggactctcg tgaccgtaag    900
tagctttgtg cctgtgttcc tgcctgccaa gcctaccaca acaccagctc ctagacctcc    960
aactcctgct cctacaatcg cctctcagcc actgtctctg aggcctgaag cttgtagacc   1020
tgctgctggc ggagccgtgc ataccagagg actggatttc gcctgcgaca tctacatctg   1080
ggctcctctg gctggaacat gtggcgtgct gctgctgagc ctggtcatca ccctgtactg   1140
caaccaccgg aacagagtga agttcagcag atccgccgat gctcctgcct accagcaggg   1200
acagaaccag ctgtacaacg agctgaacct ggggagaaga gaagagtacg acgtgctgga   1260
taagcggaga ggcagagatc ctgagatggg cggcaagccc agacggaaga atcctcaaga   1320
gggcctgtat aatgagctgc agaaagacaa gatggccgag gcctacagcg agatcggaat   1380
gaagggcgag cgcagaagag gcaagggaca cgatggactg taccagggcc tgagcacagc   1440
caccaaggat acctatgatg ccctgcacat gcaggccctg cctccaagat gagggcccgt   1500
ttaaacccgc tggctcgctt tcttgctgtc caatttctat taaaggttcc tttgttccgt   1560
aagtccaact actaaactgg gggatattat gaagggcctt gagcatctgg attctgccta   1620
ataaaaaaca tttattttca ttgc                                          1644

<210> SEQ ID NO 47
<211> LENGTH: 1644
<212> TYPE: DNA
<213> ORGANISM: Artificial Sequence
<220> FEATURE:
<223> OTHER INFORMATION: Synthetic Polynucleotide

<400> SEQUENCE: 47
```

```
gggagaccca agctggctag cctcgcagtt cggcggtccc gcgggtctgt ctgttgcttc    60
aacagtgttt ggacggaaca gatccgggga ctctcttcca gccatggcac tgcctgttac   120
agctctgctg ctgcctctgg cactgctgct tcatgccgcc agacctgata taactcac    180 acaatcacct tcttctctta gcgcatcagt cggggatcgg gttaccatta cttgtcgcgc   240
atcacagtcc gtaacgatac tcgggtccca tctgatccat tggtatcagc aaaaaccagg   300
caaagcaccc aagctcttga tccaattggc aagcaacgtg caaactggag tcccttctcg   360
gttttccgga agtggctctg cactgactt tacgttgacc attagtagcc tccaacctga    420
ggatgttgcc acttattatt gtcttcagtc cagaaccatt ccgcgcacat cggacaggg    480 tactaagttg gaaataaagg gctcaacgtc aggctctggt aagccgggta gcggggaggg   540
atcaaccaaa ggtcaagttc agctggtaca aagtggtggt ggacttgtgc aacctggcag   600
gtctgtgaaa ctctcctgtg ccgctagcgg gtacactttt actgactaca gtataaactg   660
ggtgagacaa gctccaggca aaggactcga atggggttggg tggataaata cagagactag   720
agagccggcc tacgcatacg acttcagggg aaggttcacc atcagtcggg acacttcaaa   780
gaatacggcg taccttcaaa tgaatagttt gagagcagag gacacagctg tgtattattg   840
tgcgcgcgac tactcctatg ctatggacta ctgggggcaa ggaaccttgg tgactgtcag   900
tagctttgtg cctgtgttcc tgcctgccaa gcctaccaca acaccagctc ctagacctcc   960
aactcctgct cctacaatcg cctctcagcc actgtctctg aggcctgaag cttgtagacc  1020
tgctgctggc ggagccgtgc ataccagagg actggatttc gcctgcgaca tctacatctg  1080
ggctcctctg gctggaacat gtggcgtgct gctgctgagc ctggtcatca ccctgtactg  1140
caaccaccgg aacagagtga agttcagcag atccgccgat gctcctgcct accagcaggg  1200
acagaaccag ctgtacaacg agctgaacct ggggagaaga gaagagtacg acgtgctgga  1260
taagcggaga ggcagagatc ctgagatggg cggcaagccc agacggaaga tcctcaaga  1320 gggcctgtat aatgagctgc agaaagacaa gatggccgag gcctacagcg agatcggaat  1380
gaagggcgag cgcagaagag caagggaca cgatggactg taccagggcc tgagcacagc  1440
caccaaggat acctatgatg ccctgcacat gcaggccctg cctccaagat gagggcccgt  1500
ttaaacccgc tggctcgctt tcttgctgtc caatttctat taaaggttcc tttgttccgt  1560
aagtccaact actaaactgg gggatattat gaagggcctt gagcatctgg attctgccta  1620
ataaaaaaca tttatttca ttgc                                          1644
```

<210> SEQ ID NO 48
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 48

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp

Pro Val Glu Glu Asp Val Ala Val Tyr Tyr Cys Leu Gln Ser Arg
65                  70                  75                  80

Thr Ile Pro Arg Thr Phe Gly Gly Thr Lys Leu Glu Ile Lys Gly
            85                  90                  95

Ser Thr Ser Gly Ser Gly Lys Pro Gly Ser Gly Glu Gly Ser Thr Lys
            100                 105                 110

Gly Gln Ile Gln Leu Val Gln Ser Gly Pro Glu Leu Lys Lys Pro Gly
        115                 120                 125

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

Cys Ala Leu Asp Tyr Ser Tyr Ala Met Asp Tyr Trp Gly Gln Gly Thr
225                 230                 235                 240

Ser Val Thr Val Ser Ser
                245

<210> SEQ ID NO 49
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 49

Asp Ile Val Met Thr Gln Ser Pro Asp Ser Leu Ser Val Ser Leu Gly
1               5                   10                  15

Glu Arg Ala Thr Ile Asn Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Lys Leu Leu Ile Gln Leu Ala Ser Asn Val Gln Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Leu Gln Ser Arg
                85                  90                  95

Thr Ile Pro Arg Thr Phe Gly Gly Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Ala Glu Val Lys Lys Pro Gly
    130                 135                 140

Ala Ser Val Lys Ile Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp

```
                180                 185                 190
Phe Arg Gly Arg Val Thr Met Thr Arg Asp Thr Ser Ala Ser Thr Ala
            195                 200                 205

Tyr Leu Gln Ile Ser Ser Leu Lys Ala Glu Asp Thr Ala Val Tyr Phe
            210                 215                 220

Cys Ala Leu Asp Tyr Ser Tyr Ala Met Asp Tyr Trp Gly Gln Gly Ser
225                 230                 235                 240

Leu Val Thr Val Ser Ser
                245

<210> SEQ ID NO 50
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 50

Asp Ile Val Leu Thr Gln Ser Pro Ala Ser Leu Ala Val Ser Leu Gly
1               5                   10                  15

Glu Arg Ala Thr Ile Ser Cys Arg Ala Ser Glu Ser Val Ser Ile Leu
            20                  25                  30

Gly Ser His Leu Leu His Trp Tyr Gln Gln Lys Pro Gly Gln Pro Pro
        35                  40                  45

Lys Leu Leu Ile Tyr Leu Ala Ser Asn Leu Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Ala Glu Asp Val Ala Val Tyr Tyr Cys Leu Gln Ser Arg
                85                  90                  95

Thr Ile Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Ala Glu Val Lys Lys Pro Gly
    130                 135                 140

Ala Ser Val Lys Ile Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Val Thr Met Thr Arg Asp Thr Ser Ala Ser Thr Ala
        195                 200                 205

Tyr Leu Gln Ile Ser Ser Leu Lys Ala Glu Asp Thr Ala Val Tyr Phe
    210                 215                 220

Cys Ala Leu Asp Tyr Ser Tyr Ala Met Asp Tyr Trp Gly Gln Gly Ser
225                 230                 235                 240

Leu Val Thr Val Ser Ser
                245

<210> SEQ ID NO 51
<211> LENGTH: 246
<212> TYPE: PRT
<213> ORGANISM: Artificial Sequence
<220> FEATURE:
<223> OTHER INFORMATION: Synthetic Polypeptide
```

```
<400> SEQUENCE: 51

Asp Ile Val Leu Thr Gln Ser Pro Ala Ser Leu Ala Val Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Lys Leu Leu Ile Tyr Leu Ala Ser Asn Val Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Ala Glu Asp Val Ala Val Tyr Tyr Cys Leu Gln Ser Arg
                85                  90                  95

Thr Ile Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Val Gln Leu Val Gln Ser Gly Ala Glu Val Lys Lys Pro Gly
130                 135                 140

Ala Ser Val Lys Ile Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Val Thr Met Thr Arg Asp Thr Ser Ala Ser Thr Ala
        195                 200                 205

Tyr Leu Gln Ile Ser Ser Leu Lys Ala Glu Asp Thr Ala Val Tyr Phe
    210                 215                 220

Cys Ala Leu Asp Tyr Ser Tyr Ala Met Asp Tyr Trp Gly Gln Gly Ser
225                 230                 235                 240

Leu Val Thr Val Ser Ser
                245

<210> SEQ ID NO 52
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 52

Asp Ile Val Met Thr Gln Ser Pro Asp Ser Leu Ser Val Ser Leu Gly
1               5                   10                  15

Glu Arg Ala Thr Ile Asn Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Lys Leu Leu Ile Gln Leu Ala Ser Asn Val Gln Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Leu Gln Ser Arg
                85                  90                  95
```

```
Thr Ile Pro Arg Thr Phe Gly Gly Gly Thr Lys Val Glu Ile Lys Gly
                100                 105                 110

Ser Thr Ser Gly Ser Gly Lys Pro Gly Ser Gly Glu Gly Ser Thr Lys
            115                 120                 125

Gly Gln Ile Gln Leu Val Gln Ser Gly Ala Glu Val Lys Lys Pro Gly
        130                 135                 140

Glu Ser Val Lys Ile Ser Cys Lys Ala Ser Gly Tyr Thr Phe Thr Asp
145                 150                 155                 160

Tyr Ser Ile Asn Trp Val Arg Gln Ala Pro Gly Gln Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Asp Thr Ser Ala Ser Thr Ala
        195                 200                 205

Tyr Leu Gln Ile Ser Ser Leu Lys Ala Glu Asp Thr Ala Val Tyr Phe
210                 215                 220

Cys Ala Leu Asp Tyr Ser Tyr Ala Met Asp Tyr Trp Gly Gln Gly Thr
225                 230                 235                 240

Leu Val Thr Val Ser Ser
                245

<210> SEQ ID NO 53
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 53

Asp Ile Val Leu Thr Gln Ser Pro Ala Ser Leu Ala Val Ser Leu Gly
1               5                   10                  15

Glu Arg Ala Thr Ile Ser Cys Arg Ala Ser Glu Ser Val Ser Ile Leu
            20                  25                  30

Gly Ser His Tyr Leu Ala Trp Tyr Gln Gln Lys Pro Gly Gln Pro Pro
        35                  40                  45

Lys Leu Leu Ile Tyr Leu Ala Ser Asn Leu Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Ala Glu Asp Val Ala Val Tyr Tyr Cys Gln Gln Ser Arg
                85                  90                  95

Thr Ile Pro Arg Thr Phe Gly Gln Gly Thr Lys Leu Glu Ile Lys Gly
                100                 105                 110

Ser Thr Ser Gly Ser Gly Lys Pro Gly Ser Gly Glu Gly Ser Thr Lys
            115                 120                 125

Gly Gln Ile Gln Leu Val Gln Ser Gly Ala Glu Val Lys Lys Pro Gly
        130                 135                 140

Glu Ser Val Lys Ile Ser Cys Lys Ala Ser Gly Tyr Thr Phe Thr Asp
145                 150                 155                 160

Tyr Ser Ile Asn Trp Val Arg Gln Ala Pro Gly Gln Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Asp Thr Ser Ala Ser Thr Ala
        195                 200                 205
```

```
Tyr Leu Gln Ile Ser Ser Leu Lys Ala Glu Asp Thr Ala Val Tyr Phe
    210                 215                 220

Cys Ala Leu Asp Tyr Ser Tyr Ala Met Asp Tyr Trp Gly Gln Gly Thr
225                 230                 235                 240

Leu Val Thr Val Ser Ser
                245

<210> SEQ ID NO 54
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 54

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Ala Pro
        35                  40                  45

Lys Leu Leu Ile Gln Leu Ala Ser Asn Val Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
130                 135                 140

Gly Ser Val Lys Ile Ser Cys Ala Ala Ser Gly Tyr Thr Phe Thr Asp
145                 150                 155                 160

Tyr Ser Ile Asn Trp Val Lys Gln Ala Pro Gly Lys Gly Leu Glu Trp
                165                 170                 175

Val Gly Trp Ile Asn Thr Glu Thr Arg Glu Pro Ala Tyr Ala Tyr Asp
            180                 185                 190

Phe Arg Gly Arg Phe Thr Phe Ser Leu Asp Thr Ser Lys Ser Thr Ala
        195                 200                 205

Tyr Leu Gln Met Asn Ser Leu Arg Ala Glu Asp Thr Ala Val Tyr Tyr
    210                 215                 220

Cys Ala Leu Asp Tyr Ser Tyr Ala Met Asp Tyr Trp Gly Gln Gly Thr
225                 230                 235                 240

Leu Val Thr Val Ser Ser
                245

<210> SEQ ID NO 55
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 55

Asp Ile Gln Leu Thr Gln Ser Pro Ser Ser Leu Ser Ala Ser Val Gly
1               5                   10                  15
```

```
Asp Arg Val Thr Ile Thr Cys Arg Ala Ser Gln Ser Val Thr Ile Leu
            20                  25                  30

Gly Ser His Leu Ile His Trp Tyr Gln Gln Lys Pro Gly Lys Ala Pro
        35                  40                  45

Lys Leu Leu Ile Gln Leu Ala Ser Asn Val Gln Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Leu Gln Ser Arg
                85                  90                  95

Thr Ile Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Val Gln Leu Val Gln Ser Gly Gly Gly Leu Val Gln Pro Gly
130                 135                 140

Arg Ser Val Lys Leu Ser Cys Ala Ala Ser Gly Tyr Thr Phe Thr Asp
145                 150                 155                 160

Tyr Ser Ile Asn Trp Val Arg Gln Ala Pro Gly Lys Gly Leu Glu Trp
                165                 170                 175

Val Gly Trp Ile Asn Thr Glu Thr Arg Glu Pro Ala Tyr Ala Tyr Asp
            180                 185                 190

Phe Arg Gly Arg Phe Thr Ile Ser Arg Asp Thr Ser Lys Asn Thr Ala
        195                 200                 205

Tyr Leu Gln Met Asn Ser Leu Arg Ala Glu Asp Thr Ala Val Tyr Tyr
    210                 215                 220

Cys Ala Arg Asp Tyr Ser Tyr Ala Met Asp Tyr Trp Gly Gln Gly Thr
225                 230                 235                 240

Leu Val Thr Val Ser Ser
                245

<210> SEQ ID NO 56
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 56

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Ala Pro
        35                  40                  45

Lys Leu Leu Ile Gln Leu Ala Ser Asn Val Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Val Ala Val Tyr Tyr Cys Leu Gln Ser Arg
                85                  90                  95

Thr Ile Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125
```

-continued

Gly Gln Ile Gln Leu Val Gln Ser Gly Pro Glu Leu Lys Lys Pro Gly
            130                 135                 140

Gly Ser Val Lys Ile Ser Cys Ala Ala Ser Gly Tyr Thr Phe Thr Asp
145                 150                 155                 160

Tyr Ser Ile Asn Trp Val Lys Gln Ala Pro Gly Lys Gly Leu Glu Trp
                165                 170                 175

Val Gly Trp Ile Asn Thr Glu Thr Arg Glu Pro Ala Tyr Ala Tyr Asp
            180                 185                 190

Phe Arg Gly Arg Phe Thr Phe Ser Ala Asp Thr Ser Lys Ser Thr Ala
            195                 200                 205

Tyr Leu Gln Met Asn Ser Leu Arg Ala Glu Asp Thr Ala Val Tyr Tyr
            210                 215                 220

Cys Ala Leu Asp Tyr Ser Tyr Ala Met Asp Tyr Trp Gly Gln Gly Thr
225                 230                 235                 240

Leu Val Thr Val Ser Ser
                245

<210> SEQ ID NO 57
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 57

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Ala Pro
        35                  40                  45

Lys Leu Leu Ile Gln Leu Ala Ser Asn Val Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Val Ala Val Tyr Tyr Cys Leu Gln Ser Arg
                85                  90                  95

Thr Ile Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Gly Ser Val Lys Ile Ser Cys Ala Ala Ser Gly Tyr Thr Phe Thr Asp
145                 150                 155                 160

Tyr Ser Ile Asn Trp Val Arg Gln Ala Pro Gly Lys Gly Leu Glu Trp
                165                 170                 175

Val Gly Trp Ile Asn Thr Glu Thr Arg Glu Pro Ala Tyr Ala Tyr Asp
            180                 185                 190

Phe Arg Gly Arg Phe Thr Phe Ser Ala Asp Thr Ser Lys Ser Thr Ala
        195                 200                 205

Tyr Leu Gln Met Asn Ser Leu Arg Ala Glu Asp Thr Ala Val Tyr Tyr
    210                 215                 220

Cys Ala Leu Asp Tyr Ser Tyr Ala Met Asp Tyr Trp Gly Gln Gly Thr
225                 230                 235                 240

Leu Val Thr Val Ser Ser
            245

<210> SEQ ID NO 58
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 58

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Ala Pro
        35                  40                  45

Lys Leu Leu Ile Gln Leu Ala Ser Asn Val Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Val Ala Val Tyr Tyr Cys Leu Gln Ser Arg
                85                  90                  95

Thr Ile Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Glu Ser Gly Ala Glu Val Lys Lys Pro Gly
    130                 135                 140

Gly Ser Val Lys Ile Ser Cys Ala Ala Ser Gly Tyr Thr Phe Thr Asp
145                 150                 155                 160

Tyr Ser Ile Asn Trp Val Lys Gln Ala Pro Gly Lys Gly Leu Glu Trp
                165                 170                 175

Val Gly Trp Ile Asn Thr Glu Thr Arg Glu Pro Ala Tyr Ala Tyr Asp
            180                 185                 190

Phe Arg Gly Arg Phe Thr Phe Ser Leu Asp Thr Ser Lys Ser Thr Ala
        195                 200                 205

Tyr Leu Gln Met Asn Ser Leu Arg Ala Glu Asp Thr Ala Val Tyr Tyr
    210                 215                 220

Cys Ala Leu Asp Tyr Ser Tyr Ala Met Asp Tyr Trp Gly Gln Gly Thr
225                 230                 235                 240

Leu Val Thr Val Ser Ser
            245

<210> SEQ ID NO 59
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 59

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Ala Pro

-continued

```
                35                  40                  45
Lys Leu Leu Ile Gln Leu Ala Ser Asn Val Gln Thr Gly Val Pro Ala
 50                  55                  60
Arg Phe Ser Gly Ser Gly Ser Gly Thr Asp Phe Thr Leu Thr Ile Ser
 65                  70                  75                  80
Ser Val Glu Pro Glu Asp Val Ala Val Tyr Tyr Cys Leu Gln Ser Arg
                 85                  90                  95
Thr Ile Pro Arg Thr Phe Gly Gln Gly Thr Lys Val Glu Ile Lys Gly
            100                 105                 110
Ser Thr Ser Gly Ser Gly Lys Pro Gly Ser Gly Glu Gly Ser Thr Lys
        115                 120                 125
Gly Gln Ile Gln Leu Val Glu Ser Gly Ala Glu Val Lys Lys Pro Gly
130                 135                 140
Gly Ser Val Lys Val Ser Cys Lys Ala Ser Gly Tyr Thr Phe Thr Asp
145                 150                 155                 160
Tyr Ser Ile Asn Trp Val Arg Gln Ala Pro Gly Lys Gly Leu Glu Trp
                165                 170                 175
Val Gly Trp Ile Asn Thr Glu Thr Arg Glu Pro Ala Tyr Ala Tyr Asp
            180                 185                 190
Phe Arg Gly Arg Phe Ala Ile Ser Ala Glu Thr Ser Lys Ser Thr Ala
        195                 200                 205
Tyr Leu Gln Met Asn Ser Leu Arg Ala Glu Asp Thr Ala Val Tyr Tyr
210                 215                 220
Cys Ala Leu Asp Tyr Ser Tyr Ala Met Asp Tyr Trp Gly Gln Gly Thr
225                 230                 235                 240
Leu Val Thr Val Ser Ser
                245

<210> SEQ ID NO 60
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 60

Asp Ile Val Leu Thr Gln Ser Pro Ala Ser Leu Ala Val Ser Pro Gly
  1               5                  10                  15
Gln Arg Ala Thr Ile Thr Cys Arg Ala Ser Glu Ser Val Thr Ile Leu
             20                  25                  30
Gly Ser His Leu Ile His Trp Tyr Gln Gln Lys Pro Gly Gln Pro Pro
         35                  40                  45
Lys Leu Leu Ile Gln Leu Ala Ser Asn Val Gln Thr Gly Val Pro Ala
 50                  55                  60
Arg Phe Ser Gly Ser Gly Ser Gly Thr Asp Phe Thr Leu Thr Ile Ser
 65                  70                  75                  80
Ser Val Glu Pro Glu Asp Thr Ala Asn Tyr Tyr Cys Leu Gln Ser Arg
                 85                  90                  95
Thr Ile Pro Arg Thr Phe Gly Gln Gly Thr Lys Val Glu Ile Lys Gly
            100                 105                 110
Ser Thr Ser Gly Ser Gly Lys Pro Gly Ser Gly Glu Gly Ser Thr Lys
        115                 120                 125
Gly Gln Ile Gln Leu Val Gln Ser Gly Pro Glu Leu Lys Lys Pro Gly
130                 135                 140
Gly Ser Val Lys Ile Ser Cys Lys Ala Ser Gly Tyr Thr Phe Thr Asp
```

```
145                 150                 155                 160

Tyr Ser Ile Asn Trp Val Arg Gln Ala Pro Gly Lys Gly Leu Glu Trp
                165                 170                 175

Val Gly Trp Ile Asn Thr Glu Thr Arg Glu Pro Ala Tyr Ala Tyr Asp
                180                 185                 190

Phe Thr Gly Arg Phe Thr Phe Ser Ala Asp Thr Ser Lys Ser Met Ala
                195                 200                 205

Tyr Leu Gln Ile Asn Ser Leu Arg Ala Glu Asp Thr Ala Val Tyr Tyr
                210                 215                 220

Cys Ala Leu Asp Tyr Ser Tyr Ala Met Asp Tyr Trp Gly Gln Gly Thr
225                 230                 235                 240

Leu Val Thr Val Ser Ser
                245

<210> SEQ ID NO 61
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 61

Asp Ile Val Leu Thr Gln Ser Pro Ala Ser Leu Ala Val Ser Pro Gly
1               5                   10                  15

Gln Arg Ala Thr Ile Ser Cys Arg Ala Ser Glu Ser Val Thr Ile Leu
                20                  25                  30

Gly Ser His Leu Ile His Trp Tyr Gln Gln Lys Pro Gly Gln Pro Pro
            35                  40                  45

Lys Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Val Ala Val Tyr Tyr Cys Leu Gln Ser Arg
                85                  90                  95

Thr Ile Pro Arg Thr Phe Gly Gln Gly Thr Lys Val Glu Ile Lys Gly
                100                 105                 110

Ser Thr Ser Gly Ser Gly Lys Pro Gly Ser Gly Glu Gly Ser Thr Lys
            115                 120                 125

Gly Gln Ile Thr Leu Lys Glu Ser Gly Pro Thr Leu Val Lys Pro Thr
        130                 135                 140

Gln Thr Leu Thr Leu Ser Cys Lys Ala Ser Gly Tyr Thr Phe Thr Asp
145                 150                 155                 160

Tyr Ser Ile Asn Trp Val Arg Arg Ala Pro Gly Lys Gly Leu Glu Trp
                165                 170                 175

Met Gly Trp Ile Asn Thr Glu Thr Arg Glu Pro Ala Tyr Ala Tyr Asp
                180                 185                 190

Phe Arg Gly Arg Phe Val Phe Ser Leu Asp Thr Ser Val Ser Met Ala
                195                 200                 205

Tyr Leu Gln Ile Ser Ser Leu Lys Ala Glu Asp Thr Ala Val Tyr Tyr
                210                 215                 220

Cys Ala Leu Asp Tyr Ser Tyr Ala Met Asp Tyr Trp Gly Gln Gly Thr
225                 230                 235                 240

Leu Val Thr Val Ser Ser
                245
```

```
<210> SEQ ID NO 62
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 62

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Ala Pro
        35                  40                  45

Lys Leu Leu Ile Gln Leu Ala Ser Asn Val Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Val Ala Val Tyr Tyr Cys Leu Gln Ser Arg
                85                  90                  95

Thr Ile Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Gly Ser Val Lys Ile Ser Cys Ala Ala Ser Gly Tyr Thr Phe Thr Ser
145                 150                 155                 160

Tyr Asp Ile Asn Trp Val Arg Gln Ala Pro Gly Lys Gly Leu Glu Trp
                165                 170                 175

Val Gly Trp Ile Asn Thr Glu Thr Arg Glu Pro Ala Tyr Ala Tyr Asp
            180                 185                 190

Phe Arg Gly Arg Phe Thr Phe Ser Ala Asp Thr Ser Lys Ser Thr Ala
        195                 200                 205

Tyr Leu Gln Met Asn Ser Leu Arg Ala Glu Asp Thr Ala Val Tyr Tyr
    210                 215                 220

Cys Ala Leu Asp Tyr Ser Tyr Ala Met Asp Tyr Trp Gly Gln Gly Thr
225                 230                 235                 240

Leu Val Thr Val Ser Ser
                245

<210> SEQ ID NO 63
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 63

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Ala Pro
        35                  40                  45

Lys Leu Leu Ile Gln Leu Ala Ser Asn Val Gln Thr Gly Val Pro Ala
    50                  55                  60
```

```
Arg Phe Ser Gly Ser Gly Ser Gly Thr Asp Phe Thr Leu Thr Ile Ser
 65                  70                  75                  80

Ser Val Glu Pro Glu Asp Val Ala Val Tyr Tyr Cys Leu Gln Ser Arg
                 85                  90                  95

Thr Ile Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Gly Ser Val Lys Ile Ser Cys Ala Ala Ser Gly Tyr Thr Phe Thr Asp
145                 150                 155                 160

Tyr Ser Ile Asn Trp Val Arg Gln Ala Pro Gly Lys Gly Leu Glu Trp
                165                 170                 175

Val Gly Trp Ile Asn Thr Glu Thr Arg Glu Pro Ala Tyr Ala Tyr Asp
            180                 185                 190

Phe Arg Gly Arg Phe Thr Phe Ser Ala Asp Thr Ser Lys Ser Thr Ala
        195                 200                 205

Tyr Leu Gln Met Asn Ser Leu Arg Ala Glu Asp Thr Ala Val Tyr Tyr
    210                 215                 220

Cys Ala Leu Asp Tyr Thr Tyr Gly Met Asp Tyr Trp Gly Gln Gly Thr
225                 230                 235                 240

Leu Val Thr Val Ser Ser
                245
```

<210> SEQ ID NO 64
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 64

```
Asp Ile Val Leu Thr Gln Ser Pro Ser Ser Leu Ser Ala Ser Val Gly
  1               5                  10                  15

Asp Arg Ala Thr Ile Ser Cys Arg Ala Ser Glu Ser Val Ser Phe Leu
             20                  25                  30

Gly Ile Asn Leu Ile His Trp Tyr Gln Gln Lys Pro Gly Gln Ala Pro
         35                  40                  45

Lys Leu Leu Ile Tyr Ser Ala Ser Asn Leu Gln Ser Gly Val Pro Ala
 50                  55                  60

Arg Phe Ser Gly Ser Gly Ser Gly Thr Asp Phe Thr Leu Thr Ile Ser
 65                  70                  75                  80

Ser Val Glu Pro Glu Asp Val Ala Val Tyr Tyr Cys Leu Gln Ser Arg
                 85                  90                  95

Thr Leu Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Gly Ser Val Lys Ile Ser Cys Ala Ala Ser Gly Tyr Thr Phe Thr Asp
145                 150                 155                 160

Tyr Ser Ile Asn Trp Val Arg Gln Ala Pro Gly Lys Gly Leu Glu Trp
                165                 170                 175
```

-continued

Val Gly Trp Ile Asn Thr Glu Thr Arg Glu Pro Ala Tyr Ala Tyr Asp
                180                 185                 190

Phe Arg Gly Arg Phe Thr Phe Ser Ala Asp Thr Ser Lys Ser Thr Ala
            195                 200                 205

Tyr Leu Gln Met Asn Ser Leu Arg Ala Glu Asp Thr Ala Val Tyr Tyr
        210                 215                 220

Cys Ala Leu Asp Tyr Ser Tyr Ala Met Asp Tyr Trp Gly Gln Gly Thr
225                 230                 235                 240

Leu Val Thr Val Ser Ser
                245

<210> SEQ ID NO 65
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 65

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Ser Phe Leu
            20                  25                  30

Gly Ile Asn Leu Ile His Trp Tyr Gln Gln Lys Pro Gly Gln Ala Pro
        35                  40                  45

Lys Leu Leu Ile Tyr Ser Ala Ser Asn Leu Gln Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Val Ala Val Tyr Tyr Cys Leu Gln Ser Lys
                85                  90                  95

Asn Phe Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Gly Ser Val Lys Ile Ser Cys Ala Ala Ser Gly Tyr Thr Phe Thr Asp
145                 150                 155                 160

Tyr Ser Ile Asn Trp Val Arg Gln Ala Pro Gly Lys Gly Leu Glu Trp
                165                 170                 175

Val Gly Trp Ile Asn Thr Glu Thr Arg Glu Pro Ala Tyr Ala Tyr Asp
            180                 185                 190

Phe Arg Gly Arg Phe Thr Phe Ser Ala Asp Thr Ser Lys Ser Thr Ala
        195                 200                 205

Tyr Leu Gln Met Asn Ser Leu Arg Ala Glu Asp Thr Ala Val Tyr Tyr
    210                 215                 220

Cys Ala Leu Asp Tyr Ser Tyr Ala Met Asp Tyr Trp Gly Gln Gly Thr
225                 230                 235                 240

Leu Val Thr Val Ser Ser
                245

<210> SEQ ID NO 66
<211> LENGTH: 246
<212> TYPE: PRT
<213> ORGANISM: Artificial Sequence
<220> FEATURE:

<223> OTHER INFORMATION: Synthetic Polypeptide

<400> SEQUENCE: 66

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Ala Pro
        35                  40                  45

Lys Leu Leu Ile Gln Leu Ala Ser Asn Val Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Val Ala Val Tyr Tyr Cys Leu Gln Ser Arg
                85                  90                  95

Thr Ile Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Gly Ser Val Lys Ile Ser Cys Ala Ala Ser Gly Tyr Thr Phe Thr Ser
145                 150                 155                 160

Tyr Ser Ile Asn Trp Val Arg Gln Ala Pro Gly Lys Gly Leu Glu Trp
                165                 170                 175

Val Gly Trp Ile Asn Thr Glu Thr Arg Glu Pro Ala Tyr Ala Gln Gly
            180                 185                 190

Phe Thr Gly Arg Phe Thr Phe Ser Ala Asp Thr Ser Lys Ser Thr Ala
        195                 200                 205

Tyr Leu Gln Met Asn Ser Leu Arg Ala Glu Asp Thr Ala Val Tyr Tyr
    210                 215                 220

Cys Ala Leu Asp Tyr Leu Tyr Ser Leu Asp Phe Trp Gly Gln Gly Thr
225                 230                 235                 240

Leu Val Thr Val Ser Ser
                245

<210> SEQ ID NO 67
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 67

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Ala Pro
        35                  40                  45

Lys Leu Leu Ile Gln Leu Ala Ser Asn Val Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Val Ala Val Tyr Tyr Cys Leu Gln Ser Arg
                85                  90                  95

```
Thr Ile Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
            115                 120                 125

Gly Gln Ile Gln Leu Val Gln Ser Gly Pro Glu Leu Lys Lys Pro Gly
            130                 135                 140

Gly Ser Val Lys Ile Ser Cys Ala Ala Ser Gly Tyr Thr Phe Thr Ser
145                 150                 155                 160

Tyr Asp Ile Asn Trp Val Arg Gln Ala Pro Gly Lys Gly Leu Glu Trp
                165                 170                 175

Val Gly Trp Ile Asn Thr Asn Thr Gly Asn Pro Thr Tyr Ala Gln Gly
            180                 185                 190

Phe Thr Gly Arg Phe Thr Phe Ser Ala Asp Thr Ser Lys Ser Thr Ala
            195                 200                 205

Tyr Leu Gln Met Asn Ser Leu Arg Ala Glu Asp Thr Ala Val Tyr Tyr
            210                 215                 220

Cys Ala Leu Asp Tyr Thr Tyr Gly Met Asp Tyr Trp Gly Gln Gly Thr
225                 230                 235                 240

Leu Val Thr Val Ser Ser
                245

<210> SEQ ID NO 68
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 68

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Ala Pro
        35                  40                  45

Lys Leu Leu Ile Gln Leu Ala Ser Asn Val Gln Thr Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Val Ala Val Tyr Tyr Cys Leu Gln Ser Lys
                85                  90                  95

Asn Phe Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
            115                 120                 125

Gly Gln Ile Gln Leu Val Gln Ser Gly Pro Glu Leu Lys Lys Pro Gly
            130                 135                 140

Gly Ser Val Lys Ile Ser Cys Ala Ala Ser Gly Tyr Thr Phe Thr Ser
145                 150                 155                 160

Tyr Asp Ile Asn Trp Val Arg Gln Ala Pro Gly Lys Gly Leu Glu Trp
                165                 170                 175

Val Gly Trp Ile Asn Thr Glu Thr Arg Glu Pro Ala Tyr Ala Tyr Asp
            180                 185                 190

Phe Arg Gly Arg Phe Thr Phe Ser Ala Asp Thr Ser Lys Ser Thr Ala
            195                 200                 205
```

```
Tyr Leu Gln Met Asn Ser Leu Arg Ala Glu Asp Thr Ala Val Tyr Tyr
            210                 215                 220

Cys Ala Leu Asp Tyr Leu Tyr Ser Leu Asp Phe Trp Gly Gln Gly Thr
225                 230                 235                 240

Leu Val Thr Val Ser Ser
                245

<210> SEQ ID NO 69
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 69

Asp Ile Val Leu Thr Gln Ser Pro Ser Ser Leu Ser Ala Ser Val Gly
1               5                   10                  15

Asp Arg Ala Thr Ile Ser Cys Arg Ala Ser Glu Ser Val Ser Phe Leu
            20                  25                  30

Gly Ile Asn Leu Ile His Trp Tyr Gln Gln Lys Pro Gly Gln Ala Pro
        35                  40                  45

Lys Leu Leu Ile Tyr Leu Ala Ser Asn Leu Glu Thr Gly Val Pro Ala
50                  55                  60

Arg Phe Ser Gly Ser Gly Ser Gly Thr Asp Phe Thr Leu Thr Ile Ser
65                  70                  75                  80

Ser Val Glu Pro Glu Asp Val Ala Val Tyr Tyr Cys Leu Gln Ser Arg
                85                  90                  95

Thr Leu Pro Arg Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
130                 135                 140

Gly Ser Val Lys Ile Ser Cys Ala Ala Ser Gly Tyr Thr Phe Thr Ser
145                 150                 155                 160

Tyr Ser Ile Asn Trp Val Arg Gln Ala Pro Gly Lys Gly Leu Glu Trp
                165                 170                 175

Val Gly Trp Ile Asn Thr Glu Thr Arg Glu Pro Ala Tyr Ala Gln Gly
            180                 185                 190

Phe Thr Gly Arg Phe Thr Phe Ser Ala Asp Thr Ser Lys Ser Thr Ala
        195                 200                 205

Tyr Leu Gln Met Asn Ser Leu Arg Ala Glu Asp Thr Ala Val Tyr Tyr
210                 215                 220

Cys Ala Leu Asp Tyr Leu Tyr Ser Leu Asp Phe Trp Gly Gln Gly Thr
225                 230                 235                 240

Leu Val Thr Val Ser Ser
                245

<210> SEQ ID NO 70
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 70

Asp Ile Val Leu Thr Gln Ser Pro Ser Ser Leu Ser Ala Ser Val Gly
```

-continued

```
                1               5                  10                 15
            Asp Arg Ala Thr Ile Ser Cys Arg Ala Ser Glu Ser Val Thr Ile Leu
                            20                 25                 30

Gly Ser His Leu Ile His Trp Tyr Gln Gln Lys Pro Gly Gln Ala Pro
                            35                 40                 45

Lys Leu Leu Ile Asn Leu Ala Ser Asn Val Asn Thr Gly Val Pro Ala
                            50                 55                 60

Arg Phe Ser Gly Ser Gly Ser Gly Thr Asp Phe Thr Leu Thr Ile Ser
             65                 70                 75                 80

Ser Val Glu Pro Glu Asp Val Ala Val Tyr Tyr Cys Leu Gln Ser Arg
                            85                 90                 95

Thr Ile Pro Arg Thr Phe Gly Gln Gly Thr Lys Val Glu Ile Lys Gly
                           100                105                110

Ser Thr Ser Gly Ser Gly Lys Pro Gly Ser Gly Glu Gly Ser Thr Lys
                           115                120                125

Gly Gln Ile Gln Leu Val Gln Ser Gly Pro Glu Leu Lys Lys Pro Gly
                130                135                140

Gly Ser Val Lys Ile Ser Cys Ala Ala Ser Gly Tyr Thr Phe Thr Asp
            145                150                155                160

Tyr Ser Ile Asn Trp Val Arg Gln Ala Pro Gly Lys Gly Leu Glu Trp
                           165                170                175

Val Gly Trp Ile Asn Thr Glu Thr Arg Glu Pro Ala Tyr Ala Tyr Asp
                           180                185                190

Phe Arg Gly Arg Phe Thr Phe Ser Ala Asp Thr Ser Lys Ser Thr Ala
                           195                200                205

Tyr Leu Gln Met Asn Ser Leu Arg Ala Glu Asp Thr Ala Val Tyr Tyr
                           210                215                220

Cys Ala Leu Asp Tyr Ser Tyr Ala Met Asp Tyr Trp Gly Gln Gly Thr
            225                230                235                240

Leu Val Thr Val Ser Ser
                           245

<210> SEQ ID NO 71
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 71

Asp Ile Val Leu Thr Gln Ser Pro Ser Ser Leu Ser Ala Ser Val Gly
             1               5                  10                 15

Asp Arg Ala Thr Ile Ser Cys Arg Ala Ser Glu Ser Val Thr Ile Leu
                            20                 25                 30

Gly Ser His Leu Ile His Trp Tyr Gln Gln Lys Pro Gly Gln Ala Pro
                            35                 40                 45

Lys Leu Leu Ile Gln Leu Ala Ser Asn Val Gln Thr Gly Val Pro Ala
                            50                 55                 60

Arg Phe Ser Gly Ser Gly Ser Gly Thr Asp Phe Thr Leu Thr Ile Ser
             65                 70                 75                 80

Ser Val Glu Pro Glu Asp Val Ala Val Tyr Tyr Cys Leu Gln Ser Arg
                            85                 90                 95

Thr Leu Pro Arg Thr Phe Gly Gln Gly Thr Lys Val Glu Ile Lys Gly
                           100                105                110

Ser Thr Ser Gly Ser Gly Lys Pro Gly Ser Gly Glu Gly Ser Thr Lys
```

```
            115                 120                 125
Gly Gln Ile Gln Leu Val Gln Ser Gly Pro Glu Leu Lys Lys Pro Gly
            130                 135                 140
Gly Ser Val Lys Ile Ser Cys Ala Ala Ser Gly Tyr Thr Phe Thr Asp
145                 150                 155                 160
Tyr Ser Ile Asn Trp Val Arg Gln Ala Pro Gly Lys Gly Leu Glu Trp
                165                 170                 175
Val Gly Trp Ile Asn Thr Glu Thr Arg Glu Pro Ala Tyr Ala Tyr Asp
            180                 185                 190
Phe Arg Gly Arg Phe Thr Phe Ser Ala Asp Thr Ser Lys Ser Thr Ala
        195                 200                 205
Tyr Leu Gln Met Asn Ser Leu Arg Ala Glu Asp Thr Ala Val Tyr Tyr
    210                 215                 220
Cys Ala Leu Asp Tyr Ser Tyr Ala Met Asp Tyr Trp Gly Gln Gly Thr
225                 230                 235                 240
Leu Val Thr Val Ser Ser
                245

<210> SEQ ID NO 72
<211> LENGTH: 246
<212> TYPE: PRT
<213> ORGANISM: Artificial Sequence
<220> FEATURE:
<223> OTHER INFORMATION: Synthetic Polypeptide

<400> SEQUENCE: 72

Asp Ile Val Leu Thr Gln Ser Pro Ser Ser Leu Ser Ala Ser Val Gly
1               5                   10                  15
Asp Arg Ala Thr Ile Ser Cys Arg Ala Ser Glu Ser Val Thr Ile Leu
            20                  25                  30
Gly Ser His Leu Ile His Trp Tyr Gln Gln Lys Pro Gly Gln Ala Pro
        35                  40                  45
Lys Leu Leu Ile Gln Leu Ala Ser Asn Val Gln Thr Gly Val Pro Ala
    50                  55                  60
Arg Phe Ser Gly Ser Gly Ser Gly Thr Asp Phe Thr Leu Thr Ile Ser
65                  70                  75                  80
Ser Val Glu Pro Glu Asp Val Ala Val Tyr Tyr Cys Leu Gln Ser Arg
                85                  90                  95
Thr Leu Pro Arg Thr Phe Gly Gln Gly Thr Lys Val Glu Ile Lys Gly
            100                 105                 110
Ser Thr Ser Gly Ser Gly Lys Pro Gly Ser Gly Glu Gly Ser Thr Lys
        115                 120                 125
Gly Gln Ile Gln Leu Val Gln Ser Gly Pro Glu Leu Lys Lys Pro Gly
    130                 135                 140
Gly Ser Val Lys Ile Ser Cys Ala Ala Ser Gly Tyr Thr Phe Thr Asp
145                 150                 155                 160
Tyr Ser Ile Asn Trp Val Arg Gln Ala Pro Gly Lys Gly Leu Glu Trp
                165                 170                 175
Val Gly Trp Ile Asn Thr Glu Thr Arg Glu Pro Ala Tyr Ala Tyr Asp
            180                 185                 190
Phe Arg Gly Arg Phe Thr Phe Ser Ala Asp Thr Ser Lys Ser Thr Ala
        195                 200                 205
Tyr Leu Gln Met Asn Ser Leu Arg Ala Glu Asp Thr Ala Val Tyr Tyr
    210                 215                 220
Cys Ala Leu Asp Tyr Ser Tyr Ala Met Asp Tyr Trp Gly Gln Gly Thr
```

```
                  225                 230                 235                 240

Leu Val Thr Val Ser Ser
                245

<210> SEQ ID NO 73
<211> LENGTH: 103
<212> TYPE: DNA
<213> ORGANISM: Artificial Sequence
<220> FEATURE:
<223> OTHER INFORMATION: Synthetic Polynucleotide

<400> SEQUENCE: 73
gggagaccca agctggctag cctcgcagtt cggcggtccc gcgggtctgt ctgttgcttc      60
aacagtgttt ggacggaaca gatccgggga ctctcttcca gcc                      103

<210> SEQ ID NO 74
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 74
agacccaagc tggctagctc taaagaagcc cctgggagca cagctcatca cc              52

<210> SEQ ID NO 75
<211> LENGTH: 89
<212> TYPE: DNA
<213> ORGANISM: Artificial Sequence
<220> FEATURE:
<223> OTHER INFORMATION: Synthetic Polynucleotide

<400> SEQUENCE: 75
agacccaagc tggctagcag ctcctcaccc accccagccg cgactgtctc cgccgagccc      60
ccggggccag gtgtcccggg cgcgccccg                                       89

<210> SEQ ID NO 76
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 76
gtggaacact tctgaacctg catttttatc tggaactcca gaagcagaat cctttgctaa      60
ataaatcgca gcc                                                        73

<210> SEQ ID NO 77
<211> LENGTH: 137
<212> TYPE: DNA
<213> ORGANISM: Artificial Sequence
<220> FEATURE:
<223> OTHER INFORMATION: Synthetic Polynucleotide

<400> SEQUENCE: 77
agagaagcag acatcttcta gttcctcccc cactctcctc tttccggtac ctgtgagtca      60
gctaggggag ggcagctctc acccaggctg atagttcggt gacctggctt tatctactgg     120
atgagttccg ctgggag                                                   137

<210> SEQ ID NO 78
<211> LENGTH: 62
<212> TYPE: DNA
```

<213> ORGANISM: Artificial Sequence
<220> FEATURE:
<223> OTHER INFORMATION: Synthetic Polynucleotide

<400> SEQUENCE: 78

```
agacccaagc tggctagcat attgtgcttc caccactgcc aataacaaaa taactagcaa      60
cc                                                                    62
```

<210> SEQ ID NO 79
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 79

```
aaataagaga gaaaagaaga gtaagaagaa atataagagc cacc                      44
```

<210> SEQ ID NO 80
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 80

```
cgcgtccgcc ccgcgagcac agagcctcgc ctttgccgat ccgccgcccg tccacacccg      60
ccgccagctc acc                                                        73
```

<210> SEQ ID NO 81
<211> LENGTH: 126
<212> TYPE: DNA
<213> ORGANISM: Artificial Sequence
<220> FEATURE:
<223> OTHER INFORMATION: Synthetic Polynucleotide

<400> SEQUENCE: 81

```
cacattgttc tgatcatctg aagatcagct attagaagag aaagatcagt taagtccttt      60
ggacctgatc agcttgatac aagaactact gatttcaact tctttggctt aattctctcg     120
gaaacg                                                               126
```

<210> SEQ ID NO 82
<211> LENGTH: 104
<212> TYPE: DNA
<213> ORGANISM: Artificial Sequence
<220> FEATURE:
<223> OTHER INFORMATION: Synthetic Polynucleotide

<400> SEQUENCE: 82

```
gtgtctgaaa gcatttctgg agtgttttag gcctgttcac tttctcttac tcactgtcta      60
ttcacttgtc ctgttcactc gtctggaaga tctcagccag cacc                     104
```

<210> SEQ ID NO 83
<211> LENGTH: 152
<212> TYPE: DNA
<213> ORGANISM: Artificial Sequence
<220> FEATURE:
<223> OTHER INFORMATION: Synthetic Polynucleotide

<400> SEQUENCE: 83

```
gggcccgttt aaacccgctg gctcgctttc ttgctgtcca atttctatta aaggttcctt      60
tgttccgtaa gtccaactac taaactgggg gatattatga agggccttga gcatctggat     120
```

```
tctgcctaat aaaaaacatt tattttcatt gc                                   152

<210> SEQ ID NO 84
<211> LENGTH: 137
<212> TYPE: DNA
<213> ORGANISM: Artificial Sequence
<220> FEATURE:
<223> OTHER INFORMATION: Synthetic Polynucleotide

<400> SEQUENCE: 84
tgagtgcgac ggccggcaag cccccgctcc ccgggctctc gcggtcgcac gaggatgctt     60
ggcacgtacc ccgtgtacat acttcccggg cgcccagcat ggaaataaag cacccagcgc    120
tgccctgggc ccctgcg                                                   137

<210> SEQ ID NO 85
<211> LENGTH: 591
<212> TYPE: DNA
<213> ORGANISM: Artificial Sequence
<220> FEATURE:
<223> OTHER INFORMATION: Synthetic Polynucleotide

<400> SEQUENCE: 85
gcggactatg acttagttgc gttacaccct tcttgacaa aacctaactt gcgcagaaaa      60
caagatgaga ttggcatggc tttatttgtt ttttttgttt tgttttggtt tttttttttt    120
tttggcttga ctcaggattt aaaaactgga acggtgaagg tgacagcagt cggttggagc    180
gagcatcccc caaagttctc aatgtggccg aggactttga ttgcacattg ttgtttttt    240 aatagtcatt ccaaatatga gatgcgttgt tacaggaagt cccttgccat cctaaaagcc    300
accccacttc tctctaagga gaatggccca gtcctctccc aagtccacac aggggaggtg    360
atagcattgc tttcgtgtaa attatgtaat gcaaaatttt tttaatcttc gccttaatac    420 tttttttattt tgttttattt tgaatgatga gccttcgtgc ccccccttcc ccctttttg    480 tcccccaact tgagatgtat gaaggctttt ggtctccctg ggagtgggtg gaggcagcca    540
gggcttacct gtacactgac ttgagaccag ttgaataaaa gtgcacacct t             591

<210> SEQ ID NO 86
<211> LENGTH: 165
<212> TYPE: DNA
<213> ORGANISM: Artificial Sequence
<220> FEATURE:
<223> OTHER INFORMATION: Synthetic Polynucleotide

<400> SEQUENCE: 86
attacttcag gggaagagat gacaaaacga gtctttcatt cggtgtgaac ttttctcttt     60
aattttaact gatttaacac ttttttgtgaa ttaatgaaat gataaagact tttatgtgag   120
atttccttat cacagaaata aaatatctcc aaatgtttcc ttttc                    165

<210> SEQ ID NO 87
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 87
acctgagact ggtggcttct agaagcagcc attaccaact gtaccttccc ttcttgctca     60
gccaataaat atatcctctt tcactcag                                        88
```

<210> SEQ ID NO 88
<211> LENGTH: 583
<212> TYPE: DNA
<213> ORGANISM: Artificial Sequence
<220> FEATURE:
<223> OTHER INFORMATION: Synthetic Polynucleotide

<400> SEQUENCE: 88

```
tggttgtcct gcctgcaata tttgaatttt aaatctaaat ctatttatta atatttaaca      60
ttatttatat ggggaatata tttttagact catcaatcaa ataagtattt ataatagcaa     120
cttttgtgta atgaaaatga atatctatta atatatgtat tatttataat tcctatatcc     180
tgtgactgtc tcacttaatc ctttgttttc tgactaatta ggcaaggcta tgtgattaca     240
aggctttatc tcaggggcca actaggcagc caacctaagc aagatcccat gggttgtgtg     300
tttatttcac ttgatgatac aatgaacact tataagtgaa gtgatactat ccagttactg     360
ccggtttgaa aatatgcctg caatctgagc cagtgcttta atggcatgtc agacagaact     420
tgaatgtgtc aggtgaccct gatgaaaaca tagcatctca ggagatttca tgcctggtgc     480
ttccaaatat tgttgacaac tgtgactgta cccaaatgga agtaactca tttgttaaaa     540
ttatcaatat ctaatatata tgaataaagt gtaagttcac aac                      583
```

<210> SEQ ID NO 89
<211> LENGTH: 123
<212> TYPE: DNA
<213> ORGANISM: Artificial Sequence
<220> FEATURE:
<223> OTHER INFORMATION: Synthetic Polynucleotide

<400> SEQUENCE: 89

```
acacacctgc ctgatgctat caagaggctg aagaaagcgc caaatgtgct atttttttggt    60
cacttgcttt atgacgttta ttttcctgtt aaagctgaat aaataaaaac tacagtaaat    120
gta                                                                  123
```

<210> SEQ ID NO 90
<211> LENGTH: 897
<212> TYPE: DNA
<213> ORGANISM: Artificial Sequence
<220> FEATURE:
<223> OTHER INFORMATION: Synthetic Polynucleotide

<400> SEQUENCE: 90

```
cctcaagatc aaggaaagga ggatggacga acaggggcca aactggtggg aggcagaggt      60
ggtgggggca gggatgatag gccctggatg tgcccacagg gaccaagaag tgaggtttcc     120
actgtcttgc ctgccagggc ccctgttccc ccgctggcag ccaccccctc ccccatcata     180
tcctttgccc caaggctgct cagaggggcc ccggtcctgg ccccagcccc cacctccgcc     240
ccagacacac cccccagtcg agccctgcag ccaaacagag ccttcacaac cagccacaca     300
gagcctgcct cagctgctcg cacagattac ttcagggctg gaaaagtcac acagacacac     360
aaaatgtcac aatcctgtcc ctcactcaac acaaacccca aaacacagag agcctgcctc     420
agtacactca acaacctcaa agctgcatc atcacacaat cacacacaag cacagccctg     480
acaacccaca caccccaagg cacgcaccca cagccagcct cagggcccac aggggcactg     540
tcaacacagg ggtgtgccca gaggcctaca cagaagcagc gtcagtaccc tcaggatctg     600
aggtcccaac acgtgctcgc tcacacacac ggcctgttag aattcacctg tgtatctcac     660
gcatatgcac acgcacagcc ccccagtggg tctcttgagt cccgtgcaga cacacacagc     720
```

```
cacacacact gccttgccaa aaatacccg tgtctcccct gccactcacc tcactcccat    780
tccctgagcc ctgatccatg cctcagctta gactgcagag gaactactca tttatttggg    840
atccaaggcc cccaacccac agtaccgtcc ccaataaact gcagccgagc tccccac       897
```

<210> SEQ ID NO 91
<211> LENGTH: 97
<212> TYPE: DNA
<213> ORGANISM: Artificial Sequence
<220> FEATURE:
<223> OTHER INFORMATION: Synthetic Polynucleotide

<400> SEQUENCE: 91

```
gaagtctgtt cctgtcctcc ctgtgcaggg tatcctgtag ggtgacctgg aattcgaatt    60
ctgtttccct tgtaaaatat ttgtctgtct ctttttt                            97
```

<210> SEQ ID NO 92
<211> LENGTH: 218
<212> TYPE: DNA
<213> ORGANISM: Artificial Sequence
<220> FEATURE:
<223> OTHER INFORMATION: Synthetic Polynucleotide

<400> SEQUENCE: 92

```
ctatgaagaa ggaaggcatc cagaccagaa accgaaaaat gtctagcaaa tccaaaaagt    60 gcaaaaagt gcatgactca ctggaggact tccccaagaa cagctcgttt aacccggccg    120
ccctctccag acacatgtcc tccctgagcc acatctcgcc cttcagccac tccagccaca    180
tgctgaccac gcccacgccg atgcacccgc catccagc                           218
```

<210> SEQ ID NO 93
<211> LENGTH: 887
<212> TYPE: DNA
<213> ORGANISM: Artificial Sequence
<220> FEATURE:
<223> OTHER INFORMATION: Synthetic Polynucleotide

<400> SEQUENCE: 93

```
agggatgctt taaccaaccc tcttcctccc cgtcattgta ctgtaactgg gacagaagaa    60
ataatgggga tatgtggaat ttttaacaac agttaaatgg aaaagcatag acaattactg    120
tagacatgat aaaagaaaca tttgtatgtt cttagactcg aagtttgata aaagtacctt    180
ttcatgtggt gacagttgtg tgttgattgg ctaggtttct cccgtgtgtt ttatacaaaa    240
atggaattga taaccattt tttacaaaat taatttgtct caaaactgtt ctgttcatga    300
tgtattagaa atattttact cagactttaa atattttaaa tctcagattg gttattcaga    360
gtaaccttag aacagaaatt gggaatatat ctttacaatg attgatacca tggtatattg    420
actcttagat gctattgatc tgtagcacca ttttttacaa acgactaagg aaaaaacctg    480
ccaattaaat catgatatgc catcaattat gagacatccc aatttgagag atgttagatt    540
atagaaaagt atgcatttat gactgaaatg gtagtggaat tatttgaatt ctacaccaag    600
cacttaccat gtgccaggcc ctttgcagag tgctctactg accagaaaag ttgttgctgc    660
cacattatag atgtggagcc taagggtcac agaaattgtg tgctatgcca aaaaacattg    720
aactggtaga tagaaaatga cagagctagg attcaaacct agatctggct gactccagag    780
cctagtttta cctggaattg atgttcagtt tatcaaaggt ttctcctttt ggtttaaaat    840
cccaattttt ggcctggcat tgtggtttac gcctgtaatc ccaacac                 887
```

<210> SEQ ID NO 94
<211> LENGTH: 578
<212> TYPE: DNA
<213> ORGANISM: Artificial Sequence
<220> FEATURE:
<223> OTHER INFORMATION: Synthetic Polynucleotide

<400> SEQUENCE: 94

| | | | | | |
|---|---|---|---|---|---|
| cctggaagag | ggactccttg | cctctcccta | tggcctgctg | gcccacctcc | ctggaccccg | 60 |
| ttccaccctc | acccttttcc | tttcccatga | acctggagg | gtggtcccca | ccagctcttt | 120 |
| ggaagtgagc | agatgctgcg | gctggctttc | tgtcagcagg | ccggcctggc | agtgggacaa | 180 |
| tcgccagagg | gtggggctgg | cagaacacca | tctccagcct | cagctttgac | ctgtctcatt | 240 |
| tcccatattc | cttcacaccc | agcttctgga | aggcatgggg | tggctgggat | ttaaggactt | 300 |
| ctgggggacc | aagacatcct | caagaaaaca | ggggcatcca | gggctccctg | gatgaataga | 360 |
| atgcaattca | ttcagaagct | cagaagctaa | gaataagcct | ttgaaatacc | tcattgcatt | 420 |
| tccctttggg | cttcggcttg | gggagatgga | tcaagctcag | agactggcag | tgagagccca | 480 |
| gaaggacctg | tataaaatga | atctggagct | ttacattttc | tgcctctgcc | ttcctcccag | 540 |
| ctcagcaagg | aagtatttgg | gcaccctacc | ctttacct | | | 578 |

<210> SEQ ID NO 95
<211> LENGTH: 254
<212> TYPE: DNA
<213> ORGANISM: Artificial Sequence
<220> FEATURE:
<223> OTHER INFORMATION: Synthetic Polynucleotide

<400> SEQUENCE: 95

| | | | | | |
|---|---|---|---|---|---|
| accacgatcg | ttatgctgat | catacccta | tgatcccagc | aagataatgt | cctgtcctct | 60 |
| aagatgtgca | tcaagcctgg | tacatactga | aaaccctata | aggtcctgga | taattttttgt | 120 |
| ttgattattc | attgaagaaa | catttatttt | ccaattgtgt | gaagttttg | actgttaata | 180 |
| aaagaatctg | tcaaccatca | aagaggtctg | cattatgctt | gcatgtcaaa | aactttaaaa | 240 |
| atcctataat | cttc | | | | | 254 |

<210> SEQ ID NO 96
<211> LENGTH: 114
<212> TYPE: DNA
<213> ORGANISM: Artificial Sequence
<220> FEATURE:
<223> OTHER INFORMATION: Synthetic Polynucleotide

<400> SEQUENCE: 96

| | | | | | |
|---|---|---|---|---|---|
| gcggccgctt | aattaagctg | ccttctgcgg | ggcttgcctt | ctggccatgc | ccttcttctc | 60 |
| tcccttgcac | ctgtacctct | tggtctttga | ataaagcctg | agtaggaagt | ctag | 114 |

<210> SEQ ID NO 97
<211> LENGTH: 1177
<212> TYPE: DNA
<213> ORGANISM: Artificial Sequence
<220> FEATURE:
<223> OTHER INFORMATION: Synthetic Polynucleotide

<400> SEQUENCE: 97

| | | | | | |
|---|---|---|---|---|---|
| gccctgctcg | atgctcacag | ggcccccagc | gagagtccct | gcagtcccctt | tcgacttgca | 60 |
| tttttgcagg | agcagtatca | tgaagcctaa | acgcgatgga | tatatgtttt | tgaaggcaga | 120 |
| aagcaaaatt | atgtttgcca | ctttgcaaag | gagctcactg | tggtgtctgt | gttccaacca | 180 |

```
ctgaatctgg accccatctg tgaataagcc attctgactc atatcccta tttaacaggg      240 tctctagtgc tgtgaaaaaa aaaatgctga acattgcata taacttatat tgtaagaaat      300
actgtacaat gactttattg catctgggta gctgtaaggc atgaaggatg ccaagaagtt      360
taaggaatat gggagaaata gtgtggaaat taagaagaaa ctaggtctga tattcaaatg      420
gacaaactgc cagttttgtt tcctttcact ggccacagtt gtttgatgca ttaaaagaaa      480
ataaaaaaaa gaaaaagag aaagaaaaa aaagaaaaa agttgtaggc gaatcatttg       540
ttcaaagctg ttggcctctg caaggaaat accagttctg ggcaatcagt gttaccgttc      600
accagttgcc gttgagggtt tcagagagcc ttttctagg cctacatgct ttgtgaacaa      660
gtccctgtaa ttgttgtttg tatgtataat tcaaagcacc aaaataagaa aagatgtaga     720
tttatttcat catattatac agaccgaact gttgtataaa tttatttact gctagtctta     780
agaactgctt tctttcgttt gtttgtttca atatttcct tctctctcaa tttttggttg     840
aataaactag attacattca gttggcctaa ggtggttgtg ctcggagggt ttcttgtttc     900
ttttccattt tgtttttgga tgatatttat taaatagctt ctaagagtcc ggcggcatct     960
gtcttgtccc tattcctgca gcctgtgctg agggtagcag tgtatgagct accagcgtgc    1020
atgtcagcga ccctggcccg acaggccacg tcctgcaatc ggcccggctg cctcttcgcc    1080
ctgtcgtgtt ctgtgttagt gatcactgcc tttaatacag tctgttggaa taatattata    1140
agcataataa taaagtgaaa atatttaaa actacaa                              1177

<210> SEQ ID NO 98
<211> LENGTH: 521
<212> TYPE: DNA
<213> ORGANISM: Artificial Sequence
<220> FEATURE:
<223> OTHER INFORMATION: Synthetic Polynucleotide

<400> SEQUENCE: 98
gccctgctcg atgctcacag ggcccccagc gagagtccct gcagtcccctt tcgacttgca      60 tttttgcagg agcagtatca tgaagcctaa acgcgatgga tatatgtttt tgaaggcaga     120
aagcaaaatt atgtttgcca ctttgcaaag gagctcactg tggtgtctgt gttccaacca     180
ctgaatctgg accccatctg tgaataagcc attctgactc atatcccta tttaacaggg      240 tctctagtgc tgtgaaaaaa aaaatgctga acattgcata taacttatat tgtaagaaat      300
actgtacaat gactttattg catctgggta gctgtaaggc atgaaggatg ccaagaagtt      360
taaggaatat gggagaaata gtgtggaaat taagaagaaa ctaggtctga tattcaaatg      420
gacaaactgc cagttttgtt tcctttcact ggccacagtt gtttgatgca ttaaaagaaa      480
ataaaaaaaa gaaaaagag aaagaaaaa aaagaaaaa a                            521

<210> SEQ ID NO 99
<211> LENGTH: 656
<212> TYPE: DNA
<213> ORGANISM: Artificial Sequence
<220> FEATURE:
<223> OTHER INFORMATION: Synthetic Polynucleotide

<400> SEQUENCE: 99
gttgtaggcg aatcatttgt tcaaagctgt tggcctctgc aaaggaaata ccagttctgg      60
gcaatcagtg ttaccgttca ccagttgccg ttgagggttt cagagagcct ttttctaggc     120
ctacatgctt tgtgaacaag tccctgtaat tgttgtttgt atgtataatt caaagcacca    180
```

```
aaataagaaa agatgtagat ttatttcatc atattataca gaccgaactg ttgtataaat    240
ttatttactg ctagtcttaa gaactgcttt ctttcgtttg tttgtttcaa tattttcctt    300
ctctctcaat ttttggttga ataaactaga ttacattcag ttggcctaag gtggttgtgc    360
tcggagggtt tcttgtttct tttccatttt gtttttggat gatatttatt aaatagcttc    420
taagagtccg gcggcatctg tcttgtccct attcctgcag cctgtgctga gggtagcagt    480
gtatgagcta ccagcgtgca tgtcagcgac cctggcccga caggccacgt cctgcaatcg    540
gcccggctgc ctcttcgccc tgtcgtgttc tgtgttagtg atcactgcct ttaatacagt    600
ctgttggaat aatattataa gcataataat aaagtgaaaa tattttaaaa ctacaa       656

<210> SEQ ID NO 100
<211> LENGTH: 41
<212> TYPE: PRT
<213> ORGANISM: Artificial Sequence
<220> FEATURE:
<223> OTHER INFORMATION: Synthetic Polypeptide

<400> SEQUENCE: 100

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 101
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 101

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 102
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 102

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 103
<211> LENGTH: 153
<212> TYPE: PRT
<213> ORGANISM: Artificial Sequence
<220> FEATURE:
```

<223> OTHER INFORMATION: Synthetic Polypeptide

<400> SEQUENCE: 103

Arg Ser Lys Arg Ser Arg Leu Leu His Ser Asp Tyr Met Asn Met Thr
1               5                   10                  15
Pro Arg Arg Pro Gly Pro Thr Arg Lys His Tyr Gln Pro Tyr Ala Pro
            20                  25                  30
Pro Arg Asp Phe Ala Ala Tyr Arg Ser Arg Val Lys Phe Ser Arg Ser
        35                  40                  45
Ala Asp Ala Pro Ala Tyr Gln Gln Gly Gln Asn Gln Leu Tyr Asn Glu
    50                  55                  60
Leu Asn Leu Gly Arg Arg Glu Glu Tyr Asp Val Leu Asp Lys Arg Arg
65                  70                  75                  80
Gly Arg Asp Pro Glu Met Gly Gly Lys Pro Arg Arg Lys Asn Pro Gln
                85                  90                  95
Glu Gly Leu Tyr Asn Glu Leu Gln Lys Asp Lys Met Ala Glu Ala Tyr
            100                 105                 110
Ser Glu Ile Gly Met Lys Gly Glu Arg Arg Arg Gly Lys Gly His Asp
        115                 120                 125
Gly Leu Tyr Gln Gly Leu Ser Thr Ala Thr Lys Asp Thr Tyr Asp Ala
    130                 135                 140
Leu His Met Gln Ala Leu Pro Pro Arg
145                 150

<210> SEQ ID NO 104
<211> LENGTH: 154
<212> TYPE: PRT
<213> ORGANISM: Artificial Sequence
<220> FEATURE:
<223> OTHER INFORMATION: Synthetic Polypeptide

<400> SEQUENCE: 104

Lys Arg Gly Arg Lys Lys Leu Leu Tyr Ile Phe Lys Gln Pro Phe Met
1               5                   10                  15
Arg Pro Val Gln Thr Thr Gln Glu Glu Asp Gly Cys Ser Cys Arg Phe
            20                  25                  30
Pro Glu Glu Glu Glu Gly Gly Cys Glu Leu Arg Val Lys Phe Ser Arg
        35                  40                  45
Ser Ala Asp Ala Pro Ala Tyr Gln Gln Gly Gln Asn Gln Leu Tyr Asn
    50                  55                  60
Glu Leu Asn Leu Gly Arg Arg Glu Glu Tyr Asp Val Leu Asp Lys Arg
65                  70                  75                  80
Arg Gly Arg Asp Pro Glu Met Gly Gly Lys Pro Arg Arg Lys Asn Pro
                85                  90                  95
Gln Glu Gly Leu Tyr Asn Glu Leu Gln Lys Asp Lys Met Ala Glu Ala
            100                 105                 110
Tyr Ser Glu Ile Gly Met Lys Gly Glu Arg Arg Arg Gly Lys Gly His
        115                 120                 125
Asp Gly Leu Tyr Gln Gly Leu Ser Thr Ala Thr Lys Asp Thr Tyr Asp
    130                 135                 140
Ala Leu His Met Gln Ala Leu Pro Pro Arg
145                 150

<210> SEQ ID NO 105
<211> LENGTH: 149
<212> TYPE: PRT
<213> ORGANISM: Artificial Sequence
<220> FEATURE:
<223> OTHER INFORMATION: Synthetic Polypeptide

<400> SEQUENCE: 105

```
Arg Arg Asp Gln Arg Leu Pro Pro Asp Ala His Lys Pro Pro Gly Gly
1               5                   10                  15

Gly Ser Phe Arg Thr Pro Ile Gln Glu Glu Ala Asp Ala His Ser
            20                  25                  30

Thr Leu Ala Lys Ile Arg Val Lys Phe Ser Arg Ser Ala Asp Ala Pro
            35                  40                  45

Ala Tyr Gln Gln Gly Gln Asn Gln Leu Tyr Asn Glu Leu Asn Leu Gly
        50                  55                  60

Arg Arg Glu Glu Tyr Asp Val Leu Asp Lys Arg Arg Gly Arg Asp Pro
65                  70                  75                  80

Glu Met Gly Gly Lys Pro Arg Arg Lys Asn Pro Gln Glu Gly Leu Tyr
                85                  90                  95

Asn Glu Leu Gln Lys Asp Lys Met Ala Glu Ala Tyr Ser Glu Ile Gly
                100                 105                 110

Met Lys Gly Glu Arg Arg Arg Gly Lys Gly His Asp Gly Leu Tyr Gln
            115                 120                 125

Gly Leu Ser Thr Ala Thr Lys Asp Thr Tyr Asp Ala Leu His Met Gln
        130                 135                 140

Ala Leu Pro Pro Arg
145
```

<210> SEQ ID NO 106
<211> LENGTH: 191
<212> TYPE: PRT
<213> ORGANISM: Artificial Sequence
<220> FEATURE:
<223> OTHER INFORMATION: Synthetic Polypeptide

<400> SEQUENCE: 106

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Arg Asp Gln Arg Leu
        35                  40                  45

Pro Pro Asp Ala His Lys Pro Pro Gly Gly Gly Ser Phe Arg Thr Pro
    50                  55                  60

Ile Gln Glu Glu Gln Ala Asp Ala His Ser Thr Leu Ala Lys Ile Arg
65                  70                  75                  80

Val Lys Phe Ser Arg Ser Ala Asp Ala Pro Ala Tyr Gln Gln Gly Gln
                85                  90                  95

Asn Gln Leu Tyr Asn Glu Leu Asn Leu Gly Arg Arg Glu Glu Tyr Asp
                100                 105                 110

Val Leu Asp Lys Arg Arg Gly Arg Asp Pro Glu Met Gly Gly Lys Pro
            115                 120                 125

Arg Arg Lys Asn Pro Gln Glu Gly Leu Tyr Asn Glu Leu Gln Lys Asp
        130                 135                 140

Lys Met Ala Glu Ala Tyr Ser Glu Ile Gly Met Lys Gly Glu Arg Arg
145                 150                 155                 160

Arg Gly Lys Gly His Asp Gly Leu Tyr Gln Gly Leu Ser Thr Ala Thr
                165                 170                 175

Lys Asp Thr Tyr Asp Ala Leu His Met Gln Ala Leu Pro Pro Arg
```

<210> SEQ ID NO 107
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 107

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 108
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 108

Gly Ser Thr Ser Gly Ser Gly Lys Pro Gly Ser Gly Glu Gly Ser Thr
1               5                   10                  15

Lys Gly

<210> SEQ ID NO 109
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 109

Gly Ser Thr Ser Gly Ser Gly Lys Pro Gly Ser Gly Glu Gly Ser Thr
1               5                   10                  15

Lys Gly Ser Gly Gly Ser Gly Gly Gly
            20                  25

<210> SEQ ID NO 110
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 110

Met Ala Leu Pro Val Thr Ala Leu Leu Leu Pro Leu Ala Leu Leu Leu
1               5                   10                  15

His Ala Ala Arg Pro
            20

<210> SEQ ID NO 111
<211> LENGTH: 83
<212> TYPE: PRT
<213> ORGANISM: Artificial Sequence
<220> FEATURE:
<223> OTHER INFORMATION: Synthetic Polypeptide

<400> SEQUENCE: 111

```
Phe Val Pro Val Phe Leu Pro Ala Lys Pro Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn
```

<210> SEQ ID NO 112
<211> LENGTH: 1515
<212> TYPE: DNA
<213> ORGANISM: Artificial Sequence
<220> FEATURE:
<223> OTHER INFORMATION: Synthetic Polynucleotide

<400> SEQUENCE: 112

| | |
|---|---|
| atggcactgc cagtcacagc actgctgctg ccactggcac tgctgctcca cgccgccaga | 60 |
| cccgacatcg tgctgacaca gagcccagca agcctggccg tgagcccagg ccagagagcc | 120 |
| acaatcacat gcagagccag cgagtccgtg tccttcctgg catcaacct gatccactgg | 180 |
| taccagcaga agcccggaca gccacccaaa ctgctgatct actccgccag caacctgcag | 240 |
| tcaggcgtgc cagccagatt cagcggcagc ggcagcggaa ccgacttcac cctgacaatc | 300 |
| agctcagtgg aaccagaaga caccgccaac tactactgcc tgcagagcag aacccctgccc | 360 |
| agaaccttcg gccaaggcac caaggtcgaa atcaagggct ccacaagcgg cagcggaaag | 420 |
| cccggaagcg gcgagggaag caccaagggc cagatccagc tggtgcagag cggccccgaa | 480 |
| ctgaagaaac ccggcggaag cgtgaaaatc tcctgcaagg ccagcggcta caccttcacc | 540 |
| tcctacagca tcaactgggt gcgccaggcc caggcaagg gcctggaatg ggtcggctgg | 600 |
| atcaacaccg agacaagaga gcccgcctac gcccagggct tcacaggcag attcaccttc | 660 |
| agcgcagaca caagcaagag catggcctac ctgcagatca actccctgag gcagaggac | 720 |
| accgccgtct actactgcgc cctggactac ctctactccc tggacttctg gggccagggc | 780 |
| accctcgtga ccgtgtccag cttcgtgccc gtgttcctgc cagccaagcc aaccacaaca | 840 |
| ccagcaccca gaccaccaac accagcacca acaatcgcca gccagccact gtccctgagg | 900 |
| ccagaggcat gcagaccagc agcaggcgga gccgtgcaca ccagaggact ggacttcgcc | 960 |
| tgcgacatct acatctgggc caccactggcc ggaacatgcg gcgtgctgct gctgagcctg | 1020 |
| gtcatcaccc tgtactgcaa ccaccggaac aaacgcggga gaaaaaagct cctctacatc | 1080 |
| ttcaagcaac cattcatgcg cccagtccaa accacacagg aggaagacgg atgcagctgc | 1140 |
| aggttccccg aagaggagga aggcggatgc gagctcagag tgaagttcag cagatccgcc | 1200 |
| gacgcaccag cctaccagca gggacagaac cagctgtaca cgagctgaa cctggggaga | 1260 |

| | |
|---|---|
| agagaagagt acgacgtgct ggataagcgg agaggcagag accctgagat gggcggcaag | 1320 |
| cccagacgga agaacccaca agagggcctg tacaacgagc tgcagaaaga caagatggcc | 1380 |
| gaggcctaca gcgagatcgg aatgaagggc gagcgcagaa gaggcaaggg acacgacgga | 1440 |
| ctgtaccagg gcctgagcac agccaccaag gatacctacg atgccctgca catgcaggcc | 1500 |
| ctgccaccaa gatga | 1515 |

<210> SEQ ID NO 113
<211> LENGTH: 1515
<212> TYPE: DNA
<213> ORGANISM: Artificial Sequence
<220> FEATURE:
<223> OTHER INFORMATION: Synthetic Polynucleotide

<400> SEQUENCE: 113

| | |
|---|---|
| atggcactgc cagtcacagc actgctgctg ccactggcac tgctgctcca cgccgccaga | 60 |
| cccgacatcg tgctgacaca gagcccagca agcctggccg tgagcccagg ccagagagcc | 120 |
| acaatcacat gcagagccag cgagtccgtg acaatcctgg ctcccacct gatccactgg | 180 |
| taccagcaga agcccggaca gccacccaaa ctgctgatca acctggccag caacgtgaac | 240 |
| acaggcgtgc cagccagatt cagcggcagc ggcagcggaa ccgacttcac cctgacaatc | 300 |
| agctcagtgg aaccagaaga caccgccaac tactactgcc tgcagagcag aacactgccc | 360 |
| agaaccttcg gccaaggcac caaggtcgaa atcaagggct ccacaagcgg cagcggaaag | 420 |
| cccggaagcg gcgagggaag caccaagggc cagatccagc tggtgcagag cggcccgaa | 480 |
| ctgaagaaac ccggcggaag cgtgaaaatc tcctgcaagg ccagcggcta caccttcacc | 540 |
| gactacagca tcaactgggt gcgccaggcc ccaggcaagg gcctggaatg ggtcggctgg | 600 |
| atcaacaccg agacaagaga gccgcctac gcctacgact tcacaggcag attcaccttc | 660 |
| agcgcagaca caagcaagag catggccac ctgcagatca ctccctgag gcagaggac | 720 |
| accgccgtct actactgcgc cctggactac acctacggca tggactactg gggccagggc | 780 |
| accctcgtga ccgtgtccag cttcgtgccc gtgttcctgc agccaagcc aaccacaaca | 840 |
| ccagcaccca gaccaccaac accagcacca acaatcgcca gccagccact gtccctgagg | 900 |
| ccagaggcat gcagaccagc agcaggcgga gccgtgcaca ccagaggact ggacttcgcc | 960 |
| tgcgacatct acatctgggc caccactggcc ggaacatgcg cgtgctgct gctgagcctg | 1020 |
| gtcatcaccc tgtactgcaa ccaccggaac aaacgcggga gaaaaaagct cctctacatc | 1080 |
| ttcaagcaac cattcatgcg cccagtccaa accacacagg aggaagacgg atgcagctgc | 1140 |
| aggttccccg aagaggagga aggcggatgc gagctcagag tgaagttcag cagatccgcc | 1200 |
| gacgcaccag cctaccagca gggacagaac cagctgtaca acgagctgaa cctggggaga | 1260 |
| agagaagagt acgacgtgct ggataagcgg agaggcagag accctgagat gggcggcaag | 1320 |
| cccagacgga agaacccaca agagggcctg tacaacgagc tgcagaaaga caagatggcc | 1380 |
| gaggcctaca gcgagatcgg aatgaagggc gagcgcagaa gaggcaaggg acacgacgga | 1440 |
| ctgtaccagg gcctgagcac agccaccaag gatacctacg atgccctgca catgcaggcc | 1500 |
| ctgccaccaa gatga | 1515 |

<210> SEQ ID NO 114
<211> LENGTH: 462
<212> TYPE: PRT
<213> ORGANISM: Artificial Sequence
<220> FEATURE:

<223> OTHER INFORMATION: Synthetic Polypeptide

<400> SEQUENCE: 114

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ser Ser Leu
            20                  25                  30

Ser Ala Ser Val Gly Asp Arg Ala Thr Ile Ser Cys Arg Ala Ser Glu
        35                  40                  45

Ser Val Thr Ile Leu Gly Ser His Leu Ile His Trp Tyr Gln Gln Lys
    50                  55                  60

Pro Gly Gln Ala Pro Lys Leu Leu Ile Gln Leu Ala Ser Asn Val Gln
65                  70                  75                  80

Thr Gly Val Pro Ala Arg Phe Ser Gly Ser Gly Ser Gly Thr Asp Phe
                85                  90                  95

Thr Leu Thr Ile Ser Ser Val Glu Pro Glu Asp Val Ala Val Tyr Tyr
            100                 105                 110

Cys Leu Gln Ser Arg Thr Ile Pro Arg Thr Phe Gly Gln Gly Thr Lys
        115                 120                 125

Val Glu Ile Lys Gly Ser Thr Ser Gly Ser Gly Lys Pro Gly Ser Gly
    130                 135                 140

Glu Gly Ser Thr Lys Gly Gln Ile Gln Leu Val Glu Ser Gly Ala Glu
145                 150                 155                 160

Val Lys Lys Pro Gly Gly Ser Val Lys Val Ser Cys Lys Ala Ser Gly
                165                 170                 175

Tyr Thr Phe Thr Asp Tyr Ser Ile Asn Trp Val Arg Gln Ala Pro Gly
            180                 185                 190

Lys Gly Leu Glu Trp Val Gly Trp Ile Asn Thr Glu Thr Arg Glu Pro
        195                 200                 205

Ala Tyr Ala Tyr Asp Phe Arg Gly Arg Phe Ala Ile Ser Ala Glu Thr
    210                 215                 220

Ser Lys Ser Thr Ala Tyr Leu Gln Met Asn Ser Leu Arg Ala Glu Asp
225                 230                 235                 240

Thr Ala Val Tyr Tyr Cys Ala Leu Asp Tyr Ser Tyr Ala Met Asp Tyr
                245                 250                 255

Trp Gly Gln Gly Thr Leu Val Thr Val Ser Ser Phe Val Pro Val Phe
            260                 265                 270

Leu Pro Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Asn His Arg Asn Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Arg Arg
    420                 425                 430

Gly Lys Gly His Asp Gly Leu Tyr Gln Gly Leu Ser Thr Ala Thr Lys
435                 440                 445

Asp Thr Tyr Asp Ala Leu His Met Gln Ala Leu Pro Pro Arg
450                 455                 460

<210> SEQ ID NO 115
<211> LENGTH: 1389
<212> TYPE: DNA
<213> ORGANISM: Artificial Sequence
<220> FEATURE:
<223> OTHER INFORMATION: Synthetic Polynucleotide

<400> SEQUENCE: 115

| | | |
|---|---|---|
| atggcactgc ctgttaccgc gctgctcctc cccctt gctc tcctgcttca cgcagcgagg | 60 |
| cctgacatcg tactcaccca gtctccgagt agcctgtctg caagtgtcgg cgacagggcg | 120 |
| acgataagtt gcagagccag cgaaagcgtc acaattttgg gttctcactt gattcactgg | 180 |
| tatcagcaga aacccggcca ggcgccaaaa cttttgattc agctcgcttc aaatgttcag | 240 |
| accggggtcc cagctcggtt ctcaggctcc ggttcaggaa cggacttcac tcttaccatc | 300 |
| tcatccgtgg agcctgagga tgttgctgtg tattattgtt gcagtccag aactatccca | 360 |
| cgcactttg ccaaggcac caaagtggag ataaaggat caacatcagg aagcggcaag | 420 |
| cctggttccg gcgaaggctc aactaaaggt cagatccaat ggtcgagtc aggtgcagag | 480 |
| gttaaaaagc ccggcggttc tgtgaaggtt agttgtaagg catccgggta cacttttacg | 540 |
| gactatagca tcaattgggt gcgacaggcc cccggaaaag gtcttgaatg ggtgggttgg | 600 |
| attaataccg aaacgcggga accggcctat gcctatgact ttagaggtcg cttcgctatt | 660 |
| tcagcagaaa cctcaaagtc cactgcgtat ctgcagatga acgtctccg ggccgaggac | 720 |
| accgccgttt actactgcgc cttggattat agctacgcaa tggactattg ggtcaggga | 780 |
| accctggtga ctgttagcag cttcgttcca gtgtttctgc ccgctaagcc cacaaccact | 840 |
| cctgcaccgc gaccacccac acctgcgcct acaattgcgt cacagcccct gagccttcga | 900 |
| ccggaagcct gtcggccagc cgcaggcggg gcggtccata ctaggggact ggactttgct | 960 |
| tgtgatattt acatctgggc tccccttgcc ggaacgtgtg gcgttttgct cctttctctg | 1020 |
| gtaataaccc tgtattgcaa tcaccggaat cgagtgaagt tctccagaag cgccgatgca | 1080 |
| cccgcgtatc aacagggtca aaatcaattg tataacgaac ttaaccttgg gaggcgcgag | 1140 |
| gagtacgatg tactcgacaa agacgcggga agggaccccg aaatgggcgg caagccgcgg | 1200 |
| aggaaaaacc cgcaagaggg actctataac gaacttcaga aggataagat ggcagaagcc | 1260 |
| tactcagaga ttggaatgaa gggtgagcgg cgcaggggga agggtcacga tggtctgtat | 1320 |
| caaggactgt ctacggcaac caaagacacg tatgacgcat tgcacatgca agccttgcct | 1380 |
| ccccggtga | 1389 |

<210> SEQ ID NO 116
<211> LENGTH: 1389
<212> TYPE: DNA
<213> ORGANISM: Artificial Sequence
<220> FEATURE:
<223> OTHER INFORMATION: Synthetic Polynucleotide

<400> SEQUENCE: 116

```
atggctctgc cggtaacagc gcttcttctc ccgcttgccc tcctcttgca cgctgctcgg    60
ccagatattg tcctcacaca gagcccgtcc tcactttcag cgagcgtcgg ggaccgcgct   120
accatcagtt gtcgagccag tgaaagcgtc actattctgg ggagccacct tatacattgg   180
tatcaacaaa agccaggcca ggcccccaaa ctgctgattc agctcgcatc taatgttcag   240
actggagtgc ctgcaaggtt tagcggtagt gggtcaggga cagatttcac cttgaccatt   300
agctcagttg agcctgaaga tgtggccgtt tattactgcc tccaaagccg cactatacct   360
cggaccttcg gccagggaac aaaggtggag attaagggta gtacctcagg tagtggcaag   420
ccagggagcg gcgaggggtc tacaaagggt caaattcaat tggtgcagtc cggaccagaa   480
ctgaaaaaac cggcgggag cgtcaagatt tcctgtgcag catcaggcta catttact      540 gattacagta ttaactgggt gagacaagcg cctggaaagg ccttgagtg ggtgggttgg    600 attaacacgg agactagaga acccgcgtac gcctacgatt tagaggccg gttcactttc   660 tccgccgata caagtaaatc cacagcatat ctccaaatga atagcctag agcggaggat   720 accgccgtgt attattgcgc gctcgactat tcttacgcaa tggactactg ggggcagggt   780
actctcgtca ccgtatcctc atttgttccc gtattttgc ccgccaagcc gaccactact   840
ccggcccctc gacctccgac ccctgctccg actattgcga gtcaaccatt gagccttcgg   900
cctgaggcat gtagaccggc agctggtggc gcagtccata cacgagggct tgattttgcg   960
tgcgacatct atatatgggc gccattggct gggacgtgcg gcgtccttct cttgtcactc  1020
gtgataactc tgtactgcaa tcacagaaac cgcgtgaagt tttccagaag cgcggacgcg  1080
ccggcctatc aacaagggca gaatcagctg tacaacgaac tcaatttggg gcgaagggag  1140
gagtatgatg ttttggacaa aaggcgaggc cgcgaccctg aaatgggcgg taagccacgc  1200
agaaaaaacc cccaagaggg attgtacaat gaactgcaaa agacaagat ggctgaggca   1260 tacagtgaga taggaatgaa aggtgaacgg cgccggggaa aaggacatga cgggttgtac  1320
cagggtctta gcactgcaac gaaagatacc tatgacgccc tgcacatgca agcattgccc  1380
ccacggtga                                                          1389
```

<210> SEQ ID NO 117
<211> LENGTH: 55
<212> TYPE: PRT
<213> ORGANISM: Artificial Sequence
<220> FEATURE:
<223> OTHER INFORMATION: Synthetic Polypeptide

<400> SEQUENCE: 117

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55
```

<210> SEQ ID NO 118
<211> LENGTH: 21
<212> TYPE: PRT
<213> ORGANISM: Artificial Sequence
<220> FEATURE:
<223> OTHER INFORMATION: Synthetic Polypeptide

```
<400> SEQUENCE: 118

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 119
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 119

Leu Tyr Cys Asn His Arg Asn
1               5

<210> SEQ ID NO 120
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 120

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn
            20                  25

<210> SEQ ID NO 121
<211> LENGTH: 184
<212> TYPE: PRT
<213> ORGANISM: Artificial Sequence
<220> FEATURE:
<223> OTHER INFORMATION: Synthetic Polypeptide

<400> SEQUENCE: 121

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175
```

Ile Glu Lys Ser Ile Ser Ala Arg
          180

<210> SEQ ID NO 122
<211> LENGTH: 1389
<212> TYPE: DNA
<213> ORGANISM: Artificial Sequence
<220> FEATURE:
<223> OTHER INFORMATION: Synthetic Polynucleotide

<400> SEQUENCE: 122

| atggcactgc | ctgttacagc | tctgctgctg | cctctggcac | tgctgcttca | tgccgccaga | 60 |
| cctgacatcg | tgctgacaca | gtctccttcc | agcctgagcg | catctgtcgg | cgacagagcc | 120 |
| acaatcagct | gcagagccag | cgagtctgtg | acaatcctgg | ctctcacct | gatccactgg | 180 |
| tatcagcaga | agcccggaca | ggcacctaaa | ctgctgatcc | agctggcctc | taatgtgcag | 240 |
| acaggcgtgc | cagccagatt | ttctggcagc | ggcagcggaa | ccgacttcac | cctgacaatc | 300 |
| agctcagtgg | aaccagaaga | tgtggccgtg | tactactgcc | tgcagagcag | aacaatcccc | 360 |
| agaacctttg | gccaaggcac | caaggtcgaa | atcaagggct | ctacaagcgg | cagcggaaag | 420 |
| cctggatctg | gcgagggatc | taccaagggc | cagattcagc | tggtgcagtc | tggccccgaa | 480 |
| ctgaagaaac | ctggcggaag | cgtgaaaatc | tcctgcgcag | ccagcggcta | caccttcacc | 540 |
| gactacagca | tcaactgggt | tcgccaggcc | ctggcaaggg | cctggaatg | ggtcggctgg | 600 |
| atcaacaccg | agactagaga | gcccgcctac | gcctacgact | cagaggcag | attcaccttc | 660 |
| agcgcagaca | caagcaagag | cacagcctac | ctgcagatga | actccctgag | agcagaggac | 720 |
| accgccgtct | actattgcgc | cctggattac | agctacgcca | tggattattg | gggccagggc | 780 |
| accctcgtga | ccgtgtcatc | ttttgtgcct | gtgttcctgc | ctgccaagcc | taccacaaca | 840 |
| ccagctccta | gacctccaac | tcctgctcct | acaatcgcct | ctcagccact | gtctctgagg | 900 |
| cctgaggcat | gtagacctgc | tgctggcgga | gccgtgcata | ccagaggact | ggatttcgcc | 960 |
| tgcgacatct | acatctgggc | tcctctggct | ggaacatgtg | gcgtgctgct | gctgagcctg | 1020 |
| gtcatcaccc | tgtactgcaa | ccaccggaac | agagtgaagt | tcagcagatc | cgccgatgct | 1080 |
| cctgcctacc | agcagggaca | gaaccagctg | tacaacgagc | tgaacctggg | gagaagagaa | 1140 |
| gagtacgacg | tgctggataa | gcggagaggc | agagatcctg | agatgggcgg | caagcccaga | 1200 |
| cggaagaatc | tcaagaggg | cctgtataat | gagctgcaga | agacaagat | ggccgaggcc | 1260 |
| tacagcgaga | tcggaatgaa | gggcgagcgc | agaagaggca | agggacacga | tggactgtac | 1320 |
| cagggcctga | gcacagccac | caaggatacc | tatgatgccc | tgcacatgca | ggccctgcct | 1380 |
| ccaagatga |            |            |            |            |            | 1389 |

<210> SEQ ID NO 123
<211> LENGTH: 1389
<212> TYPE: DNA
<213> ORGANISM: Artificial Sequence
<220> FEATURE:
<223> OTHER INFORMATION: Synthetic Polynucleotide

<400> SEQUENCE: 123

| atggcactgc | cggtaacagc | gctcctcctc | ccgctcgccc | tcctcctcca | cgcagcacgg | 60 |
| ccagacatcg | tcctcacaca | gagcccgagc | agcctcagcg | cgagcgtcgg | ggaccgcgca | 120 |
| accatcagct | gccgagccag | cgaaagcgtc | acaatcctcg | ggagccacct | gatacactgg | 180 |
| taccaacaaa | agccaggcca | gggcccccaaa | ctgctgatcc | agctcgcaag | caacgtccag | 240 |

```
acaggagtgc cagcaaggtt cagcggaagc gggagcggaa cagacttcac cctcaccatc      300
agcagcgtcg agccagaaga tgtggccgtc tactactgcc tccaaagccg cacaatacca      360
cggaccttcg gccagggaac aaaggtggag atcaagggaa gcaccagcgg aagcggcaag      420
ccagggagcg gcgaggggag cacaaaggga caaatccaac tcgtgcagag cggaccagaa      480
ctgaaaaagc cgggcggaag cgtcaagatc agctgcgcag caagcggcta cacattcaca      540
gactacagca tcaactgggt gagacaagcg ccaggaaagg gcctcgaatg ggtgggatgg      600
atcaacacgg agacaagaga acccgcatac gcctacgact cagaggccgg gttcacattc      660
agcgccgaca caagcaagag cacagcatac ctccaaatga acagcctcag agcggaggac      720
accgccgtgt actactgcgc gctcgactac agctacgcaa tggactactg gggacaggga      780
acactcgtca ccgtaagcag cttcgtaccc gtattcctcc ccgccaagcc gaccacaaca      840
ccggccccac gaccaccaac accagccccg acaatcgcga gccaaccact cagcctccgg      900
ccagaggcgt gcagaccggc agcaggaggc gcagtccaca cacgaggact cgacttcgcg      960
tgcgacatat acatctgggc accactcgca ggaacgtgcg gcgtcctcct cctcagcctc     1020
gtgataaaca ctgtactgca accacagaaac cgcgtgaagt tcagcagaag cgcggacgcg     1080
ccggcctacc aacaaggaca gaaccagctg tacaacgaac tcaacctcgg acgaagggag     1140
gagtacgacg tcctcgacaa aaggcgaggc cgcgacccag aaatgggcgg aaagccacgc     1200
agaaaaaacc cccaagaggg actctacaac gaactgcaaa aggacaagat ggcagaggca     1260
tacagcgaga taggaatgaa aggagaacgg cgccggggaa aaggcacgga cgggctctac     1320
cagggactca gcacagcaac gaaagacacc tacgacgccc tgcacatgca agcactcccc     1380
ccacggtga                                                             1389
```

<210> SEQ ID NO 124
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 124

Gly Gly Gly Gly Ser
1               5

<210> SEQ ID NO 125
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 125

Gly Gly Gly Gly Ser Gly Gly Gly Gly Ser
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 126

Gly Gly Gly Gly Ser Gly Gly Gly Gly Ser Gly Gly Gly Gly Ser
1               5                   10                  15

<210> SEQ ID NO 127
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 127

Gly Ser Thr Ser Gly Gly Gly Ser Gly Gly Gly Ser Gly Gly Gly Gly
1               5                   10                  15

Ser Ser

<210> SEQ ID NO 128
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 128

Gly Ser Thr Ser Gly Ser Gly Lys Pro Gly Ser Ser Glu Gly Ser Thr
1               5                   10                  15

Lys Gly

<210> SEQ ID NO 129
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 129

Gly Gly Gly Gly Ser Gly Gly Gly
1               5

<210> SEQ ID NO 130
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 130

Gly Gly Gly Ser
1

<210> SEQ ID NO 131
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 131

Gly Leu Tyr Gly Leu Tyr Gly Leu Tyr Gly Leu Tyr Ser Glu Arg
1               5                   10                  15

<210> SEQ ID NO 132
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 132

```
Gly Leu Tyr Gly Leu Tyr Gly Leu Tyr Gly Leu Tyr Ser Glu Arg Gly
1               5                   10                  15

Leu Tyr Gly Leu Tyr Gly Leu Tyr Gly Leu Tyr Ser Glu Arg Gly Leu
            20                  25                  30

Tyr Gly Leu Tyr Gly Leu Tyr Gly Leu Tyr Ser Glu Arg Gly Leu Tyr
        35                  40                  45

Gly Leu Tyr Gly Leu Tyr Gly Leu Tyr Ser Glu Arg
    50                  55                  60

<210> SEQ ID NO 133
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 133

Gly Leu Tyr Gly Leu Tyr Gly Leu Tyr Gly Leu Tyr Ser Glu Arg Gly
1               5                   10                  15

Leu Tyr Gly Leu Tyr Gly Leu Tyr Gly Leu Tyr Ser Glu Arg Gly Leu
            20                  25                  30

Tyr Gly Leu Tyr Gly Leu Tyr Gly Leu Tyr Ser Glu Arg
        35                  40                  45
```

ANTI-BCMA CHIMERIC ANTIGEN RECEPTORS

RELATED APPLICATIONS

This application claims priority under 35 U.S.C. §§ 120 and 365(c) to and is a continuation of international PCT Application, PCT/US2020/022671, filed Mar. 13, 2020, which claims priority under 35 U.S.C. § 119(e) to U.S. Provisional Application, U.S. Ser. No. 62/819,068, filed on Mar. 15, 2019, each of which is incorporated herein by reference.

BACKGROUND

B cell maturation antigen (BCMA) is a tumor necrosis family receptor (TNFR) member expressed on cells of the B cell lineage. BCMA expression is the highest on terminally differentiated B cells. BCMA is involved in mediating the survival of plasma cells for maintaining long-term humoral immunity. The expression of BCMA has been recently linked to a number of cancers, autoimmune disorders, allergic disorders, and infectious diseases. Cancers with increased expression of BCMA include some hematological cancers, such as multiple myeloma, Hodgkin's and non-Hodgkin's lymphoma, various leukemias, and glioblastoma. Autoimmune diseases linked to BCMA include, without limitation, myasthenia gravis, systemic lupus erythematosus (SLE), rheumatoid arthritis, blistering skin diseases, e.g., pemphigus, psoriasis, inflammatory bowel disease, celiac sprue, pernicious anemia, idiopathic thrombocytopenia purpura, scleroderma, Graves' disease, Sjögren syndrome, Goodpasture syndrome, and type 1 diabetes. Many autoantibody-mediated autoimmune diseases require chronic treatment with systemic steroids, or immunosuppressants, which involve significant toxicity. Allergic disorders linked to BCMA include anaphylaxis, asthma, food allergy, stinging insect allergy, drug allergy, allergic rhinitis, urticaria, angioedema, eczema, atopic dermatitis, contact dermatitis, and eosinophilic esophagitis. Many allergic diseases require chronic treatment with systemic or local steroids, immunomodulatory therapy, or immunotherapy. Patients affected by environmental, food, drug, and insect allergies often must modify their lifestyles to avoid the offending allergens.

A promising new approach to treating BCMA-related conditions is adoptive transfer of T cells genetically modified to recognize malignancy-associated antigens. See, e.g., U.S. Pat. No. 9,765,342 to Kochenderfer. T cells can be genetically modified by introduction of a nucleic acid construct to express chimeric antigen receptors (CARs), which are fusion proteins comprising an extracellular antigen recognition moiety and an intracellular signaling domain. See, e.g., Eshhar et al., Proc. Natl. Acad. Sci. USA, 1993; 90:720-724, and Sadelain et al., Curr. Opin. Immunol, 2009; 21:215-223. CAR T cells, such as those modified to recognize BCMA, have shown benefit in treating conditions such as multiple myeloma. See, e.g., Ali et al., Blood, 2016; 128:1688-1700; Brudno et al., J. Clin. Oncol., 2018; 36:2267-2280.

CAR proteins and CAR T cells directed against BCMA have previously been described. See, e.g., U.S. Pat. No. 9,765,342 to Kochenderfer; U.S. Pat. No. 10,174,095 to Brogdon et al., and U.S. Pat. App. Pub. No. 2017/0226216 A1 of Morgan et al., the disclosures of which are incorporated herein by reference.

Previously disclosed forms of anti-BCMA CAR T cell therapy suffer from several drawbacks, including manufacturing difficulties, suboptimal expression, suboptimal target engagement and tumor killing, inflammatory side effects, and immunogenicity.

Therefore, there is a need for improved CAR compositions and methods for the treatment of BCMA-related conditions.

SUMMARY OF THE INVENTION

Some aspects of the disclosure are based at least in part on the surprising discovery that novel constructs expressing modified chimeric antigen receptors demonstrate improved properties, including increased binding to BCMA, and killing of multiple myeloma cells in vitro and in vivo. Exemplary improvements include modification of CDR sequences that cause CAR T cells to bind more effectively to BCMA and are more efficient at killing cancer cells; 5' and 3' untranslated sequences (UTRs) that improve CAR expression; cytoplasmic domains that improve CAR expression; and other improvements, such as improved polyadenine (polyA) tails that also improve expression.

In some aspects, the disclosure provides chimeric antigen receptor (CAR) specific for BCMA. In some embodiments, the CAR comprises at least one novel CDR sequence from any one of SEQ ID NOs: 2, 3, 5, 6, 8, 9, 11, 13, 14, 15, 17, or 18. In a particular embodiment, the CAR comprises the CDR sequences (i.e. CDRH1, CDRH2, CDRH3, CDRL1, CDRL2, and CDRL3) of SEQ ID NOs: 2, 6, 9, 11, 14, and 17.

In some embodiments, the CAR further comprises a transmembrane domain. In some embodiments, the transmembrane domain is a CD8 transmembrane domain. However, other transmembrane domains may be used in accordance with the invention. In some embodiments, the CAR further comprises a costimulatory domain and/or a signaling domain. In some embodiments, the costimulatory domain is a 4-1BB costimulatory domain, a CD28 costimulatory domain and/or an OX40 costimulatory domain. In some embodiments, the CAR comprises a signal transduction domain. In some embodiments, the signal transduction domain is a CD3zeta signal transduction domain. In some embodiments, the CD3 zeta signal transduction domain is comprised in the CDR with one or more costimulatory domains (e.g., 41BB, CD28, and/or OX40 costimulatory domains).

Other aspects of the disclosure relate to a nucleic acid comprising a sequence that encodes a CAR as described in any of the above embodiments or as otherwise described herein. In some embodiments, any of the nucleic acid sequences provided herein include one or more features that are useful for improving expression of the CAR. For example, the nucleic acid may include, a 5' untranslated region (5' UTR), a 3' untranslated region (3' UTR), a polyadenine tail (polyA), a 7-methylguanosine cap ($m^7G$), and/or an open reading frame. The nucleic acid may further include an internal ribosome entry site (IRES).

Yet other aspects relate to an mRNA construct suitable for introduction into a cell, e.g., by electroporation as described in any one of the above embodiments or as otherwise described herein. Yet other aspects of the disclosure relate to a vector comprising a nucleic acid as described in any one of the above embodiments or as otherwise described herein. In some embodiments, the vector is lentiviral vector.

Other aspects of the disclosure relate to a cell comprising a CAR and/or a CAR-encoding nucleic acid as described in any one of the above embodiments or as otherwise described herein. In some embodiments, the cell is a stem cell, NK cell, or T cell. In some embodiments, the cell is a T cell.

Other aspects of the disclosure relate to a composition comprising a plurality of a cell (e.g., a T cell) comprising a CAR as described in any one of the above embodiments or as otherwise described herein. In some embodiments, the composition further comprises a pharmaceutically acceptable carrier.

Yet other aspects of the disclosure relate to a method of generating a plurality of CAR modified cells, the method comprising introducing a CAR-encoding nucleic acid described in any one of the above embodiments or as otherwise described herein into a plurality of immune cells by means of electroporation, physical disruption of a cell, e.g., cell squeezing, or by use of a nanoparticle that comprises the nucleic acid. In some embodiments, the immune cells are T cells. In some embodiments, an mRNA construct comprises the CAR-encoding nucleic acid.

Yet other aspects of the disclosure relate to a method of generating a plurality of CAR modified cells, the method comprising introducing a lentiviral vector comprising a nucleic acid as described in any one of the above embodiments or as otherwise described herein into a plurality of immune cells. In some embodiments, one or more lentiviral vectors is provided comprising one or more nucleic acids in any one of the above embodiments or as otherwise described herein. In some embodiments, the immune cells are T cells.

Other aspects of the disclosure relate to a method of treating a subject having cancer or at risk of having cancer, the method comprising administering a T cell comprising a CAR as described in any one of the above embodiments or as otherwise described herein, a composition as described in any one of the above embodiments or as otherwise described herein, or a plurality of cells produced by a method as described in any one of the above embodiments or as otherwise described herein, into a subject having cancer or at risk of having cancer. In some embodiments, the cancer is multiple myeloma.

Also provided are methods of treating a subject having an autoimmune disease or an allergic disorder. Also provided are uses of one or more T cells comprising a CAR, as disclosed herein, for the treatment of cancer, an autoimmune disease, or an allergic disorder.

DEFINITIONS

Figure 1:
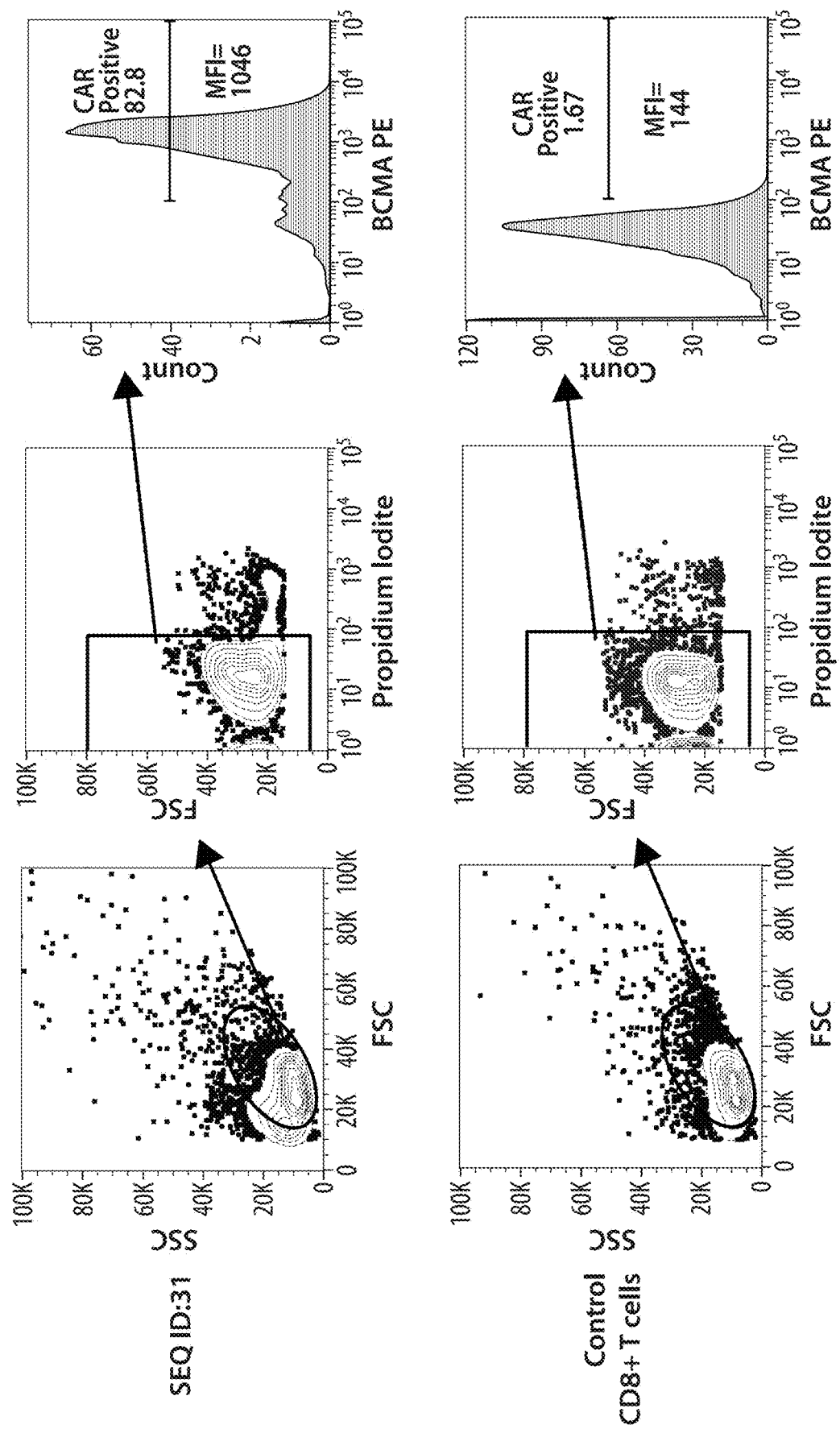
FIG. 1 shows an assessment of cell viability, CAR expression, and BCMA binding by CAR T cells generated with the CAR of SEQ ID: 31 or a control (no mRNA) at 24 hours post transfection.

As used herein and in the claims, the singular forms "a," "an," and "the" include the singular and the plural reference unless the context clearly indicates otherwise. Thus, for example, a reference to "an agent" includes a single agent and a plurality of such agents.

The term "activation", as used herein, refers to the state of a T cell, NK cell, stem cell or other cell that has been sufficiently stimulated to induce detectable cellular proliferation. Activation can also be associated with induced cytokine production, and detectable effector functions. The term "activated T cells" refers to, among other things, T cells that are undergoing cell division.

The terms "allergy" and "allergic", as used herein, refer to a medical condition involving an abnormal hypersensitivity reaction to an ordinarily harmless substance, i.e., an allergen. Exemplary allergic conditions include anaphylaxis, asthma, food allergy, stinging insect allergy, drug allergy, allergic rhinitis, urticaria, angioedema, eczema, atopic dermatitis, contact dermatitis, and eosinophilic esophagitis.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments thereof are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., BCMA). It has been shown that the antigen-binding function of an antibody can be performed by fragments of a full-length antibody. Such antibody embodiments may also be bispecific, dual specific, or multi-specific formats; specifically binding to two or more different antigens. Multispecific, dual specific, and bispecific antibody constructs are well known in the art and described and characterized in Kontermann (ed.), Bispecific Antibodies, Springer, NY (2011), and Spiess et al., Mol. Immunol. 67(2):96-106 (2015).

Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations, kappa and lambda light chains refer to the two major antibody light chain isotypes.

The term "synthetic antibody" as used herein, refers an antibody which is generated using recombinant DNA technology, such as, for example, an antibody expressed by a viral vector. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

In some embodiments, the term "antigen" or "Ag" as used herein is defined as a molecule that provokes an immune response. This immune response may involve either antibody production, or the activation of specific immunologically competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "tumor antigen" as used herein refers to an antigen associated with a cancer cell, such as a multiple myeloma cell. Examples of tumor antigens include but are not limited to BCMA.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autoimmune" refers to a disease or illness wherein an individual's immune system, or a component thereof, attacks that individual's normal body tissue(s). An autoimmune disease can be mediated by an autoantibody, i.e., an antibody produced by an individual that recognizes an antigen of that individual's own tissue(s). Exemplary autoimmune diseases include myasthenia gravis, systemic lupus erythematosus (SLE), rheumatoid arthritis, blistering skin diseases, e.g., pemphigus, psoriasis, inflammatory bowel disease, celiac sprue, pernicious anemia, idiopathic thrombocytopenia purpura, scleroderma, Graves' disease, Sjögren syndrome, Goodpasture syndrome, and type 1 diabetes.

The term "autologous" as used herein, is meant to refer to any material derived from the same individual to which it is later to be re-introduced into the individual.

The term "allogeneic" as used herein refers to a graft derived from a different animal of the same species. "Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In some embodiments, the cancer is a cancer that expresses BCMA. Exemplary cancers that express BCMA include multiple myeloma, Hodgkin lymphoma, non-Hodgkin lymphoma, chronic lymphocytic leukemia (CLL), and glioblastoma. In some embodiments, cancer refers to multiple myeloma. Multiple myeloma is a cancer of plasma cells. Multiple myeloma can be diagnosed with blood tests (serum protein electrophoresis, serum free kappa/lambda light chain assay), bone marrow examination, urine protein electrophoresis, and/or X-rays of commonly involved bones. In some embodiments, cancer refers to Hodgkin's lymphoma (HL). HL is a cancer of B cells.

An "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

As used herein, the term "exogenous" refers to any material introduced from or produced outside an organism, cell, tissue or system.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. An expression vector can provide for a self-amplifying RNA, e.g., by an RNA viral vector. See, e.g., U.S. Ser. No. 12/831,252.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing release of mediators from mast cells and basophils upon exposure to allergen.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence or nucleic acid encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "*Lentivirus*" as used herein refers to a genus of the Retroviridae family. Lenti viruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lenti viruses. Vectors derived from lenti viruses offer the means to achieve significant levels of gene transfer in vivo, ex vivo or in vitro.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Codon-optimized" means that codons relating to a specific amino acid are optimized for translational efficiency of a gene of interest. Codon optimization typically involves evaluating the gene or sequence of interest and substituting the codon with a more prevalent or common codon used for the same amino acid in a specific cell or species. Programs used by those in the art to evaluate codon optimization include those provided by Integrated DNA Technologies, EnCor Biotechnology, Inc., JCat, OptimumGene™ (GenScript USA, Inc., Pisataway, N.J. 08854), etc. The sequences encoding the CAR embodiments described herein may be codon-optimized, which can increase their translational efficiency.

The term "linker," as used herein, refers to a bond (e.g., covalent bond), chemical group, or a molecule linking two molecules or moieties, e.g., two domains of a fusion protein, such as, for example, a nuclease-inactive Cas9 domain and a nucleic acid-editing domain (e.g., an adenosine deaminase). In some embodiments, a linker joins a gRNA binding domain of an RNA-programmable nuclease, including a Cas9 nuclease domain, and the catalytic domain of a nucleic-acid editing protein. In some embodiments, a linker joins a dCas9 and a nucleic-acid editing protein. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" or "overexpression" is intended to indicate an abnormal level of expression (e.g., of the tumor antigen) in a cell from a disease area (e.g., a solid tumor within a specific tissue or organ of the patient) relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In some embodiments, the patient, subject or individual is a human.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner. A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds" or "specific for", as used herein with respect to an antibody (such as a scFv), is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject" is intended to include living organisms in which an immune response can be elicited (e.g., mammals). Examples of subjects include humans, dogs, cats, mice, rats, and transgenic species thereof. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject has cancer (e.g., multiple myeloma). In other embodiments, the subject is a healthy volunteer.

The term "therapeutic" as used herein means a treatment and/or prophylaxis. A therapeutic effect is obtained by suppression, remission, or eradication of a disease state.

The term "therapeutically effective amount" as used herein, refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

DETAILED DESCRIPTION OF CERTAIN EMBODIMENTS

Chimeric antigen receptor (CAR) technology is an anticancer immune therapy approach aimed at generating effector T cells to target specific tumor antigens. CARs are recombinant receptors that provide both antigen-binding and T cell-activating functions. CARs are known in the art and have been described previously, for example in Sadelain M., et al., "The basic principles of chimeric antigen receptor (CAR) design" Cancer Discov. 2013 April; 3(4): 388-398; the entire contents of which are hereby incorporated by reference. In general, CAR T cells (also referred to herein as CART cells or CARTs) are engineered T cells based on a single chain Fv (scFv) antibody moiety. In some embodiments, the chimeric antigen receptor (CAR) portion comprises a receptor complex that combines an antigen binding domain (e.g., scFv) and a signal transduction domain of T cells (such as including the CD3ζ chain).

As provided herein, anti-B-Cell Maturation Antigen (BCMA) CARs, and their corresponding nucleic acid expression constructs, were engineered to confer improved properties including improved expression, improved CAR T cell binding to BCMA, improved half-life, improved killing of BCMA-expressing cells (e.g., myeloma cells), and lower immunogenicity in humans. To generate nucleic acid constructs that express improved anti-BCMA CARs, mutations were made in one or more of the complementarity determining regions (CDRs), mutations were introduced into the open reading frame (ORF), mutations were introduced into the framework region, alternative 5' and 3' untranslated regions (UTRs) were used, alternative costimulatory domains were used, and alternative poly-adenine tails were designed. Such improved anti-BCMA CARs and their expression constructs demonstrate improved properties as compared to previously described anti-BCMA CARs, such as the CAR used in the clinical trial of Ali et al. (2016), i.e., of SEQ ID: 19.

As described herein, CARs were engineered based on scFvs that bind to BCMA, a multiple myeloma (MM) antigen. An exemplary CAR can consist of a CD8 signal peptide, an anti-BCMA scFv (e.g. of SEQ ID NO: 60), a CD8 hinge and transmembrane domain, a 4-1BB costimulatory domain, and CD3ζ signal transduction domain. To generate CAR T cells, mRNA constructs expressing CARs were transfected into CD8+ lymphocytes obtained by apheresis from healthy human donors. CAR T cells expressing one of the CAR proteins tested (e.g., CAR T cells expressing the CAR of SEQ ID NO: 21), demonstrated increased binding to BCMA, increased killing of BCMA-expressing myeloma cells in vitro, and significant inhibition of growth of human myeloma tumors in an animal model. Accordingly, aspects of the invention relate to anti-BCMA CARs and methods of use thereof. In some embodiments, the CAR is expressed by a T cell and is useful for treatment of cancer, e.g., for treatment of multiple myeloma.

In some embodiments, the CAR is specific for BCMA. B cell maturation antigen (BCMA, also known as BCM, CD269, TNFRSF17, or TNFRSF13A) is a member of the TNFR superfamily expressed on B cells. An exemplary, non-limiting human BCMA sequence is provided below.

```
>gi|23238192|ref|NP_001183.2| tumor necrosis
factor receptor superfamily member 17, BCMA
[Homo sapiens]
                                    (SEQ ID NO: 121)
MLQMAGQCSQNEYFDSLLHACIPCQLRCSSNTPPLTCQRYCNASVTNS

VKGTNAILWTCLGLSLIISLAVFVLMFLLRKINSEPLKDEFKNTGSGL

LGMANIDLEKSRTGDEIILPRGLEYTVEECTCEDCIKSKPKVDSDHCF

PLPAMEEGATILVTTKTNDYCKSLPAALSATEIEKSISAR
```

In some embodiments, any of the CARs provided herein comprise a single chain Fv (scFv) that specifically binds to BCMA, which may be on a single polypeptide (e.g., connected by a linker) or on two polypeptides (e.g., one on a first CAR polypeptide and one a second CAR polypeptide, which may form a dimer once introduced into a cell).

Compositions

CARs

In some aspects, the present invention provides a chimeric antigen receptor (CAR) specific for BCMA (e.g., that specifically binds to BCMA). In some embodiments the CAR comprises an antigen-binding domain specific for BCMA, a transmembrane domain and a cytoplasmic domain. In some embodiments, the anti-BCMA binding domain is a humanized anti-BCMA binding domain. In some embodiments, the cytoplasmic domain, or otherwise intracellular domain comprises a T-cell signaling domain, which is capable of transducing a signal, e.g., a T-cell activation signal, in the cell upon binding of the anti-BCMA CAR to a BCMA protein (e.g., a BCMA protein expressed on the surface of a cancer cell). In some embodiments, the T-cell signaling domain is capable of transducing a T-cell proliferation signal, a memory signal, a cytotoxic effector function signal, or a cytokine production signal. In some embodiments, the T-cell signaling domain comprises a costimulatory molecule. In some embodiments, the cytoplasmic domain further comprises a zeta chain portion. Exemplary T-cell signaling domains include, without limitation a CD8-alpha protein, a CD28 protein, a CD3 zeta protein, an FcR gamma protein, a CD27 protein, an OX40 protein, a 41BB protein, and any combination thereof. It should be appreciated, however, that the T-cell signaling domains provided herein are exemplary and the disclosure contemplates additional T-cell signaling domains, known or otherwise yet to be disclosed, that can be used in accordance with the invention.

In some embodiments, between the extracellular domain and the transmembrane domain of the CAR, or between the cytoplasmic domain and the transmembrane domain of the CAR, or between the BCMA-binding domain, there may be incorporated a spacer and/or hinge domain. As used herein, the term "spacer domain" generally refers to any oligo- or polypeptide that functions to link the transmembrane domain to, either the extracellular domain or, the cytoplasmic domain in the polypeptide chain. In some embodiments, a spacer domain may comprise up to 300 amino acids, e.g., 1 to 5 amino acids, 1 to 10 amino acids, 1 to 20 amino acids, 1 to 40 amino acids, 1 to 60 amino acids, 1 to 100 amino acids, 1 to 150 amino acids, 1 to 200 amino acids, 1 to 250 amino acids, 1 to 300 amino acids, 5 to 10 amino acids, 5 to 20 amino acids, 5 to 40 amino acids, 5 to 60 amino acids, 5 to 100 amino acids, 10 to 20 amino acids, 10 to 40 amino acids, 10 to 60 amino acids, 10 to 100 amino acids, 20 to 40 amino acids, 20 to 60 amino acids, 20 to 100 amino acids, 40 to 60 amino acids, 40 to 100 amino acids, or 60 to 100 amino acids. In some embodiments, a spacer domain may comprise 1, 2, 3, 4, 5, 6, 7, 8, 9, 10, 11, 12, 13, 14, 15, 16, 17, 18, 19, 20, 21, 22, 23, 24, or 25 amino acids. It also should be appreciated that one or more spacer domains may be included in other regions of a CAR, as aspects of the disclosure are not limited in this respect. Exemplary spacer sequences include, without limitation one or more of the following GGGGS (SEQ ID NO: 124); GGGGSGGGGS (SEQ ID NO: 125); (GGGGS)₃ (SEQ ID NO: 126); GST-SGGGSGGGSGGGGSS (SEQ ID NO: 127); GST-SGSGKPGSSEGSTKG (SEQ ID NO: 128); GGGGSGGG (SEQ ID NO: 129); and GGGS (SEQ ID NO: 130).

In some embodiments, any of the CARs provided herein comprise a hinge region, which typically connects the extracellular domain to the intracellular domain of a CAR. In some embodiments, the hinge region is between a BCMA-binding domain and a transmembrane domain of a CAR, or between a spacer domain and a transmembrane domain of the CAR. In some embodiments, the transmembrane domain can be attached to the extracellular domain of the CAR, e.g., the anti-BCMA binding domain of the CAR, via a hinge, e.g., a hinge from a human protein. For example, in one embodiment, the hinge can be from a human Ig (immunoglobulin) hinge, e.g., an IgG4 hinge, a CD8α hinge, or a CD28 hinge. In some embodiments, the hinge comprises an amino acid sequence of the hinge of a naturally-occurring Ig molecule, e.g., an IgG4 hinge, a CD8α hinge, or a CD28 hinge, or an amino acid sequence that is at least 75%, 80%, 85%, 90%, 95%, 96%, 97%, 98%, or 99% identical thereto. In some embodiments, the hinge comprises an amino acid sequence that is at least 75%, 80%, 85%, 90%, 95%, 96%, 97%, 98%, or 99% identical to FVPVFLPAKPTTTPA-PRPPTPAPTIASQPLSLRPEACRPAAGGAVHTRGLD-FACD (SEQ ID NO: 117). In some embodiments, the hinge comprises the amino acid sequence of SEQ ID NO: 117. However, it should be appreciated that these examples of hinges are not meant to be limiting and other hinges are contemplated. For Example, a hinge could also include one or more extracellular domains of a cell surface protein. See, e.g., Watanabe et al., "Fine-tuning the CAR spacer improves T-cell potency," Oncoimmunology. 2016; 5(12): e1253656, the contents of which are hereby incorporated by reference.

In some embodiments, any of the CARs provided herein comprise the structure $NH_2$-[BCMA binding domain]-[transmembrane domain]-[cytoplasmic domain]-COOH. In some embodiments, the CAR comprises the structure $NH_2$-[BCMA binding domain]-[hinge region]-[transmembrane domain]-[cytoplasmic domain]-COOH. In some embodiments, the CAR comprises one or more spacer sequences. In some embodiments, each instance of "]-[" indicates the presence of an optional spacer sequence. In some embodiments, the cytoplasmic domain comprises a CD8-alpha protein, a CD28 protein, a CD3 zeta protein, an FcR gamma protein, a CD27 protein, an OX40 protein, a 41BB protein, and any combination thereof. In some embodiments, any of the CARs provided herein comprise the structure [BCMA binding domain]-[transmembrane domain]-[cytoplasmic domain]; [BCMA binding domain]-[hinge region]-[transmembrane domain]-[cytoplasmic domain]; [Signal peptide]-[BCMA binding domain]-[transmembrane domain]-[cytoplasmic domain]; or [Signal peptide]-[BCMA binding domain]-[hinge region]-[transmembrane domain]-[cytoplasmic domain];

In some embodiments, the CAR comprises a cytoplasmic domain having an arrangement selected from one of the following exemplary, non-limiting arrangements:
[CD3zeta];
[CD28]-[CD3zeta];
[41BB]-[CD3zeta];
[OX40]-[CD3zeta]; or
[41BB]-[OX40]-[CD3zeta]

In some embodiments, the above exemplary, non-limiting arrangements are from left to right, N-terminus to C-terminus of the CAR. In some embodiments, each instance of "]-[" indicates the presence of an optional space r sequence.

In one aspect, the anti-BCMA binding domain, e.g., human or humanized scFv, portion of a CAR of the invention is encoded by a transgene whose sequence has been codon optimized for expression in a mammalian cell. In one aspect, entire CAR construct of the invention is encoded by a transgene whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

The disclosure provides nucleic acid sequences coding for any of the molecules provided herein (e.g., anti-BCMA binding proteins, scFvs, CARS, and RNA constructs), which can be obtained using recombinant methods known in the art, such as, for example by screening libraries from cells expressing the gene, by deriving the gene from a vector known to include the same, or by isolating directly from cells and tissues containing the same, using standard techniques. Alternatively, the nucleic acid of interest can be produced synthetically, rather than cloned.

The present invention further includes retroviral and lentiviral vector constructs expressing a CAR that can be directly transduced into a cell.

The present invention also includes an RNA construct that can be directly transfected into a cell. One method for generating mRNA for use in transfection involves in vitro transcription (IVT) of a template with specially designed primers, optionally followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length but described in more detail hereunder. RNA so produced can efficiently transfect different kinds of cells. In one embodiment, the template includes sequences for the CAR. In an embodiment, an RNA CAR vector is transduced into a cell, e.g., T cell or NK cell, by electroporation.

Anti-BCMA Binding Domains

In some embodiments, the CARs provided herein comprise an anti-B-Cell Maturation Antigen (BCMA) binding domain. In some embodiments, the CARs provided herein comprise a BCMA binding domain that is capable of binding to BCMA with greater affinity than other known anti-BCMA binding domains, for example an anti-BCMA binding domain from the CAR used in the clinical trial of Ali et al. (2016), i.e., of SEQ ID: 19. In some embodiments, any of the CARs of the invention can be engineered to target a tumor antigen of interest by way of engineering a desired BCMA binding moiety that specifically binds to a BCMA antigen on a tumor cell. In some embodiments, the anti-BCMA binding domains are N-terminus of to a transmembrane domain and/or intracellular domain of any of the CARs as described herein.

The BCMA binding domain can be any domain that binds to BCMA including but not limited to monoclonal antibodies, scFvs, polyclonal antibodies, synthetic antibodies, human antibodies, humanized antibodies, and antigen binding (e.g., BCMA-binding) fragments thereof. In some embodiments, it is beneficial for the BCMA binding domain to be humanized (e.g., partially humanized or fully humanized). In some instances, it is beneficial for the BCMA binding domain to be derived from the same species in which the CAR will ultimately be used in. For example, for use in humans, it may be beneficial for the BCMA binding domains of the CAR to comprise a human antibody or fragment thereof. Thus, in some embodiments, the BCMA binding domain portion comprises a human antibody or a fragment thereof. For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO98/50433, WO 98/24893, WO98/16654, WO 96/34096, WO 96/33735, and WO91/10741; the contents of each of which is incorporated herein by reference in its entirety. A human antibody can also be an antibody wherein the heavy and light chains are encoded by a nucleotide sequence derived from one or more sources of human DNA. Human or humanized antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

In one aspect, the anti-BCMA binding domain is a fragment, e.g., a single chain variable fragment (scFv) or a fragment from an anti-BCMA antibody. In one aspect, the anti-BCMA binding domain is a Fv, a Fab, a (Fab')2, or a bi-functional (e.g. bi-specific) hybrid antibody (e.g., Lanzavecchia et al., Eur. J. Immunol. 17, 105 (1987)). In one aspect, the antibodies and fragments thereof of the invention binds a BCMA protein with wild-type or enhanced affinity.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, the entire contents of each of which are incorporated by reference herein.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)n$, where n is a positive integer equal to or greater than 1 (SEQ ID NO: 131). In one embodiment, the linker can be $(Gly_4Ser)_4$ (SEQ ID NO: 132) or $(Gly_4Ser)_3$ (SEQ ID NO: 133). In some embodiments, the scFv comprises a linker that is at least 70%, 75%, 80%, 85%, 90%, 95%, 96%, 97%, 98%, or 99% identical to the amino acid sequence of GSTSGSGKPGSGEGSTKG (SEQ ID NO: 108), or GSTSGSGKPGSGEG-STKGSGGGSGGG (SEQ ID NO:109). In some embodiments, the scFv comprises a linker that that comprises the amino acid sequence of SEQ ID NO: 108 or 109.

Antibodies directed against an antigen (e.g., BCMA) can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For a detailed discussion of this technology for producing human antibodies and human monoclonal antibodies and protocols for producing such antibodies, see, e.g., PCT Publication Nos. WO2014/055771, WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. A "humanized" antibody retains a similar antigenic specificity as the original antibody, i.e., in the present invention, the ability to bind, for example, BCMA.

In some embodiments, antibodies (e.g., antibodies used to make BCMA binding domains), are tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain typically includes an N-terminal variable (V) domain ($V_L$) and a constant (C) domain ($C_L$). Each heavy chain typically includes an N-terminal V domain ($V_H$), three or four C domains ($C_H1$-3), and a hinge region. The $C_H$ domain most proximal to $V_H$ is designated as $C_H1$. The $V_H$ and $V_L$ domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as CDRH1, CDRH2, and CDRH3, while CDR constituents on the light chain are referred to as CDRL1, CDRL2, and CDRL3. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) J. Mol. Biol. 227:799-817; and Tomlinson et al. (1995) EMBO J. 14:4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops, or combinations of any of these methods.

CAR T cells provided herein are capable of binding to BCMA with greater affinity and/or more efficiently kill-BCMA expressing cells (e.g., myeloma cells) than other CAR T cells known in the art, e.g., the CAR T cells used in the clinical trial of Ali et al. (2016), i.e., of a CAR of SEQ ID: 19. In some embodiments, anti-BCMA binding domains provided herein can bind to BCMA with an affinity that is at least 5%, 10%, 15%, 20%, 30%, 40%, 50%, 60%, 70%, 80%, 90%, 100%, 120%, 140%, 160%, 180%, 200%, 250%, 300%, 350%, 400%, 450%, 500%, 600%, 700%, 800%, 900%, or 1,000% greater than the affinity of another anti-BCMA binding domain to BCMA, e.g., the BCMA binding domain from the CAR used in the clinical trial of Ali et al. (2016), i.e., of SEQ ID: 19. In some embodiments, anti-BCMA binding domains provided herein, when comprised in a CAR expressed on a T cell, can kill cancer cells (e.g., BCMA expressing myeloma cells) more efficiently (e.g., at least 5%, 10%, 15%, 20%, 30%, 40%, 50%, 60%, 70%, 80%, 90%, 100%, 120%, 140%, 160%, 180%, 200%, 250%, 300%, 350%, 400%, 450%, 500%, 600%, 700%, 800%, 900%, or 1,000% more efficiently) than another anti-BCMA CAR, e.g., the CAR used in the clinical trial of Ali et al. (2016), i.e., of SEQ ID: 19. Exemplary CDR sequences used in anti-BCMA binding domains are provided below. Those amino acid residues that are different with respect to the reference CDR sequences (i.e., SEQ ID NOs: 1, 4, 7, 10, 12, and 16) are indicated by bold and underlining.

```
CDRH1:
                              (SEQ ID NO: 1)
DYSIN;

(SEQ ID NO: 2)
SYSIN;

(SEQ ID NO: 3)
SYDIN

CDRH2:
                              (SEQ ID NO: 4)
WINTETREPAYAYDFRG;

(SEQ ID NO: 5)
WINTNTGNPTYAQFFTG;

(SEQ ID NO: 6)
WINTETREPAYAQGFTG

CDRH3:
                              (SEQ ID NO: 7)
DYSYAMDY;

(SEQ ID NO: 8)
DYTYGMDY;

(SEQ ID NO: 9)
DYLYSLDF

CDRL1:
                              (SEQ ID NO: 10)
RASESVTILGSHLIH;

(SEQ ID NO: 11)
RASESVSFLGINLIH
```

```
CDRL2:
                              (SEQ ID NO: 12)
QLASNVQT;

(SEQ ID NO: 13)
YLASNLET;

(SEQ ID NO: 14)
YSASNLQS;

(SEQ ID NO: 15)
NLASNVNT

CDRL3:
                              (SEQ ID NO: 16)
LQSRTIPRT;

(SEQ ID NO: 17)
LQSRTLPRT;

(SEQ ID NO: 18)
LQSKNFPRT
```

In some embodiments, the anti-BCMA binding domain comprises at least one (e.g., at least 2, 3, 4, 5, or 6 CDR sequences) CDR sequence selected from any one of SEQ ID NOs: 2, 3, 5, 6, 8, 9, 11, 13, 14, 15, 17, and 18. In some embodiments, the anti-BCMA binding domain comprises at least one of the CDRH1 amino acid sequences of any one of SEQ ID NOs: 1-3. In some embodiments, the anti-BCMA binding domain comprises at least one of the CDRH2 amino acid sequences of any one of SEQ ID NOs: 4-6. In some embodiments, the anti-BCMA binding domain comprises at least one of the CDRH3 amino acid sequences of any one of SEQ ID NOs: 7-9. In some embodiments, the anti-BCMA binding domain comprises at least one of the CDRL1 amino acid sequences of any one of SEQ ID NOs: 10-11. In some embodiments, the anti-BCMA binding domain comprises at least one of the CDRL2 amino acid sequences of any one of SEQ ID NOs: 12-15. In some embodiments, the anti-BCMA binding domain comprises at least one of the CDRL3 amino acid sequences of any one of SEQ ID NOs: 16-18. In some embodiments, the anti-BCMA binding domain comprises the CDRH3 of SEQ ID NO: 8 or 9. In some embodiments, the anti-BCMA binding domain comprises the CDRL3 of SEQ ID NO: 17 or 18.

In some embodiments, the anti-BCMA binding domain includes a CDRH1, CDRH2, CDRH3, CDRL1, CDRL2, or CDRL3, or combinations thereof, as provided for any one of the scFv clones shown in Table 1. In some embodiments, anti-BCMA binding domains include the CDRH1, CDRH2, CDRH3, CDRL1, CDRL2, and CDRL3 of any one of the scFv clones shown in Table 1. The disclosure also includes any nucleic acid sequence that encodes a molecule comprising a CDRH1, CDRH2, CDRH3, CDRL1, CDRL2, or CDRL3 as provided for any one of the scFv clones shown in Table 1. Antibody heavy and light chain CDR3 domains may play a particularly important role in the binding specificity/affinity of an antibody for an antigen. Accordingly, the anti-BCMA binding domains of the disclosure, may include at least the heavy and/or light chain CDR3s of antibodies as shown in Table 1. Aspects of the disclosure relate to anti-BCMA biding domains that bind to BCMA protein (e.g., a BCMA protein on a tumor cell) and that comprises six complementarity determining regions (CDRs): CDRH1, CDRH2, CDRH3, CDRL1, CDRL2, and CDRL3.

TABLE 1

Combination of CDR sequences (CDRH 1-3 and CDRL 1-3) for each scFv used in the CARs provided herein. The parent framework region used for each scFv is also indicated by the parent framework of the indicated SEQ ID NOs. Each CDR is indicated by their SEQ ID NO.

| New scFv | Parent Framework SEQ ID NO: | CDRH 1 SEQ ID NO: | CDRH 2 SEQ ID NO: | CDRH 3 SEQ ID NO: | CDRL 1 SEQ ID NO: | CDRL 2 SEQ ID NO: | CDRL 3 SEQ ID NO: |
|---|---|---|---|---|---|---|---|
| R1  | 48 | 1  | 4  | 7  | 10  | 12  | 16  |
| Y32 | 57 | 1  | 4  | 7  | 10  | 12  | 16  |
| Y37 | 60 | 1  | 4  | 7  | 10  | 12  | 16  |
| 1'  | 57 | 3* | 4  | 7  | 10  | 12  | 16  |
| 4'  | 57 | 1  | 4  | 8* | 10  | 12  | 16  |
| 8'  | 57 | 1  | 4  | 7  | 11* | 14* | 17* |
| 9'  | 57 | 1  | 4  | 7  | 11* | 14* | 18* |
| 10' | 57 | 2* | 6* | 9* | 10  | 12  | 16  |
| 11' | 57 | 3* | 5* | 8* | 10  | 12  | 16  |
| 12' | 57 | 3* | 4  | 9* | 10  | 12  | 18* |
| 13' | 57 | 2* | 6* | 9* | 11* | 13* | 17* |
| 21' | 57 | 1  | 4  | 7  | 10  | 15* | 16  |
| K'  | 60 | 2* | 6* | 9* | 11* | 14* | 17* |
| R'  | 60 | 2* | 6* | 9* | 11* | 14* | 17* |
| J'  | 60 | 2* | 6* | 9* | 11* | 14* | 18* |
| L'  | 60 | 2* | 6* | 9* | 11* | 14* | 18* |
| O'  | 60 | 1  | 4  | 8* | 10  | 15* | 17* |
| S'  | 60 | 1  | 4  | 8* | 10  | 15* | 17* |

Those SEQ ID NOs marked with an "*" are different from the reference CDR sequences of SEQ ID NOs: 1, 4, 7, 10, 12, and 16.

In some embodiments, the anti-BCMA binding domain comprises six complementarity determining regions (CDRs): CDRH1, CDRH2, CDRH3, CDRL1, CDRL2, and CDRL3. In some embodiments, the anti-BCMA binding domain comprises any one of the following groups of CDRs, which are listed in the order of CDRH1, CDRH2, CDRH3, CDRL1, CDRL2, and CDRL3:
SEQ ID NOs: 3, 4, 7, 10, 12, and 16;
SEQ ID NOs: 1, 4, 8, 10, 12, and 16;
SEQ ID NOs: 1, 4, 7, 11, 14, and 17;
SEQ ID NOs: 1, 4, 7, 11, 14, and 18;
SEQ ID NOs: 2, 6, 9, 10, 12, and 16;
SEQ ID NOs: 3, 5, 8, 10, 12, and 16;
SEQ ID NOs: 3, 4, 9, 10, 12, and 18;
SEQ ID NOs: 2, 6, 9, 11, 13, and 17;
SEQ ID NOs: 1, 4, 7, 10, 15, and 16;
SEQ ID NOs: 2, 6, 9, 11, 14, and 17;
SEQ ID NOs: 2, 6, 9, 11, 14, and 18;
SEQ ID NOs: 1, 4, 8, 10, 15, and 17; and
SEQ ID NOs: 1, 4, 7, 10, 12, and 16.

It should be appreciated that the disclosure contemplates any of the CDR sequences provided herein (e.g., SEQ ID NOs: 1-18) having 1, 2, or 3, but no more than three conservative mutations. Accordingly, in some embodiments, any of the CDR sequences provided herein, i.e., any of the CDH1, CDH2, CDH3, CDL1, CDL2, or CDL3, CDR sequences provided herein, may comprise 1, 2 or 3 conservative mutations. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the anti-BCMA binding domain comprises a heavy chain variable domain and/or a light chain variable domain. In some embodiments, the anti-BCMA binding domain comprises a heavy chain variable domain framework sequence that is at least 75% (e.g., 80%, 85%, 90%, 95%, 98%, or 99%) identical to the heavy chain variable domain framework sequence from the scFv of any one of SEQ ID NOs: 48-72 or a light chain variable domain framework sequence from the scFv of any one of SEQ ID NOs: 48-72. In some embodiments, the homologous heavy chain variable domain framework sequence and/or a light chain variable domain framework sequence do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein. In the scFv amino acid sequences provided below (SEQ ID NOs 48-72), the heavy chain variable sequence is indicated in bold, the light chain variable sequence is indicated in italics, and the linker sequence is indicated by underlining. In some embodiments, the anti-BCMA binding domain comprises a single chain variable fragment (scFv) made up of a variable heavy chain (VH) and a variable light chain (VL). In some embodiments, the anti-BCMA binding domain comprises the amino acid sequence of any one of SEQ ID NOs 48-72.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

scFv-R1
(SEQ ID NO: 48)
DIVLTQSPPSLAMSLGKRATISCRASESVTILGSHLIHWYQQKPGQPP

TLLIQLASNVQTGVPARFSGSGSRTDFTLTIDPVEEDDVAVYYCLQSR

TIPRTFGGGTKLEIK<u>GSTSGSGKPGSGEGSTKG</u>QIQLVQSGPELKKPG

ETVKISCKASGYTFTDYSINWVKRAPGKGLKWMGWINTETREPAYAYD

FRGRFAFSLETSASTAYLQINNLKYEDTATYFCALDYSYAMDYWGQGT

SVTVSS scFv-J1
(SEQ ID NO: 49)
DIVMTQSPDSLSVSLGERATINCRASESVTILGSHLIHWYQQKPGQPP

KLLIQLASNVQTGVPDRFSGSGSGTDFTLTISSLQAEDVAVYYCLQSR

TIPRTFGGGTKVEIK<u>GSTSGSGKPGSGEGSTKG</u>QIQLVQSGAEVKKPG

ASVKISCKASGYTFTDYSINWVRQAPGQGLEWMGWINTETREPAYAYD

FRGRVTMTRDTSASTAYLQISSLKAEDTAVYFCALDYSYAMDYWGQGS

LVTVSS scFv-J2
(SEQ ID NO: 50)
DIVLTQSPASLAVSLGERATISCRASESVSILGSHLLHWYQQKPGQPP

KLLIYLASNLQTGVPARFSGSGSGTDFTLTISSLEAEDVAVYYCLQSR

TIPRTFGQGTKLEIK<u>GSTSGSGKPGSGEGSTKG</u>QIQLVQSGAEVKKPG

ASVKISCKASGYTFTDYSINWVRQAPGQGLEWMGWINTETREPAYAYD

FRGRVTMTRDTSASTAYLQISSLKAEDTAVYFCALDYSYAMDYWGQGS

LVTVSS scFv-J3
(SEQ ID NO: 51)
DIVLTQSPASLAVSLGKRATISCRASESVTILGSHLIHWYQQKPGQPP

KLLIYLASNVQTGVPARFSGSGSGTDFTLTISSLEAEDVAVYYCLQSR

TIPRTFGQGTKLEIK<u>GSTSGSGKPGSGEGSTKG</u>QVQLVQSGAEVKKPG

ASVKISCKASGYTFTDYSINWVRQAPGQGLEWMGWINTETREPAYAYD

FRGRVTMTRDTSASTAYLQISSLKAEDTAVYFCALDYSYAMDYWGQGS

LVTVSS scFv-J4
(SEQ ID NO: 52)
DIVMTQSPDSLSVSLGERATINCRASESVTILGSHLIHWYQQKPGQPP

KLLIQLASNVQTGVPDRFSGSGSGTDFTLTISSLQAEDVAVYYCLQSR

TIPRTFGGGTKVEIK<u>GSTSGSGKPGSGEGSTKG</u>QIQLVQSGAEVKKPG

ESVKISCKASGYTFTDYSINWVRQAPGQGLKWMGWINTETREPAYAYD

FRGRFAFSLDTSASTAYLQISSLKAEDTAVYFCALDYSYAMDYWGQGT

LVTVSS scFv-J5
(SEQ ID NO: 53)
DIVLTQSPASLAVSLGERATISCRASESVSILGSHYLAWYQQKPGQPP

KLLIYLASNLQTGVPARFSGSGSGTDFTLTISSLEAEDVAVYYCQQSR

TIPRTFGQGTKLEIK<u>GSTSGSGKPGSGEGSTKG</u>QIQLVQSGAEVKKPG

ESVKISCKASGYTFTDYSINWVRQAPGQGLKWMGWINTETREPAYAYD

FRGRFAFSLDTSASTAYLQISSLKAEDTAVYFCALDYSYAMDYWGQGT

LVTVSS scFv-Yi1
(SEQ ID NO: 54)
DIVLTQSPSSLSASVGDRATISCRASESVTILGSHLIHWYQQKPGQAP

KLLIQLASNVQTGVPARFSGSGSGTDFTLTISSVEPDDVAVYYCLQSR

TIPRTFGGGTKLEIK<u>GSTSGSGKPGSGEGSTKG</u>QIQLVQSGPELKKPG

GSVKISCAASGYTFTDYSINWVKQAPGKGLEWVGWINTETREPAYAYD

FRGRFTFSLDTSKSTAYLQMNSLRAEDTAVYYCALDYSYAMDYWGQGT

LVTVSS scFv-Yi2
(SEQ ID NO: 55)
DIQLTQSPSSLSASVGDRVTITCRASQSVTILGSHLIHWYQQKPGKAP

KLLIQLASNVQTGVPSRFSGSGSGTDFTLTISSLQPEDVATYYCLQSR

TIPRTFGQGTKLEIK<u>GSTSGSGKPGSGEGSTKG</u>QVQLVQSGGGLVQPG

RSVKLSCAASGYTFTDYSINWVRQAPGKGLEWVGWINTETREPAYAYD

FRGRFTISRDTSKNTAYLQMNSLRAEDTAVYYCARDYSYAMDYWGQGT

LVTVSS scFv-Y31
(SEQ ID NO: 56)
DIVLTQSPSSLSASVGDRATISCRASESVTILGSHLIHWYQQKPGQAP

KLLIQLASNVQTGVPARFSGSGSGTDFTLTISSVEPEDVAVYYCLQSR

TIPRTFGQGTKVEIK<u>GSTSGSGKPGSGEGSTKG</u>QIQLVQSGPELKKPG

GSVKISCAASGYTFTDYSINWVKQAPGKGLEWVGWINTETREPAYAYD

FRGRFTFSADTSKSTAYLQMNSLRAEDTAVYYCALDYSYAMDYWGQGT

LVTVSS scFv-Y32
(SEQ ID NO: 57)
DIVLTQSPSSLSASVGDRATISCRASESVTILGSHLIHWYQQKPGQAP

KLLIQLASNVQTGVPARFSGSGSGTDFTLTISSVEPEDVAVYYCLQSR

TIPRTFGQGTKVEIK<u>GSTSGSGKPGSGEGSTKG</u>QIQLVQSGPELKKPG

GSVKISCAASGYTFTDYSINWVRQAPGKGLEWVGWINTETREPAYAYD

FRGRFTFSADTSKSTAYLQMNSLRAEDTAVYYCALDYSYAMDYWGQGT

LVTVSS scFv-Y33
(SEQ ID NO: 58)
DIVLTQSPSSLSASVGDRATISCRASESVTILGSHLIHWYQQKPGQAP

KLLIQLASNVQTGVPARFSGSGSGTDFTLTISSVEPEDVAVYYCLQSR

TIPRTFGQGTKVEIK<u>GSTSGSGKPGSGEGSTKG</u>QIQLVESGAEVKKPG

GSVKISCAASGYTFTDYSINWVKQAPGKGLEWVGWINTETREPAYAYD

FRGRFTFSLDTSKSTAYLQMNSLRAEDTAVYYCALDYSYAMDYWGQGT

LVTVSS scFv-Y34
(SEQ ID NO: 59)
DIVLTQSPSSLSASVGDRATISCRASESVTILGSHLIHWYQQKPGQAP

KLLIQLASNVQTGVPARFSGSGSGTDFTLTISSVEPEDVAVYYCLQSR

TIPRTFGQGTKVEIK<u>GSTSGSGKPGSGEGSTKG</u>QIQLVESGAEVKKPG

GSVKVSCKASGYTFTDYSINWVRQAPGKGLEWVGWINTETREPAYAYD

FRGRFAISAETSKSTAYLQMNSLRAEDTAVYYCALDYSYAMDYWGQGT

LVTVSS scFv-Y37
(SEQ ID NO: 60)
DIVLTQSPASLAVSPGQRATITCRASESVTILGSHLIHWYQQKPGQPP

KLLIQLASNVQTGVPARFSGSGSGTDFTLTISSVEPEDTANYYCLQSR

TIPRTFGQGTKVEIK<u>GSTSGSGKPGSGEGSTKG</u>QIQLVQSGPELKKPG

GSVKISCKASGYTFTDYSINWVRQAPGKGLEWVGWINTETREPAYAYD

FTGRFTFSADTSKSMAYLQINSLRAEDTAVYYCALDYSYAMDYWGQGT

LVTVSS scFv-CAS2 (C2)
(SEQ ID NO: 61)
DIVLTQSPASLAVSPGQRATITCRASESVTILGSHLIHWYQQKPGQPP

KLLIQLASNVQTGVPARFSGSGSRTDFTLTISSLEPEDVAVYYCLQSR

TIPRTFGQGTKVEIK<u>GSTSGSGKPGSGEGSTKG</u>QITLKESGPTLVKPT

QTLTLSCKASGYTFTDYSINWVRRAPGKGLEWMGWINTETREPAYAYD

FRGRFVFSLDTSVSMAYLQISSLKAEDTAVYYCALDYSYAMDYWGQGT

LVTVSS scFv-1'
(SEQ ID NO: 62)
DIVLTQSPSSLSASVGDRATISCRASESVTILGSHLIHWYQQKPGQAP

KLLIQLASNVQTGVPARFSGSGSGTDFTLTISSVEPEDVAVYYCLQSR

TIPRTFGQGTKVEIK<u>GSTSGSGKPGSGEGSTKG</u>QIQLVQSGPELKKPG

GSVKISCAASGYTFTSYDINWVRQAPGKGLEWVGWINTETREPAYAYD

FRGRFTFSADTSKSTAYLQMNSLRAEDTAVYYCALDYSYAMDYWGQGT

LVTVSS scFv-4'
(SEQ ID NO: 63)
DIVLTQSPSSLSASVGDRATISCRASESVTILGSHLIHWYQQKPGQAP

KLLIQLASNVQTGVPARFSGSGSGTDFTLTISSVEPEDVAVYYCLQSR

TIPRTFGQGTKVEIK<u>GSTSGSGKPGSGEGSTKG</u>QIQLVQSGPELKKPG

GSVKISCAASGYTFTDYSINWVRQAPGKGLEWVGWINTETREPAYAYD

FRGRFTFSADTSKSTAYLQMNSLRAEDTAVYYCALDYTYGMDYWGQGT

LVTVSS scFv-8'
(SEQ ID NO: 64)
DIVLTQSPSSLSASVGDRATISCRASESVSFLGINLIHWYQQKPGQAP

KLLIYSASNLQSGVPARFSGSGSGTDFTLTISSVEPEDVAVYYCLQSR

TLPRTFGQGTKVEIK<u>GSTSGSGKPGSGEGSTKG</u>QIQLVQSGPELKKPG

GSVKISCAASGYTFTDYSINWVRQAPGKGLEWVGWINTETREPAYAYD

FRGRFTFSADTSKSTAYLQMNSLRAEDTAVYYCALDYSYAMDYWGQGT

LVTVSS scFv-9'
(SEQ ID NO: 65)
DIVLTQSPSSLSASVGDRATISCRASESVSFLGINLIHWYQQKPGQAP

KLLIYSASNLQSGVPARFSGSGSGTDFTLTISSVEPEDVAVYYCLQSK

NFPRTFGQGTKVEIK<u>GSTSGSGKPGSGEGSTKG</u>QIQLVQSGPELKKPG

GSVKISCAASGYTFTDYSINWVRQAPGKGLEWVGWINTETREPAYAYD

FRGRFTFSADTSKSTAYLQMNSLRAEDTAVYYCALDYSYAMDYWGQGT

LVTVSS scFv-10'
(SEQ ID NO: 66)
DIVLTQSPSSLSASVGDRATISCRASESVTILGSHLIHWYQQKPGQAP

KLLIQLASNVQTGVPARFSGSGSGTDFTLTISSVEPEDVAVYYCLQSR

TIPRTFGQGTKVEIK<u>GSTSGSGKPGSGEGSTKG</u>QIQLVQSGPELKKPG

GSVKISCAASGYTFTSYSINWVRQAPGKGLEWVGWINTETREPAYAQG

FTGRFTFSADTSKSTAYLQMNSLRAEDTAVYYCALDYLYSLDFWGQGT

LVTVSS scFv-11'
(SEQ ID NO: 67)
DIVLTQSPSSLSASVGDRATISCRASESVTILGSHLIHWYQQKPGQAP

KLLIQLASNVQTGVPARFSGSGSGTDFTLTISSVEPEDVAVYYCLQSR

TIPRTFGQGTKVEIK<u>GSTSGSGKPGSGEGSTKG</u>QIQLVQSGPELKKPG

GSVKISCAASGYTFTSYDINWVRQAPGKGLEWVGWINTNTGNPTYAQG

FTGRFTFSADTSKSTAYLQMNSLRAEDTAVYYCALDYTYGMDYWGQGT

LVTVSS scFv-12'
(SEQ ID NO: 68)
DIVLTQSPSSLSASVGDRATISCRASESVTILGSHLIHWYQQKPGQAP

KLLIQLASNVQTGVPARFSGSGSGTDFTLTISSVEPEDVAVYYCLQSK

NFPRTFGQGTKVEIK<u>GSTSGSGKPGSGEGSTKG</u>QIQLVQSGPELKKPG

GSVKISCAASGYTFTSYDINWVRQAPGKGLEWVGWINTETREPAYAYD

FRGRFTFSADTSKSTAYLQMNSLRAEDTAVYYCALDYLYSLDFWGQGT

LVTVSS scFv-13'
(SEQ ID NO: 69)
DIVLTQSPSSLSASVGDRATISCRASESVSFLGINLIHWYQQKPGQAP

KLLIYLASNLETGVPARFSGSGSGTDFTLTISSVEPEDVAVYYCLQSR

TLPRTFGQGTKVEIK<u>GSTSGSGKPGSGEGSTKG</u>QIQLVQSGPELKKPG

GSVKISCAASGYTFTSYSINWVRQAPGKGLEWVGWINTETREPAYAQG

FTGRFTFSADTSKSTAYLQMNSLRAEDTAVYYCALDYLYSLDFWGQGT

LVTVSS scFv-21'
(SEQ ID NO: 70)
DIVLTQSPSSLSASVGDRATISCRASESVTILGSHLIHWYQQKPGQAP

```
                                      -continued
KLLINLASNVNTGVPARFSGSGSGTDFTLTISSVEPEDVAVYYCLQSR

TIPRTFGQGTKVEIKGSTSGSGKPGSGEGSTKGQIQLVQSGPELKKPG

GSVKISCAASGYTFTDYSINWVRQAPGKGLEWVGWINTETREPAYAYD

FRGRFTFSADTSKSTAYLQMNSLRAEDTAVYYCALDYSYAMDYWGQGT

LVTVSS scFv-2'
                                               (SEQ ID NO: 71)
DIVLTQSPSSLSASVGDRATISCRASESVTILGSHLIHWYQQKPGQAP

KLLIQLASNVQTGVPARFSGSGSGTDFTLTISSVEPEDVAVYYCLQSR

TLPRTFGQGTKVEIKGSTSGSGKPGSGEGSTKGQIQLVQSGPELKKPG

GSVKISCAASGYTFTDYSINWVRQAPGKGLEWVGWINTETREPAYAYD

FRGRFTFSADTSKSTAYLQMNSLRAEDTAVYYCALDYSYAMDYWGQGT

LVTVSS scFv-3'
                                               (SEQ ID NO: 72)
DIVLTQSPSSLSASVGDRATISCRASESVTILGSHLIHWYQQKPGQAP

KLLIQLASNVQTGVPARFSGSGSGTDFTLTISSVEPEDVAVYYCLQSR

TLPRTFGQGTKVEIKGSTSGSGKPGSGEGSTKGQIQLVQSGPELKKPG

GSVKISCAASGYTFTDYSINWVRQAPGKGLEWVGWINTETREPAYAYD

FRGRFTFSADTSKSTAYLQMNSLRAEDTAVYYCALDYSYAMDYWGQGT

LVTVSS
```

Leader Domains

In some embodiments, a CAR is designed with a leader domain (also referred to as a "signal peptide") for directing the translated chimeric protein to the membrane. In some embodiments the CAR comprises a leader sequence at the amino-terminus (N-ter) of the CAR protein. In one aspect, the CAR further comprises a leader sequence at the N-terminus of the extracellular BCMA binding domain, wherein the leader sequence is optionally cleaved from the BCMA binding domain (e.g., scFv) during cellular processing and localization of the CAR to the cellular membrane. The leader domain is generally in the range of 15 to 30 amino acids. Examples of leader domains include a CD8a leader (21 amino acids), a CD33 leader (17 amino acids), a CD4 leader (25 amino acids), a IL-2R (CD25) leader (21 amino acids), a trypsinogen-2 leader (15 amino acids), a VEGFR1 leader (26 amino acids), a EGFR leader (24 amino acids) a GMCSFR leader (22 amino acids), a IgVL leader, a IgVK leader, or a Ig VH leader. In some embodiments, the leader sequence is at least 80%, 90%, 95%, 96%, 97%, 98%, or 99% identical to any of the leader domains provided herein. In some embodiments, the leader sequence is at least 80%, 85%, 90%, 95%, 96%, 97%, 98%, or 99% identical to the amino acid sequence of MALPVTALLLPLALLLHAARP (SEQ ID NO: 110). In some embodiments, the leader sequence comprises the amino acid sequence of SEQ ID NO: 110.

Transmembrane and Hinge Domains

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the CAR-expressing cell, e.g., CAR T cell, surface. In a different aspect the amino acid sequence of the transmembrane domain may be modified or substituted so as to minimize interactions with the binding domains of the native binding partner present in the same CAR-expressing cell, e.g., CAR T cell.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of a costimulatory molecule, e.g., MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. Transmembrane domains can be identified using any method known in the art or described herein, e.g., by using the UniProt Database.

In some embodiments, the transmembrane domain may be synthetic, in which case it will comprise predominantly hydrophobic residues such as leucine and valine. In some embodiments, a triplet of phenylalanine, tryptophan and valine will be found at each end of a synthetic transmembrane domain. Optionally, a short oligo- or polypeptide linker, e.g., between 2 and 10 amino acids in length may form the linkage between the transmembrane domain and the cytoplasmic signaling domain of the CAR. A glycine-serine doublet provides an exemplary suitable linker.

In some embodiments, the transmembrane domain in the CAR of the invention is a CD8 transmembrane domain. Sequences of CD8 for this purpose are taught in PCT Pub No. WO2014/055771, which is incorporated by reference herein. In some embodiments, the transmembrane domain in the CAR is a CD8a transmembrane. In some embodiments, the transmembrane domain comprises the amino acid sequence of IYIWAPLAGTCGVLLLSLVIT (SEQ ID NO 118), IYIWAPLAGTCGVLLLSLVITLYCNHRN (SEQ ID NO: 120), or an amino acid sequence that is at least 70%, 75%, 80%, 85%, 90%, 95%, 96%, 97%, 98%, or 99% identical thereto. It should be appreciated that a portion of the transmembrane domain may be extracellular or cytosolic, for example, in some embodiments, the transmembrane domain comprises a cytosolic portion comprising the amino acid sequence of LYCNHRN (SEQ ID NO: 119).

In some embodiments, the transmembrane domain in the CAR of the invention is the CD28 transmembrane domain. One skilled in the art would appreciate that the full transmembrane domain, or portion thereof, is implemented with the cytoplasmic domain, or a portion thereof. Typically, the transmembrane and cytoplasmic domains used would be contiguous portions of the CD28 sequence. In some embodiments, the CD28 transmembrane domain comprises a fragment or variant thereof that is capable of anchoring a CAR comprising the sequence to a cell membrane.

In some instances, the transmembrane domain is attached to the extracellular region of the CAR, e.g., the antigen binding domain of the CAR, via a hinge, e.g., a hinge from a human protein. For example, in one embodiment, the hinge can be a human Ig (immunoglobulin) hinge, e.g., an IgG4 hinge, or a CD8a hinge. In one embodiment, the hinge or spacer comprises (e.g., consists of) the amino acid sequence of FVPVFLPAKPTTTPAPRPPTPAPTIASQPLSLRPEACRPAAGGAVHTRGLDFACD (SEQ ID NO: 117), or an amino acid sequence that is at least 70%, 75%, 80%, 85%, 90%, 95%, 96%, 97%, 98%, or 99% identical thereto. In one aspect, the transmembrane and hinge domains comprise (e.g., consists of) the amino acid sequence of FVPVFLPAKPTTTPAPRPPTPAPTIASQPLSLRPEACRPAAGGAVHTRGLDFACDIYIWAPLAGTCGVLLLSLVITLYCNHRN (SEQ ID NO: 111).

Cytoplasmic Domain

Some aspects of the disclosure provide CARs having a cytoplasmic domain (also referred to as an intracellular domain or intracellular signaling domain). The cytoplasmic domain or region of a CAR of the present invention includes an intracellular signaling domain. An intracellular signaling domain is generally responsible for activation of at least one of the normal effector functions of the immune cell in which the CAR has been introduced. In some embodiments, the cytoplasmic domain of the CAR is responsible for activation of at least one of the normal effector functions of the immune cell in which the CAR has been introduced in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire domain. To the extent that a truncated portion of the intracellular signaling domain is used, such truncated portion may be used in place of the intact domain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, CD278 (also known as "ICOS"), Fc.epsilon.RI, DAP10, DAP12, and CD66d. In one embodiment, a CAR of the invention comprises an intracellular signaling domain, e.g., a primary signaling domain of CD3zeta. An exemplary CD3zeta signaling domain is provided below.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs. Further examples of molecules containing a primary intracellular signaling domain include those of DAP10, DAP12, and CD32.

The intracellular signaling domain of the CAR can comprise a primary signaling domain, e.g., CD3-zeta signaling domain, by itself or it can be combined with any other desired intracellular signaling domain(s) useful in the context of a CAR of the invention. For example, the intracellular signaling domain of the CAR can comprise a primary signaling domain, e.g., CD3 zeta chain portion, and one or more costimulatory signaling domains. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, and the like. For example, CD27 costimulation has been demonstrated to enhance expansion, effector function, and survival of human CAR T cells in vitro and augments human T cell persistence and antitumor activity in vivo (Song et al. Blood. 2012; 119(3):696-706). The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. Exemplary costimulatory domains are provided below. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

Exemplary CD3zeta Signaling Domain:

```
                                          (SEQ ID NO: 107)
RVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR
```

Exemplary Costimulatory Domains:

```
CD28
                                          (SEQ ID NO: 100)
RSKRSRLLHSDYMNMTPRRPGPTRKHYQPYAPPRDFAAYRS

41BB
                                          (SEQ ID NO: 101)
KRGRKKLLYIFKQPFMRPVQTTQEEDGCSCRFPEEEEGGCEL

OX40
                                          (SEQ ID NO: 102)
RRDQRLPPDAHKPPGGGSFRTPIQEEQADAHSTLAKI
```

Exemplary Combinations of Signaling and Costimulatory Domains

```
CD28-CD3zeta
                                          (SEQ ID NO: 103)
RSKRSRLLHSDYMNMTPRRPGPTRKHYQPYAPPRDFAAYRSRVKFSRS

ADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDA

LHMQALPPR

41BB-CD3zeta
                                          (SEQ ID NO: 104)
KRGRKKLLYIFKQPFMRPVQTTQEEDGCSCRFPEEEEGGCELRVKFSR

SADAPAYQQGQNQLYNELNLGRREEYDVLDKRRGRDPEMGGKPRRKNP

QEGLYNELQKDKMAEAYSEIGMKGERRRGKGHDGLYQGLSTATKDTYD

ALHMQALPPR

OX40-CD3zeta
                                          (SEQ ID NO: 105)
RRDQRLPPDAHKPPGGGSFRTPIQEEQADAHSTLAKIRVKFSRSADAP

AYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQ

ALPPR

41BB-OX40-CD3zeta
                                          (SEQ ID NO: 106)
KRGRKKLLYIFKQPFMRPVQTTQEEDGCSCRFPEEEEGGCELRRDQRL

PPDAHKPPGGGSFRTPIQEEQADAHSTLAKIRVKFSRSADAPAYQQGQ

NQLYNELNLGRREEYDVLDKRRGRDPEMGGKPRRKNPQEGLYNELQKD

KMAEAYSEIGMKGERRRGKGHDGLYQGLSTATKDTYDALHMQALPPR
```

The cytoplasmic domain of the CAR can be designed to comprise the CD3-zeta signal transduction domain by itself or combined with any other desired cytoplasmic domain(s) useful in the context of the CAR of the invention, such as a 4-1BB domain, a CD28 domain, and/or an OX40 domain. For example, the cytoplasmic domain of the CAR can comprise a CD3 zeta chain portion and a costimulatory signaling region. The costimulatory signaling region refers to a portion of the CAR comprising the intracellular domain of a costimulatory molecule. Thus, while the invention is exemplified primarily with 4-1BB, CD28, and OX40 as the costimulatory or signaling element(s), other additional costimulatory or signaling elements are within the scope of the invention. Exemplary sequences of costimulatory and intracellular domains are provided herein. Other exemplary 4-1BB costimulatory domains are described in US Patent Publication US20050113564, which is incorporated by reference herein.

In some embodiments, any of the CARs provided herein comprise a CD3zeta signaling domain. In some embodiments, the CD3zeta domain is derived from a human. In some embodiments, the CD3zeta domain comprises an amino acid sequence that is at least 70%, 75%, 80%, 85%, 90%, 95%, 96%, 97%, 98%, or 99% identical to the amino acid sequence of SEQ ID NO: 107. In some embodiments, the CD3zeta domain comprises the amino acid sequence of SEQ ID NO: 107.

In some embodiments, any of the CARs provided herein comprise one or more (e.g., 2, 3, 4, or 5) costimulatory domains. In some embodiments, any of the CARs provided herein comprise a CD28, a 41BB, and/or an OX40 costimulatory domain. In some embodiments, the costimulatory domain is derived from a human. In some embodiments, the CAR comprises one or more of the amino acid sequences of any of SEQ ID NOs: 100-102, or any variants thereof that are at least 70%, 75%, 80%, 85%, 90%, 95%, 96%, 97%, 98%, or 99% identical thereto. It should be appreciated that the cytoplasmic domain of the car may comprise any combination of signaling and/or cytoplasmic domains. For example, the cytoplasmic domain may comprise any of the following exemplary combination of domains: CD28-CD3zeta; 41BB-CD3zeta; OX40-CD3zeta; or 41BB-OX40-CD3zeta. In some embodiments, the cytoplasmic domain of the CAR comprises the amino acid sequence of any of SEQ ID NOs: 103-106, or any variants thereof that are at least 70%, 75%, 80%, 85%, 90%, 95%, 96%, 97%, 98%, or 99% identical thereto.

Exemplary Full-Length CARs

As provided herein, the disclosure contemplates CARx comprising an anti-BCMA binding domain (e.g., human or humanized BCMA binding domain as described herein), a transmembrane domain, and a cytoplasmic domain. It should be appreciated that any of the CARs provided herein can be produced using any combination of domains or peptides described herein, for example the CAR can comprise any anti-BCMA binding domain, transmembrane, cytoplasmic domain, signal peptide, or hinge region provided herein. Exemplary CARs and variants thereof are provided below.

CAR-R1
(SEQ ID NO: 19)
MALPVTALLLPLALLLHAARPDIVLTQSPPSLAMSLGKRATISCRASE
SVTILGSHLIHWYQQKPGQPPTLLIQLASNVQTGVPARFSGSGSRTDF
TLTIDPVEEDDVAVYYCLQSRTIPRTFGGGTKLEIKGSTSGSGKPGSG
EGSTKGQIQLVQSGPELKKPGETVKISCKASGYTFTDYSINWVKRAPG
KGLKWMGWINTTETREPAYAYDFRGRFAFSLETSASTAYLQINNLKYE
DTATYFCALDYSYAMDYWGQGTSVTVSSFVPVFLPAKPTTTPAPRPPT
PAPTIASQPLSLRPEACRPAAGGAVHTRGLDFACDIYIWAPLAGTCGV
LLLSLVITLYCNHRNRSKRSRLLHSDYMNMTPRRPGPTRKHYQPYAPP
RDFAAYRSRVKFSRSADAPAYQQGQNQLYNELNLGRREEYDVLDKRRG
RDPEMGGKPRRKNPQEGLYNELQKDKMAEAYSEIGMKGERRRGKGHDG
LYQGLSTATKDTYDALHMQALPPR

CAR-K'
(SEQ ID NO: 20)
MALPVTALLLPLALLLHAARPDIVLTQSPASLAVSPGQRATITCRASE
SVSFLGINLIHWYQQKPGQPPKLLIYSASNLQSGVPARFSGSGSGTDF
TLTISSVEPEDTANYYCLQSRTLPRTFGQGTKVEIKGSTSGSGKPGSG
EGSTKGQIQLVQSGPELKKPGGSVKISCKASGYTFTSYSINWVRQAPG
KGLEWVGWINTETREPAYAQGFTGRFTFSADTSKSMAYLQINSLRAED
TAVYYCALDYLYSLDFWGQGTLVTVSSFVPVFLPAKPTTTPAPRPPTP
APTIASQPLSLRPEACRPAAGGAVHTRGLDFACDIYIWAPLAGTCGVL
LLSLVITLYCNHRNRVKFSRSADAPAYQQGQNQLYNELNLGRREEYDV
LDKRRGRDPEMGGKPRRKNPQEGLYNELQKDKMAEAYSEIGMKGERRR
GKGHDGLYQGLSTATKDTYDALHMQALPPR

CAR-R'
(SEQ ID NO: 21)
MALPVTALLLPLALLLHAARPDIVLTQSPASLAVSPGQRATITCRASE
SVSFLGINLIHWYQQKPGQPPKLLIYSASNLQSGVPARFSGSGSGTDF
TLTISSVEPEDTANYYCLQSRTLPRTFGQGTKVEIKGSTSGSGKPGSG
EGSTKGQIQLVQSGPELKKPGGSVKISCKASGYTFTSYSINWVRQAPG
KGLEWVGWINTETREPAYAQGFTGRFTFSADTSKSMAYLQINSLRAED
TAVYYCALDYLYSLDFWGQGTLVTVSSFVPVFLPAKPTTTPAPRPPTP
APTIASQPLSLRPEACRPAAGGAVHTRGLDFACDIYIWAPLAGTCGVL
LLSLVITLYCNHRNKRGRKKLLYIFKQPFMRPVQTTQEEDGCSCRFPE
EEEGGCELRVKFSRSADAPAYQQGQNQLYNELNLGRREEYDVLDKRRG
RDPEMGGKPRRKNPQEGLYNELQKDKMAEAYSEIGMKGERRRGKGHDG
LYQGLSTATKDTYDALHMQALPPR

CAR-J'
(SEQ ID NO: 22)
MALPVTALLLPLALLLHAARPDIVLTQSPASLAVSPGQRATITCRASE
SVSFLGINLIHWYQQKPGQPPKLLIYSASNLQSGVPARFSGSGSGTDF
TLTISSVEPEDTANYYCLQSKNFPRTFGQGTKVEIKGSTSGSGKPGSG
EGSTKGQIQLVQSGPELKKPGGSVKISCKASGYTFTSYSINWVRQAPG
KGLEWVGWINTETREPAYAQGFTGRFTFSADTSKSMAYLQINSLRAED
TAVYYCALDYLYSLDFWGQGTLVTVSSFVPVFLPAKPTTTPAPRPPTP
APTIASQPLSLRPEACRPAAGGAVHTRGLDFACDIYIWAPLAGTCGVL
LLSLVITLYCNHRNRVKFSRSADAPAYQQGQNQLYNELNLGRREEYDV
LDKRRGRDPEMGGKPRRKNPQEGLYNELQKDKMAEAYSEIGMKGERRR
GKGHDGLYQGLSTATKDTYDALHMQALPPR

CAR-L'
(SEQ ID NO: 23)
MALPVTALLLPLALLLHAARPDIVLTQSPASLAVSPGQRATITCRASE
SVSFLGINLIHWYQQKPGQPPKLLIYSASNLQSGVPARFSGSGSGTDF
TLTISSVEPEDTANYYCLQSKNFPRTFGQGTKVEIKGSTSGSGKPGSG
EGSTKGQIQLVQSGPELKKPGGSVKISCKASGYTFTSYSINWVRQAPG
KGLEWVGWINTETREPAYAQGFTGRFTFSADTSKSMAYLQINSLRAED
TAVYYCALDYLYSLDFWGQGTLVTVSSFVPVFLPAKPTTTPAPRPPTP
APTIASQPLSLRPEACRPAAGGAVHTRGLDFACDIYIWAPLAGTCGVL
LLSLVITLYCNHRNKRGRKKLLYIFKQPFMRPVQTTQEEDGCSCRFPE
EEEGGCELRVKFSRSADAPAYQQGQNQLYNELNLGRREEYDVLDKRRG
RDPEMGGKPRRKNPQEGLYNELQKDKMAEAYSEIGMKGERRRGKGHDG
LYQGLSTATKDTYDALHMQALPPR

CAR-O'
(SEQ ID NO: 24)
MALPVTALLLPLALLLHAARPDIVLTQSPASLAVSPGQRATITCRASE
SVTILGSHLIHWYQQKPGQPPKLLINLASNVNTGVPARFSGSGSGTDF

-continued
TLTISSVEPEDTANYYCLQSRTLPRTFGQGTKVEIKGSTSGSGKPGSG

EGSTKGQIQLVQSGPELKKPGGSVKISCKASGYTFTDYSINWVRQAPG

KGLEWVGWINTETREPAYAYDFTGRFTFSADTSKSMAYLQINSLRAED

TAVYYCALDYTYGMDYWGQGTLVTVSSFVPVFLPAKPTTTPAPRPPTP

APTIASQPLSLRPEACRPAAGGAVHTRGLDFACDIYIWAPLAGTCGVL

LLSLVITLYCNHRNRVKFSRSADAPAYQQGQNQLYNELNLGRREEYDV

LDKRRGRDPEMGGKPRRKNPQEGLYNELQKDKMAEAYSEIGMKGERRR

GKGHDGLYQGLSTATKDTYDALHMQALPPR

CAR-S'
(SEQ ID NO: 25)
MALPVTALLLPLALLLHAARPDIVLTQSPASLAVSPGQRATITCRASE

SVTILGSHLIHWYQQKPGQPPKLLINLASNVQTGVPARFSGSGSGTDF

TLTISSVEPEDTANYYCLQSRTLPRTFGQGTKVEIKGSTSGSGKPGSG

EGSTKGQIQLVQSGPELKKPGGSVKISCKASGYTFTDYSINWVRQAPG

KGLEWVGWINTETREPAYAYDFTGRFTFSADTSKSMAYLQINSLRAED

TAVYYCALDYTYGMDYWGQGTLVTVSSFVPVFLPAKPTTTPAPRPPTP

APTIASQPLSLRPEACRPAAGGAVHTRGLDFACDIYIWAPLAGTCGVL

LLSLVITLYCNHRNKRGRKKLLYIFKQPFMRPVQTTQEEDGCSCRFPE

EEEGGCELRVKFSRSADAPAYQQGQNQLYNELNLGRREEYDVLDKRRG

RDPEMGGKPRRKNPQEGLYNELQKDKMAEAYSEIGMKGERRRGKGHDG

LYQGLSTATKDTYDALHMQALPPR

CAR-II
(SEQ ID NO: 26)
MALPVTALLLPLALLLHAARPDIVLTQSPSSLSASVGDRATISCRASE

SVTILGSHLIHWYQQKPGQAPKLLIQLASNVQTGVPARFSGSGSGTDF

TLTISSVEPEDVAVYYCLQSRTIPRTFGQGTKVEIKGSTSGSGKPGSG

EGSTKGQIQLVQSGPELKKPGGSVKISCAASGYTFTDYSINWVRQAPG

KGLEWVGWINTETREPAYAYDFRGRFTFSADTSKSTAYLQMNSLRAED

TAVYYCALDYSYAMDYWGQGTLVTVSSFVPVFLPAKPTTTPAPRPPTP

APTIASQPLSLRPEACRPAAGGAVHTRGLDFACDIYIWAPLAGTCGVL

LLSLVITLYCNHRNRVKFSRSADAPAYQQGQNQLYNELNLGRREEYDV

LDKRRGRDPEMGGKPRRKNPQEGLYNELQKDKMAEAYSEIGMKGERRR

GKGHDGLYQGLSTATKDTYDALHMQALPPR

CAR-10dU
(SEQ ID NO: 27)
MALPVTALLLPLALLLHAARPDIVLTQSPSSLSASVGDRATISCRASE

SVTILGSHLIHWYQQKPGQAPKLLIQLASNVQTGVPARFSGSGSGTDF

TLTISSVEPEDVAVYYCLQSRTIPRTFGQGTKVEIKGSTSGSGKPGSG

EGSTKGQIQLVQSGPELKKPGGSVKISCAASGYTFTDYSINWVRQAPG

KGLEWVGWINTETREPAYAYDFRGRFTFSADTSKSTAYLQMNSLRAED

TAVYYCALDYSYAMDYWGQGTLVTVSSFVPVFLPAKPTTTPAPRPPTP

APTIASQPLSLRPEACRPAAGGAVHTRGLDFACDIYIWAPLAGTCGVL

LLSLVITLYCNHRNRVKFSRSADAPAYQQGQNQLYNELNLGRREEYDV

LDKRRGRDPEMGGKPRRKNPQEGLYNELQKDKMAEAYSEIGMKGERRR

GKGHDGLYQGLSTATKDTYDALHMQALPPR

CAR-17'
(SEQ ID NO: 28)
MALPVTALLLPLALLLHAARPDIVLTQSPASLAVSPGQRATITCRASE

SVTILGSHLIHWYQQKPGQPPKLLIQLASNVQTGVPARFSGSGSGTDF

TLTISSVEPEDTANYYCLQSRTIPRTFGQGTKVEIKGSTSGSGKPGSG

EGSTKGQIQLVQSGPELKKPGGSVKISCKASGYTFTDYSINWVRQAPG

KGLEWVGWINTETREPAYAYDFTGRFTFSADTSKSMAYLQINSLRAED

TAVYYCALDYSYAMDYWGQGTLVTVSSFVPVFLPAKPTTTPAPRPPTP

APTIASQPLSLRPEACRPAAGGAVHTRGLDFACDIYIWAPLAGTCGVL

LLSLVITLYCNHRNRVKFSRSADAPAYQQGQNQLYNELNLGRREEYDV

LDKRRGRDPEMGGKPRRKNPQEGLYNELQKDKMAEAYSEIGMKGERRR

GKGHDGLYQGLSTATKDTYDALHMQALPPR

In some embodiments, the full-length amino acid sequence of the CAR is at least 60%, at least 65%, at least 70%, at least 75%, at least 80%, at least 85%, at least 90%, at least 95%, at least 96%, at least 97%, at least 98%, at least 99%, or at least 99.5% identical to any one of the amino acid sequences set forth in any one of SEQ ID NOs: 19-28, or to any of the CARs provided herein. In some embodiments, the CAR comprises an amino acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50, or more mutations compared to any one of the amino acid sequences set forth in SEQ ID NOs: 19-28, or any of the fusion proteins provided herein. In some embodiments, the CAR comprises an amino acid sequence that has at least 5, at least 10, at least 15, at least 20, at least 25, at least 30, at least 35, at least 40, at least 45, at least 50, at least 60, at least 70, at least 80, at least 90, at least 100, at least 110, at least 120, at least 130, at least 140, at least 150, at least 160, at least 170, at least 200, at least 300, at least 400, or at least 500 identical contiguous amino acid residues as compared to any one of the amino acid sequences set forth in SEQ ID NOs: 19-28, or any of the fusion proteins provided herein.

Nucleic Acids and Vectors

In some embodiments, the present invention encompasses a nucleic acid molecule (e.g., DNA or RNA) that encodes a CAR (e.g., any of the CARs provided herein). In some embodiments, the nucleic acid molecule is a DNA. In some embodiments, the nucleic acid molecule is an RNA. In some embodiments, the nucleic acid molecule comprises the sequence of a CAR, wherein the sequence comprises a nucleic acid sequence that encodes an antigen binding domain (e.g., an anti-BCMA binding domain) operably linked to the nucleic acid sequence encoding one or more of an extracellular domain, a transmembrane domain, and an intracellular domain. In some embodiments, the nucleic acid molecule encodes a CAR having an arrangement selected from one of the following exemplary, non-limiting arrangements:

[antigen binding domain]-[transmembrane domain]-[cytoplasmic domain];
[antigen binding domain]-[hinge region]-[transmembrane domain]-[cytoplasmic domain];

[Signal peptide]-[antigen binding domain]-[transmembrane domain]-[cytoplasmic domain];
or
[Signal peptide]-[antigen binding domain]-[hinge region]-[transmembrane domain]-[cytoplasmic domain];

In some embodiments, the nucleic acid sequence of the CAR comprises a cytoplasmic domain having an arrangement selected from one of the following exemplary, non-limiting arrangements:
[CD3zeta];
[CD28]-[CD3zeta];
[41BB]-[CD3zeta];
[OX40]-[CD3zeta]; or
[41BB]-[OX40]-[CD3zeta]

In some embodiments, the above exemplary, non-limiting arrangements are from left to right, N-terminus to C-terminus of the CAR. In some embodiments, each instance of "]-[" indicates the presence of an optional spacer sequence.

It should be appreciated that any of the nucleic acid molecules provided herein may encode, or include other features, for example a 5' untranslated region (5' UTR), a 3' untranslated region (3' UTR), a poly-adenine tail (polyA), a 7-methylguanosine cap ($m^7G$), an internal ribosome entry site (IRES) and/or an open reading frame. In some embodiments, the disclosure provides an RNA having the following arrangement of features, or a DNA that encodes the same:
5'-[5' UTR]-[CAR]-3'
5'-[$m^7G$ cap]-[5' UTR]-[CAR]-3'
5'-[$m^7G$ cap]-[5' UTR]-[CAR]-[polyA]-3'
5'-[CAR]-[3' UTR]-[polyA]-3'
5'-[5' UTR]-[CAR]-[3' UTR]-3'
5'-[5' UTR]-[CAR]-[3' UTR]-[polyA]-3'
5'-[$m^7G$ cap]-[5' UTR]-[CAR]-[3' UTR]-[PolyA]-3'

In some embodiments, the nucleic acids provided include chemical structures with the ability to promote stability and/or translation efficiency. In some embodiments, the RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

In some embodiments, the 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5' UTR of an RNA virus whose RNA genome is stable in cells. In other embodiments various nucleotide analogues can be used in the 3' or 5' UTR to impede exonuclease degradation of the mRNA.

In some embodiments, the disclosure provides 5' and/or 3' UTRs that are particularly useful for expressing CARs in cells (e.g., a T cell). In some embodiments, the 5' UTR is a 5' UTR from Yi1, IgG, CD8, Myo, CD3, AFP, Actin, IFNG, ACTBL2, a synthetic sequence, or a variant thereof. In some embodiments, the 5' UTR is from a human or mouse. Exemplary 5' UTR sequences are provided below. In some embodiments, the 5' UTR comprises a nucleic acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the nucleic acid sequences set forth in any one of SEQ ID NOs: 73-82. In some embodiments, the 5' UTR comprises a nucleic acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, or more mutations compared to any one of the nucleic acid sequences set forth in SEQ ID NOs: 71-82. In some embodiments, the 5' UTR comprises a nucleic acid sequence that has at least 5, at least 10, at least 15, at least 20, at least 25, at least 30, at least 35, at least 40, at least 45, or at least 50 identical contiguous nucleotides as compared to any one of the nucleic acid sequences set forth in SEQ ID NOs: 71-82.

5' UTR-Yi1
(SEQ ID NO: 73)
GGGAGACCCAAGCTGGCTAGCCTCGCAGTTCGGCGGTCCCGCGGGTCT

GTCTGTTGCTTCAACAGTGTTTGGACGGAACAGATCCGGGGACTCTCT

TCCAGCC

5' UTR-IgG
(SEQ ID NO: 74)
AGACCCAAGCTGGCTAGCTCTAAAGAAGCCCCTGGGAGCACAGCTCAT

CACC

5' UTR-CD8
(SEQ ID NO: 75)
AGACCCAAGCTGGCTAGCAGCTCCTCACCCACCCCAGCCGCGACTGTC

TCCGCCGAGCCCCCGGGGCCAGGTGTCCCGGGCGCGCCCCG

5' UTR-Myo
(SEQ ID NO: 76)
GTGGAACACTTCTGAACCTGCATTTTTATCTGGAACTCCAGAAGCAGA

ATCCTTTGCTAAATAAATCGCAGCC

5' UTR-CD3
(SEQ ID NO: 77)
AGAGAAGCAGACATCTTCTAGTTCCTCCCCCACTCTCCTCTTTCCGGT

ACCTGTGAGTCAGCTAGGGGAGGGCAGCTCTCACCCAGGCTGATAGTT

CGGTGACCTGGCTTTATCTACTGGATGAGTTCCGCTGGGAG

5' UTR-AFP
(SEQ ID NO: 78)
AGACCCAAGCTGGCTAGCATATTGTGCTTCCACCACTGCCAATAACAA

AATAACTAGCAACC

```
5' UTR-R1 synthetic sequence
                                              (SEQ ID NO: 79)
AAATAAGAGAGAAAAGAAGAGTAAGAAGAAATATAAGAGCCACC 5' UTR-Actin
                                              (SEQ ID NO: 80)
CGCGTCCGCCCCGCGAGCACAGAGCCTCGCCTTTGCCGATCCGCCGCC

CGTCCACACCCGCCGCCAGCTCACC

5' UTR-IFNG
                                              (SEQ ID NO: 81)
CACATTGTTCTGATCATCTGAAGATCAGCTATTAGAAGAGAAAGATCA

GTTAAGTCCTTTGGACCTGATCAGCTTGATACAAGAACTACTGATTTC

AACTTCTTTGGCTTAATTCTCTCGGAAACG

5' UTR-ACTBL2
                                              (SEQ ID NO: 82)
GTGTCTGAAAGCATTTCTGGAGTGTTTTAGGCCTGTTCACTTTCTCTT

ACTCACTGTCTATTCACTTGTCCTGTTCACTCGTCTGGAAGATCTCAG

CCAGCACC
```

In some embodiments, the disclosure provides 3' UTRs that are particularly useful for expressing CARs in cells (e.g., a T cell). In some embodiments, the 3' UTR is a 3' UTR from human beta globin, IgG, Actin, AFP, CD3, IFNG, Myo, FoxP3, GAPDH, GATA3, H2AFV, RORC, SOC2, mouse alpha globin, GATA3, or a variant thereof. In some embodiments, the 3' UTR is from a human or mouse. Exemplary 3' UTR sequences are provided below. In some embodiments, the 3' UTR comprises a nucleic acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the nucleic acid sequences set forth in any one of SEQ ID NOs: 83-99. In some embodiments, the 3' UTR comprises a nucleic acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, or more mutations compared to any one of the nucleic acid sequences set forth in SEQ ID NOs: 83-99. In some embodiments, the 3' UTR comprises a nucleic acid sequence that has at least 5, at least 10, at least 15, at least 20, at least 25, at least 30, at least 35, at least 40, at least 45, or at least 50 identical contiguous nucleotides as compared to any one of the nucleic acid sequences set forth in SEQ ID NOs: 83-99.

```
3' UTR-Human beta globin
                                              (SEQ ID NO: 83)
GGGCCCGTTTAAACCCGCTGGCTCGCTTTCTTGCTGTCCAATTTCTATTAAAGGTTC

CTTTGTTCCGTAAGTCCAACTACTAAACTGGGGGATATTATGAAGGGCCTTGAGCA

TCTGGATTCTGCCTAATAAAAAACATTTATTTTCATTGC

3' UTR-IgG
                                              (SEQ ID NO: 84)
TGAGTGCGACGGCCGGCAAGCCCCCGCTCCCCGGGCTCTCGCGGTCGCACGAGG

ATGCTTGGCACGTACCCCGTGTACATACTTCCCGGGCGCCCAGCATGGAAATAAAG

CACCCAGCGCTGCCCTGGGCCCCTGCG

3' UTR-Actin
                                              (SEQ ID NO: 85)
GCGGACTATGACTTAGTTGCGTTACACCCTTTCTTGACAAAACCTAACTTGCGCAG

AAAACAAGATGAGATTGGCATGGCTTTATTTGTTTTTTTGTTTTGTTTTGGTTTTT

TTTTTTTTTTGGCTTGACTCAGGATTTAAAAACTGGAACGGTGAAGGTGACAGCA

GTCGGTTGGAGCGAGCATCCCCCAAAGTTCTCAATGTGGCCGAGGACTTTGATTG

CACATTGTTGTTTTTTAATAGTCATTCCAAATATGAGATGCGTTGTTACAGGAAGT

CCCTTGCCATCCTAAAAGCCACCCCACTTCTCTCTAAGGAGAATGGCCCAGTCCTC

TCCCAAGTCCACACAGGGGAGGTGATAGCATTGCTTTCGTGTAAATTATGTAATGC

AAAATTTTTTAATCTTCGCCTTAATACTTTTTATTTTGTTTTATTTTGAATGATGAG

CCTTCGTGCCCCCCCTTCCCCCTTTTTTGTCCCCCAACTTGAGATGTATGAAGGCTT

TTGGTCTCCCTGGGAGTGGGTGGAGGCAGCCAGGGCTTACCTGTACACTGACTTG

AGACCAGTTGAATAAAAGTGCACACCTT

3' UTR-AFP
                                              (SEQ ID NO: 86)
ATTACTTCAGGGGAAGAGATGACAAAACGAGTCTTTCATTCGGTGTGAACTTTTCT

CTTTAATTTTAACTGATTTAACACTTTTTGTGAATTAATGAAATGATAAAGACTTTTA

TGTGAGATTTCCTTATCACAGAAATAAAATATCTCCAAATGTTTCCTTTTC
```

-continued

3' UTR-CD3
(SEQ ID NO: 87)
ACCTGAGACTGGTGGCTTCTAGAAGCAGCCATTACCAACTGTACCTTCCCTTCTTG

CTCAGCCAATAAATATATCCTCTTTCACTCAG

3' UTR-IFNG
(SEQ ID NO: 88)
TGGTTGTCCTGCCTGCAATATTTGAATTTTAAATCTAAATCTATTTATTAATATTTAAC

ATTATTTATATGGGGAATATATTTTTAGACTCATCAATCAAATAAGTATTTATAATAGC

AACTTTTGTGTAATGAAAATGAATATCTATTAATATATGTATTATTTATAATTCCTATAT

CCTGTGACTGTCTCACTTAATCCTTTGTTTTCTGACTAATTAGGCAAGGCTATGTGA

TTACAAGGCTTTATCTCAGGGGCCAACTAGGCAGCCAACCTAAGCAAGATCCCAT

GGGTTGTGTGTTTATTTCACTTGATGATACAATGAACACTTATAAGTGAAGTGATAC

TATCCAGTTACTGCCGGTTTGAAAATATGCCTGCAATCTGAGCCAGTGCTTTAATG

GCATGTCAGACAGAACTTGAATGTGTCAGGTGACCCTGATGAAAACATAGCATCT

CAGGAGATTTCATGCCTGGTGCTTCCAAATATTGTTGACAACTGTGACTGTACCCA

AATGGAAAGTAACTCATTTGTTAAAATTATCAATATCTAATATATATGAATAAAGTGT

AAGTTCACAAC

3' UTR-Myo
(SEQ ID NO: 89)
ACACACCTGCCTGATGCTATCAAGAGGCTGAAGAAAGCGCCAAATGTGCTATTTTT

TGGTCACTTGCTTTATGACGTTTATTTTCCTGTTAAAGCTGAATAAATAAAAACTAC

AGTAAATGTA

3' UTR-FoxP3
(SEQ ID NO: 90)
CCTCAAGATCAAGGAAAGGAGGATGGACGAACAGGGGCCAAACTGGTGGGAGG

CAGAGGTGGTGGGGGCAGGGATGATAGGCCCTGGATGTGCCCACAGGGACCAAG

AAGTGAGGTTTCCACTGTCTTGCCTGCCAGGGCCCCTGTTCCCCCGCTGGCAGCC

ACCCCCTCCCCCATCATATCCTTTGCCCCAAGGCTGCTCAGAGGGGCCCCGGTCCT

GGCCCCAGCCCCCACCTCCGCCCCAGACACACCCCCCAGTCGAGCCCTGCAGCC

AAACAGAGCCTTCACAACCAGCCACACAGAGCCTGCCTCAGCTGCTCGCACAGA

TTACTTCAGGGCTGGAAAAGTCACACAGACACACAAAATGTCACAATCCTGTCCC

TCACTCAACACAAACCCCAAAACACAGAGAGCCTGCCTCAGTACACTCAAACAA

CCTCAAAGCTGCATCATCACACAATCACACACAAGCACAGCCCTGACAACCCACA

CACCCCAAGGCACGCACCCACAGCCAGCCTCAGGGCCCACAGGGGCACTGTCAA

CACAGGGGTGTGCCCAGAGGCCTACACAGAAGCAGCGTCAGTACCCTCAGGATC

TGAGGTCCCAACACGTGCTCGCTCACACACACGGCCTGTTAGAATTCACCTGTGT

ATCTCACGCATATGCACACGCACAGCCCCCCAGTGGGTCTCTTGAGTCCCGTGCA

GACACACACAGCCACACACACTGCCTTGCCAAAAATACCCCGTGTCTCCCCTGCC

ACTCACCTCACTCCCATTCCCTGAGCCCTGATCCATGCCTCAGCTTAGACTGCAGA

GGAACTACTCATTTATTTGGGATCCAAGGCCCCCAACCCACAGTACCGTCCCCAAT

AAACTGCAGCCGAGCTCCCCAC

3' UTR-GAPDH
(SEQ ID NO: 91)
GAAGTCTGTTCCTGTCCTCCCTGTGCAGGGTATCCTGTAGGGTGACCTGGAATTCG

AATTCTGTTTCCCTTGTAAAATATTTGTCTGTCTCTTTTTT

3' UTR-GATA3 (ORF sequence)
(SEQ ID NO: 92)
CTATGAAGAAGGAAGGCATCCAGACCAGAAACCGAAAAATGTCTAGCAAATCCA

AAAAGTGCAAAAAAGTGCATGACTCACTGGAGGACTTCCCCAAGAACAGCTCGT

TTAACCCGGCCGCCCTCTCCAGACACATGTCCTCCCTGAGCCACATCTCGCCCTTC

AGCCACTCCAGCCACATGCTGACCACGCCCACGCCGATGCACCCGCCATCCAGC

3' UTR-H2AFV
(SEQ ID NO: 93)
AGGGATGCTTTAACCAACCCTCTTCCTCCCCGTCATTGTACTGTAACTGGGACAGA

AGAAATAATGGGGATATGTGGAATTTTTAACAACAGTTAAATGGAAAAGCATAGAC

AATTACTGTAGACATGATAAAAGAAACATTTGTATGTTCTTAGACTCGAAGTTTGAT

AAAAGTACCTTTTCATGTGGTGACAGTTGTGTGTTGATTGGCTAGGTTTCTCCCGT

GTGTTTATACAAAAATGGAATTGATAAACCATTTTTTACAAAATTAATTTGTCTCA

AAACTGTTCTGTTCATGATGTATTAGAAATATTTTACTCAGACTTTAAATATTTTAAA

TCTCAGATTGGTTATTCAGAGTAACCTTAGAACAGAAATTGGGAATATATCTTTACA

ATGATTGATACCATGGTATATTGACTCTTAGATGCTATTGATCTGTAGCACCATTTTT

TACAAACGACTAAGGAAAAAACCTGCCAATTAAATCATGATATGCCATCAATTATG

AGACATCCCAATTTGAGAGATGTTAGATTATAGAAAAGTATGCATTTATGACTGAA

ATGGTAGTGGAATTATTTGAATTCTACACCAAGCACTTACCATGTGCCAGGCCCTTT

GCAGAGTGCTCTACTGACCAAGAAAGTTGTTGCTGCCACATTATAGATGTGGAGC

CTAAGGGTCACAGAAATTGTGTGCTATGCCAAAAAACATTGAACTGGTAGATAGA

AAATGACAGAGCTAGGATTCAAACCTAGATCTGGCTGACTCCAGAGCCTAGTTTTA

CCTGGAATTGATGTTCAGTTTATCAAAGGTTTCTCCTTTTGGTTTAAAATCCCAATT

TTTGGCCTGGCATTGTGGTTTACGCCTGTAATCCCAACAC

3' UTR-RORC
(SEQ ID NO: 94)
CCTGGAAGAGGGACTCCTTGCCTCTCCCTATGGCCTGCTGGCCCACCTCCCTGGA

CCCCGTTCCACCCTCACCCTTTTCCTTTCCCATGAACCCTGGAGGGTGGTCCCCAC

CAGCTCTTTGGAAGTGAGCAGATGCTGCGGCTGGCTTTCTGTCAGCAGGCCGGCC

TGGCAGTGGGACAATCGCCAGAGGGTGGGGCTGGCAGAACACCATCTCCAGCCT

CAGCTTTGACCTGTCTCATTTCCCATATTCCTTCACACCCAGCTTCTGGAAGGCATG

GGGTGGCTGGGATTTAAGGACTTCTGGGGGACCAAGACATCCTCAAGAAAACAG

GGGCATCCAGGGCTCCCTGGATGAATAGAATGCAATTCATTCAGAAGCTCAGAAG

CTAAGAATAAGCCTTTGAAATACCTCATTGCATTTCCCTTTGGGCTTCGGCTTGGG

GAGATGGATCAAGCTCAGAGACTGGCAGTGAGAGCCCAGAAGGACCTGTATAAA

ATGAATCTGGAGCTTTACATTTTCTGCCTCTGCCTTCCTCCCAGCTCAGCAAGGAA

GTATTTGGGCACCCTACCCTTTACCT

3' UTR-SOD2
(SEQ ID NO: 95)
ACCACGATCGTTATGCTGATCATACCCTAATGATCCCAGCAAGATAATGTCCTGTCC

TCTAAGATGTGCATCAAGCCTGGTACATACTGAAAACCCTATAAGGTCCTGGATAA

TTTTTGTTTGATTATTCATTGAAGAAACATTTATTTTCCAATTGTGTGAAGTTTTTGA

CTGTTAATAAAAGAATCTGTCAACCATCAAAGAGGTCTGCATTATGCTTGCATGTC

AAAAACTTTAAAAATCCTATAATCTTC

3' UTR-mouse alpha globulin (SEQ ID NO: 96)
GCGGCCGCTTAATTAAGCTGCCTTCTGCGGGGCTTGCCTTCTGGCCATGCCCTTCT

TCTCTCCCTTGCACCTGTACCTCTTGGTCTTTGAATAAAGCCTGAGTAGGAAGTCT

AG

3' UTR-GATA3 (full)

(SEQ ID NO: 97)
GCCCTGCTCGATGCTCACAGGGCCCCCAGCGAGAGTCCCTGCAGTCCCTTTCGAC

TTGCATTTTTGCAGGAGCAGTATCATGAAGCCTAAACGCGATGGATATATGTTTTTG

AAGGCAGAAAGCAAAATTATGTTTGCCACTTTGCAAAGGAGCTCACTGTGGTGTC

TGTGTTCCAACCACTGAATCTGGACCCCATCTGTGAATAAGCCATTCTGACTCATAT

CCCCTATTTAACAGGGTCTCTAGTGCTGTGAAAAAAAAAATGCTGAACATTGCATA

TAACTTATATTGTAAGAAATACTGTACAATGACTTTATTGCATCTGGGTAGCTGTAA

GGCATGAAGGATGCCAAGAAGTTTAAGGAATATGGGAGAAATAGTGTGGAAATTA

AGAAGAAACTAGGTCTGATATTCAAATGGACAAACTGCCAGTTTTGTTTCCTTTCA

CTGGCCACAGTTGTTTGATGCATTAAAAGAAAATAAAAAAAAGAAAAAAGAGAA

AAGAAAAAAAAGAAAAAAGTTGTAGGCGAATCATTTGTTCAAAGCTGTTGGCC

TCTGCAAAGGAAATACCAGTTCTGGGCAATCAGTGTTACCGTTCACCAGTTGCCG

TTGAGGGTTTCAGAGAGCCTTTTTCTAGGCCTACATGCTTTGTGAACAAGTCCCTG

TAATTGTTGTTTGTATGTATAATTCAAAGCACCAAAATAAGAAAAGATGTAGATTTA

TTTCATCATATTATACAGACCGAACTGTTGTATAAATTTATTTACTGCTAGTCTTAAG

AACTGCTTTCTTTCGTTTGTTTGTTTCAATATTTTCCTTCTCTCTCAATTTTTGGTTG

AATAAACTAGATTACATTCAGTTGGCCTAAGGTGGTTGTGCTCGGAGGGTTTCTTG

TTTCTTTTCCATTTTGTTTTTGGATGATATTTATTAAATAGCTTCTAAGAGTCCGGCG

GCATCTGTCTTGTCCCTATTCCTGCAGCCTGTGCTGAGGGTAGCAGTGTATGAGCT

ACCAGCGTGCATGTCAGCGACCCTGGCCCGACAGGCCACGTCCTGCAATCGGCCC

GGCTGCCTCTTCGCCCTGTCGTGTTCTGTGTTAGTGATCACTGCCTTTAATACAGTC

TGTTGGAATAATATTATAAGCATAATAATAAAGTGAAAATATTTTAAAACTACAA

3' UTR-GATA3 (first half)

(SEQ ID NO: 98)
GCCCTGCTCGATGCTCACAGGGCCCCCAGCGAGAGTCCCTGCAGTCCCTTTCGAC

TTGCATTTTTGCAGGAGCAGTATCATGAAGCCTAAACGCGATGGATATATGTTTTTG

AAGGCAGAAAGCAAAATTATGTTTGCCACTTTGCAAAGGAGCTCACTGTGGTGTC

TGTGTTCCAACCACTGAATCTGGACCCCATCTGTGAATAAGCCATTCTGACTCATAT

CCCCTATTTAACAGGGTCTCTAGTGCTGTGAAAAAAAAAATGCTGAACATTGCATA

TAACTTATATTGTAAGAAATACTGTACAATGACTTTATTGCATCTGGGTAGCTGTAA

GGCATGAAGGATGCCAAGAAGTTTAAGGAATATGGGAGAAATAGTGTGGAAATTA

AGAAGAAACTAGGTCTGATATTCAAATGGACAAACTGCCAGTTTTGTTTCCTTTCA

CTGGCCACAGTTGTTTGATGCATTAAAAGAAAATAAAAAAAAGAAAAAAGAGAA

AAGAAAAAAAAGAAAAAA

3' UTR-GATA3 (second half)

(SEQ ID NO: 99)
GTTGTAGGCGAATCATTTGTTCAAAGCTGTTGGCCTCTGCAAAGGAAATACCAGTT

CTGGGCAATCAGTGTTACCGTTCACCAGTTGCCGTTGAGGGTTTCAGAGAGCCTT

```
                                    -continued
TTTCTAGGCCTACATGCTTTGTGAACAAGTCCCTGTAATTGTTGTTTGTATGTATAAT

TCAAAGCACCAAAATAAGAAAAGATGTAGATTTATTTCATCATATTATACAGACCG

AACTGTTGTATAAATTTATTTACTGCTAGTCTTAAGAACTGCTTTCTTTCGTTTGTTT

GTTTCAATATTTTCCTTCTCTCTCAATTTTTGGTTGAATAAACTAGATTACATTCAGT

TGGCCTAAGGTGGTTGTGCTCGGAGGGTTTCTTGTTTCTTTTCCATTTTGTTTTTGG

ATGATATTTATTAAATAGCTTCTAAGAGTCCGGCGGCATCTGTCTTGTCCCTATTCCT

GCAGCCTGTGCTGAGGGTAGCAGTGTATGAGCTACCAGCGTGCATGTCAGCGACC

CTGGCCCGACAGGCCACGTCCTGCAATCGGCCCGGCTGCCTCTTCGCCCTGTCGT

GTTCTGTGTTAGTGATCACTGCCTTTAATACAGTCTGTTGGAATAATATTATAAGCAT

AATAATAAAGTGAAAATATTTTAAAACTACAA
```

In some embodiments, the disclosure provides nucleic acid sequences, each of which encodes one or more of the CARs provided herein. Exemplary nucleic sequences that encode such CARs are provided in SEQ ID NOs: 29-47. However, it should be appreciated that variants of the sequences provided herein are also contemplated. In some embodiments, the CAR is encoded by a nucleic acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the nucleic acid sequences set forth in any one of SEQ ID NOs: 29-47. In some embodiments, the CAR is encoded by a nucleic acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, or more mutations (e.g., at least 50, 100, 200, 300, 400, 500, or 600) compared to any one of the nucleic acid sequences set forth in SEQ ID NOs: 29-47. In some embodiments, the nucleic acid sequence encoding the CAR comprises a nucleic acid sequence that has at least 5, at least 10, at least 15, at least 20, at least 25, at least 30, at least 35, at least 40, at least 45, at least 50, at least 60, at least 70, at least 80, at least 90, at least 100, at least 110, at least 120, at least 130, at least 140, at least 150, at least 160, at least 170, at least 200, at least 300, at least 400, at least 500, at least 600, at least 700, at least 800, at least 900, at least 1000, at least 1100, at least 1200, at least 1300, at least 1400, at least 1500, at least 1600, or at least 1700 identical contiguous nucleotides as compared to any one of the nucleic acid sequences set forth in SEQ ID NOs: 29-47.

In some embodiments, the disclosure provides nucleic acid sequences, each of which encodes one or more of the open reading frames (ORFs) provided herein. Exemplary nucleic sequences that encode such ORFs are provided in SEQ ID NOs: 112-116, 122, and 123. However, it should be appreciated that variants of the ORF sequences provided herein are also contemplated. In some embodiments, the ORF is encoded by a nucleic acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to any one of the nucleic acid sequences set forth in any one of SEQ ID NOs: 112-116, 122, and 123. In some embodiments, the ORF is encoded by a nucleic acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, or more mutations (e.g., at least 50, 100, 200, 300, 400, 500, or 600) compared to any one of the nucleic acid sequences set forth in SEQ ID NOs: 112-116, 122, and 123. In some embodiments, the nucleic acid sequence encoding the ORF comprises a nucleic acid sequence that has at least 5, at least 10, at least 15, at least 20, at least 25, at least 30, at least 35, at least 40, at least 45, at least 50, at least 60, at least 70, at least 80, at least 90, at least 100, at least 110, at least 120, at least 130, at least 140, at least 150, at least 160, at least 170, at least 200, at least 300, at least 400, at least 500, at least 600, at least 700, at least 800, at least 900, at least 1000, at least 1100, at least 1200, at least 1300, at least 1400, at least 1500, at least 1600, or at least 1700 identical contiguous nucleotides as compared to any one of the nucleic acid sequences set forth in SEQ ID NOs: 112-116, 122, and 123.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' polyA tail which determine ribosome binding, initiation of translation and stability mRNA in the cell.

A conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T, or after PCR by any other method, including, but not limited to, enzymatic addition, DNA ligation, or in vitro recombination. PolyA tails also provide stability to RNAs and reduce their degradation. Generally, the length of a polyA tail positively correlates with the stability of the transcribed RNA. In one embodiment, the polyA tail is between 100 and 5000 adenosines. In some embodiments, the polyA tail is at least 150 (e.g., at least 150, 180, or 200 adenosines) adenosines. In some embodiments, the polyA tail is from 100 to 200, 100 to 300, 100 to 400, 100 to 500, 100 to 600, 100 to 700, 100 to 800, 100 to 900, 100 to 1000, 200 to 300, 200 to 400, 200 to 500, 200 to 600, 200 to 700, 200 to 800, 200 to 900, 200 to 1000, 300 to 400, 300 to 500, 300 to 600, 300 to 700, 300 to 800, 300 to 900, 300 to 1000, 400 to 500, 400 to 600, 400 to 700, 400 to 800, 400 to 900 400 to 1000, 500 to 600 500 to 700, 500 to 800, 500 to 900, 500 to 1000, 600 to 700, 600 to 800, 600 to 900, 600 to 1000, 700 to 800, 700 to 900, 700 to 1000, 800 to 900, 800 to 1000, or 900 to 1000 adenosines PolyA tails of RNAs can be further extended following in vitro transcription with the use of a polyA polymerase, such as E. coli polyA polymerase (E-PAP). Additionally, the attachment of different chemical groups to the 3' end can increase mRNA stability. Such attachment can contain modified/artificial nucleotides, aptamers and other compounds. For example, ATP analogs can be incorporated into the polyA tail using polyA polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs provided herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

The nucleic acid sequences coding for the desired molecules (e.g., CARs) can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned. Exemplary vectors include, without limitation cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate any of the nucleic acids provided herein.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lenti viral vectors have the added advantage over vectors derived from onco-retroviruses such as murine leukemia viruses in that they can transduce non-proliferating cells, such as hepatocytes. They also have the added advantage of low immunogenicity. In another embodiment, the desired CAR can be expressed in the cells by way of transposons. In another embodiment, the desired CAR can be express in the cells by way of homology-directed recombination.

The vectors can be suitable for replication and integration into eukaryotes. Typical cloning vectors contain transcription and translation terminators, initiation sequences, and promoters useful for regulation of the expression of the desired nucleic acid sequence. The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector. The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, retrovirus vectors are used. A number of retrovirus vectors are known in the art. In some embodiments, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence with which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In some embodiments, the promoter is an EF-1a promoter.

In order to assess the expression of a CAR polypeptide or portions thereof, the expression vector(s) to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic resistance genes, such as neo and the like. Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity, antibiotic resistance or fluorescence. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector(s), the vector(s) can be readily introduced into a host cell, e.g., mammalian, bacterial, yeast, or insect cell by any method in the art. For example, the expression vector(s) can be transferred into a host cell by physical, chemical, or biological means. In some embodiments, the host cell is a T cell. Physical methods for introducing a polynucleotide into a host cell include electroporation, mechanical membrane disruption (e.g., cell squeezing or nanoparticle-based delivery), calcium phosphate precipitation, lipofection, particle bombardment, microinjection, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is electroporation.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In some embodiments, the modified T cells of the invention are modified through the introduction of RNA (e.g., an mRNA comprises a sequence encoding a CAR as described herein). In some embodiments, an in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention.

RNA can be introduced into target cells using any of a number of different methods, for instance, commercially available methods which include, but are not limited to, electroporation (Amaxa® Nucleofector-II® (Amaxa Biosystems, Cologne, Germany)), (ECM 830 (BTX) (Harvard Instruments, Boston, Mass.) or the Gene Pulser II® (Bio-Rad, Denver, Colo.), Multiporator® (Eppendort, Hamburg Germany), mechanical membrane disruption (e.g., cell squeezing, see U.S. Pat. Pub. No. 2014/287509A1), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-400, 50-2000 bases, 150-400 bases, or 150-2000 bases in length. RNA so produced can efficiently transfect different kinds of cells. In one aspect, the template includes sequences for the CAR.

In one aspect the anti-BCMA CAR is encoded by a messenger RNA (mRNA). In one aspect the mRNA encoding the anti-BCMA CAR is introduced into an immune effector cell, e.g., a T cell or a NK cell, for production of a CAR-expressing cell (e.g., CAR T cell or CAR-expressing NK cell).

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3zeta and/or the signaling domain of CD28, 41BB and/or OX40.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs), e.g., any of the untranslated regions provided herein. The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any high-fidelity DNA polymerase useful for PCR can be used in the methods disclosed herein. The reagents and polymerase are commercially available from a number of sources.

Genetically Modified Immune Cells

In some embodiments, the CAR sequence(s) (e.g., nucleic acid sequence(s) encoding a CAR as described herein) are delivered into cells (e.g., T cells, stem cells, or NK cells) using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In another embodiment, the desired CAR can be expressed in the cells (e.g., T cells or NK cells) by way of transposons.

The disclosed methods can be applied to the modulation of immune cell (e.g., T cell or NK cell) activity in basic research and therapy, in the fields of cancer, stem cells, acute and chronic infections, and autoimmune diseases, including the assessment of the ability of the genetically modified T cell or NK cell to kill a target cell, e.g., a target cancer cell. vector, making it possible to individually regulate the expression level. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

Cloning of cells is not necessary because of the efficiency of transduction of the CAR with lentiviral vectors or oncoretroviral vectors, which can stably and uniformly modify the entire lymphocyte population.

Sources of Immune Cells

Prior to expansion and genetic modification of the immune cells (e.g., T cells) of the invention, a source of immune cells (e.g., T cells) is obtained from a subject. Immune cells (e.g., T cells) can be obtained from a number of sources, including peripheral blood mononuclear cells, bone marrow, lymph node tissue, cord blood, thymus tissue, tissue from a site of infection, ascites, pleural effusion, spleen tissue, and tumors. The immune cells (e.g., T cells) may also be generated from induced pluripotent stem cells or hematopoietic stem cells or progenitor cells. In some embodiments of the present invention, any number of immune cell lines, including but not limited to T cell and NK cell lines, available in the art, may be used. In some embodiments of the present invention, immune cells (e.g., T cells) can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, NK cells, other nucleated white blood cells, red blood cells, and platelets. In some embodiments, the cells collected by apheresis may be washed to remove the plasma fraction and to place the cells in an appropriate buffer or media for subsequent processing steps. In some embodiments of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe® 2991 cell processor, the Baxter® CytoMate®, or the Haemonetics® Cell Saver 5®) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, immune cells (e.g., T cells) are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+T$ cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values therebetween. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4$^+$, CD25$^+$, CD62L$^{hi}$, GITR$^+$, and FoxP3$^+$.

Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in some embodiments, a concentration of 2 billion cells/ml is used. In some embodiments, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4$^+$ T cells express higher levels of CD28 and are more efficiently captured than CD8$^+$ T cells in dilute concentrations. In some embodiments, the concentration of cells used is 5×10$^6$/ml. In other embodiments, the concentration used can be from about 1×10$^5$/ml to 1×10$^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 10 per minute and stored in the vapor phase of a liquid nitrogen storage tank. Other methods of controlled freezing may be used as well as uncontrolled freezing immediately at −20° C. or in liquid nitrogen. In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In some embodiments a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH®, anti-CD3 antibodies, Cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH®. In another embodiment, the cells are isolated prior to and can be frozen for later use for treatment following B-cell ablative therapy such as agents that react with CD20, e.g., RITUXAN®.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

In certain embodiments, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In some embodiments, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In some embodiments, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In some embodiments, a ratio of particles to cells of 1:1 or less is used. In one particular embodiment, a preferred particle: cell ratio is 1:5. In further embodiments, the ratio of particles to cells can be varied depending on the day of stimulation. For example, in some embodiments, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In some embodiments the cells (for example, 104 to 109 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in some embodiments, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments of the present invention, the mixture may be cultured for several hours (about 3 hours) to about 14 days or any hourly integer value in between. In another embodiment, the mixture may be cultured for 21 days. In some embodiments of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGF-β, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (¾, CD4+) that is greater than the cytotoxic or suppressor T cell population (Tc, CD8+). Ex vivo expansion of T cells by stimulating CD3 and CD28 receptors produces a population of T cells that prior to about days 8-9 consists predominately of ¾ cells, while after about days 8-9, the population of T cells comprises an increasingly greater population of Tc cells. Accordingly, depending on the purpose of treatment, infusing a subject with a T cell population comprising predominately of TH cells may be advantageous. Similarly, if an antigen-specific subset of Tc cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In some embodiments, the present invention encompasses a cell (e.g., T cell) modified to express a CAR that combines an antigen recognition domains (e.g., an scFv specific for BCMA), a transmembrane domain (e.g., a CD8 transmembrane domain) and a cytoplasmic domain (e.g., an intracellular domain of CD3-zeta, CD28, OX40, 4-1BB, or any combinations thereof). Therefore, in some instances, the transduced immune cell (e.g., T cell) can elicit a CAR-mediated immune (e.g., T-cell) response. In some embodiments, the invention provides the use of a CAR to redirect the specificity of a primary T cell to a tumor antigen. Thus, in some embodiments, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target (e.g., BCMA), a zeta chain portion comprising for example the intracellular domain of human CD3zeta, and a costimulatory signaling region. In some embodiments, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR. For example, BCMA-specific CAR T cells elicit an immune response specific against cells expressing BCMA. While the data disclosed herein specifically disclose lentiviral vectors comprising anti-BCMA scFv, a CD8 transmembrane domain, and 41BB, CD28 and CD3zeta signaling domains, the invention should be construed to include any number of variations for each of the components of the construct as described elsewhere herein. That is, the invention includes the use of any antigen binding moiety in the CAR to generate a CAR-mediated T-cell response specific to the antigen binding moiety. For example, the antigen binding moiety in the CAR of the invention can target a tumor antigen for the purposes of treating cancer. In some embodiments, the antigen binding moiety portion of the CAR of the invention is designed to treat a particular cancer, such as multiple myeloma.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells. Ex vivo procedures are well known in the art and are discussed more fully below. Briefly, cells are isolated from a mammal (preferably a human) and genetically modified (e.g., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

A procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells. In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised, such as individuals having cancer. In particular, the CAR-modified T cells of the invention are used in the treatment of multiple myeloma. In certain embodiments, the cells of the invention are used in the treatment of patients at risk for developing multiple myeloma.

The CAR-modified immune cells (e.g., CAR T cells) of the present invention, or a composition comprising such cells, may be used, or may be administered to a subject in need thereof, to provide anti-tumor immunity; to treat or prevent cancer; to treat or prevent autoimmune condition; or to treat or prevent an allergic condition. In some embodiments, the cancer is multiple myeloma, Hodgkin lymphoma, non-Hodgkin lymphoma, a leukemia, or glioblastoma. In some embodiments, the autoimmune condition is myasthenia gravis, systemic lupus erythematosus, rheumatoid arthritis, pemphigus, psoriasis, inflammatory bowel disease, celiac sprue, pernicious anemia, idiopathic thrombocytopenia purpura, scleroderma, Graves' disease, Sjögren syndrome, Goodpasture syndrome, or type 1 diabetes. In some embodiments, the allergic condition is anaphylaxis, asthma, food allergy, stinging insect allergy, drug allergy, allergic rhinitis, urticaria, angioedema, eczema, atopic dermatitis, contact dermatitis, and eosinophilic esophagitis.

The CAR-modified immune cells (e.g., CAR T cells) of the present invention may be administered either alone, or as a composition (e.g., a pharmaceutical composition) in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the CAR-modified immune cells (e.g., CAR T cells) described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319: 1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated immune (e.g., T cells) to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In some embodiments, the immune cell (e.g., T cell) compositions of the present invention are administered to a patient by intradermal or subcutaneous injection. In another embodiment, the immune cell (e.g., T cell) compositions of the present invention are preferably administered by i.v. injection. The compositions of immune cells (e.g., T cells) may be injected directly into a tumor, lymph node, or site of disease.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH (alemtuzumab), anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766). Strategies for CAR T cell dosing and scheduling have been discussed (Ertl et al., 2011, Cancer Res, 71:3175-81; Junghans, 2010, Journal of Translational Medicine, 8:55).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described herein may be more fully understood, the following examples are set forth. The synthetic examples described in this application are offered to illustrate the compounds and methods provided herein and are not to be construed in any way as limiting their scope.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

Example 1: Production of Functional CAR T Cells from an Inventive mRNA Construct Human CAR T cells were produced by use of an inventive mRNA construct that encoded an inventive CAR protein. The CAR T cells were observed to be viable, to bind BCMA, and to kill BCMA+ tumor cells.

An inventive mRNA construct comprising the nucleotide sequence of SEQ ID: 31 was generated by in vitro transcription from a DNA plasmid. In vitro transcription was performed by T7 RNA polymerase from a linearized plasmid template and a polyadenine tail of about 150 adenine nucleotides was added enzymatically. A 7-methylguanosine cap was incorporated at the 5' end of the mRNA during the co-transcriptional mRNA synthesis.

The inventive mRNA construct comprised, from 5' to 3': a 5' cap, a 5' UTR described as SEQ ID: 74, an open reading frame (ORF) described as SEQ ID: 112, a 3' UTR described as SEQ ID: 92, and a 3' polyadenine tail of 150 adenine units or more. The ORF encoded an inventive CAR protein with the amino acid sequences of SEQ ID: 21.

To prepare CAR T cells from mRNA constructs, lymphocytes were obtained by apheresis from a healthy human donor. From these lymphocytes, CD8+ T cells were positively selected with paramagnetic microbeads conjugated to an anti-CD8 antibody. This yielded cells that were 95% CD8+ T cells and 95% viable. These enriched CD8+ T cells were expanded by incubation at 37° C. with 5% $CO_2$ in the presence of anti-CD3 antibody (clone OKT3) for about 14 days. The cells were resuspended in P3 transfection buffer (Lonza) and transfected with the mRNA construct by electroporation (4D Nucleofector®, Lonza) according to manufacturer's instructions. Cells were then returned to culture in a standard medium containing IL-15 for about 8 hours.

CAR T cells obtained from the above-described process were tested for viability, CAR protein expression, BCMA binding, and cytotoxicity, i.e., the ability to kill BCMA+ myeloma (tumor) cells. Viability, CAR expression, and BCMA binding were determined by flow cytometry on a GUAVA® EASYCYTE® 12HT Flow cytometer (EMD Millipore). To test viability, a sample of the CAR T cells was mixed with propidium iodide and run on the flow cytometer with electronic gating on fluorescence in the near infrared channel. To test CAR protein expression and BCMA binding, a sample of the CAR T cells was incubated with 0.4 ug/mL of phycoerythrin (PE)-conjugated BCMA (Recombinant Human TNFRSF17 protein, Fc/His-tagged, R-PE labeled; Creative Biomart, Shirley, NY). CAR expression was assessed on the flow cytometer with electronic gating on fluorescence in the yellow channel to detect presence or absence of emission from BCMA-PE on CAR-positive and CAR-negative cells. BCMA binding was determined by measuring the intensity of fluorescence in the yellow channel to determine the relative quantity of BCMA-PE bound to labelled CAR-positive cells. For the viability, expression, and BCMA binding assays, CD8+ T cells electroporated without mRNA (CAR-negative T Cells) were tested as a parallel control.

To test the capacity of the CAR T cells to kill BCMA+ myeloma cells, the CAR T cells were co-incubated with BCMA+ myeloma cell line expressing green fluorescent protein (MM.1S-GFP). Aliquots of 50,000 MM.1S-GFP tumor cells were placed in wells of a 96-well plate. Between about 2500 and 50,000 CAR T cells were added to each well to obtain various effector:target ratios (i.e., ratios of CAR T cells to BCMA+ myeloma cells) that were between about 1:1 and 1:20. Following overnight incubation, propidium iodide was used to stain dead cells. Viable target cells were identified, and cell density was determined by flow cytometry. The degree of myeloma cell killing by the CAR T cells was calculated by comparison to the number of myeloma cells in wells concurrent control wells that did not contain CAR T cells. The results are reflected in FIG. 1 and Table 2, which show an assessment of cell viability, CAR expression, BCMA binding by CAR T cells generated with the CAR of SEQ ID: 31 or a control (no mRNA) at 24 hours post transfection, as well as the percentage of killing of BCMA+ myeloma (tumor) cells.

TABLE 2

Assessment of cell viability, CAR expression, BCMA binding by CAR T cells generated with the CAR of SEQ ID: 31, and the percentage of killing of BCMA+ myeloma (tumor) cells.

|  | Viability * | CAR+ Cells (%) * | BCMA binding (MFI) * | % Killing ** |
|---|---|---|---|---|
| CAR T cells | 83.9 | 86.6 | 1333 | 94.4 |
| Control CD8+ | 90.9 | 1.8 | 20 | 0 |

TABLE 2-continued

Assessment of cell viability, CAR expression, BCMA binding by CAR T cells generated with the CAR of SEQ ID: 31, and the percentage of killing of BCMA+ myeloma (tumor) cells.

|  | Viability * | CAR+ Cells (%) * | BCMA binding (MFI) * | % Killing ** |
|---|---|---|---|---|
| T cells (electroporated without mRNA) | | | | |

* Measured at 4 hours post-transfection.
** 1:10 Effector to Target Ratio Used in Killing Assay (killing assay was incubated for 4 days).

In conclusion, an mRNA construct was used to produce CAR T cells. The mRNA construct encoded an inventive CAR protein. The CAR T cells demonstrated high viability, CAR protein expression, BCMA binding, and killing of BCMA+ myeloma (tumor) cells. CD8+ T cells electroporated without the mRNA construct showed essentially no CAR expression, essentially no BCMA binding, and no killing of tumor cells.

Example 2: Amino Acid Substitutions in CAR Complementarity-Determining Regions

Various amino acid substitutions were introduced into the complementarity-determining regions (CDRs) of anti-BCMA CARs in order to generate CARs with improved properties. Fortuitously, these modifications substantially improved BCMA binding and tumor killing by CAR T cells compared to the CAR T cells and the respective CAR used in the clinical trial of Ali et al. (2016), i.e., of SEQ ID: 19.

Numerous CAR-encoding mRNA constructs were prepared using SEQ ID: 29 as a reference sequence. The new constructs varied with respect to one or more amino acid residues in one or more CDRs.

Below, Table 3 provides mRNA constructs described in this example. Table 3 indicates the respective parent sequence and sequence fragments included in each of the three heavy-chain and three light-chain CDRs: CDRH1, CDRH2, CDRH3, CDRL1, CDRL2, and CDRL3. Portions of the CARs that correspond or substantially correspond to the scFv regions of the CARs are referred to as "New scFv Sequences" in Table 3.

TABLE 3

Listing of sequence identification numbers (SEQ ID NOs) for "new scFv" sequences, including their parent sequence and corresponding CDR sequences.

| New scFv Sequence | Parent sequence of scFv framework | HEAVY | | | LIGHT | | |
|---|---|---|---|---|---|---|---|
| | | CDRH 1 | CDRH 2 | CDRH 3 | CDRL 1 | CDRL 2 | CDRL 3 |
| 48 | 48 | 1 | 4 | 7 | 10 | 12 | 16 |
| 57 | 57 | 1 | 4 | 7 | 10 | 12 | 16 |
| 60 | 60 | 1 | 4 | 7 | 10 | 12 | 16 |
| 62 | 57 | 3* | 4 | 7 | 10 | 12 | 16 |
| 63 | 57 | 1 | 4 | 8* | 10 | 12 | 16 |
| 64 | 57 | 1 | 4 | 7 | 11* | 14* | 17* |
| 65 | 57 | 1 | 4 | 7 | 11* | 14* | 18* |
| 66 | 57 | 2* | 6* | 9* | 10 | 12 | 16 |
| 67 | 57 | 3* | 5* | 8* | 10 | 12 | 16 |
| 68 | 57 | 3* | 4 | 9* | 10 | 12 | 18* |
| 69 | 57 | 2* | 6* | 9* | 11* | 13* | 17* |
| 70 | 57 | 1 | 4 | 7 | 10 | 15* | 16 |

An asterisk (*) indicates an amino acid substitution with respect to the parent sequence and is not part of the sequence ID.

For each of the mRNA constructs, CAR T cells were prepared by transfection into human CD8+ cells, as described in Example 1. The CAR T cells made from each mRNA construct were then tested 3 days after electroporation for BCMA binding and tumor killing, as described in Example 1. Results are summarized in Table 4, shown below.

TABLE 4

BCMA binding results and % of human myeloma cells killed using CAR T cells expressing the corresponding scFv portions.

| New scFv Sequence | BCMA Binding (arbitrary units) | Killing* (% killed) |
|---|---|---|
| SEQ ID: 48 | 100 (standard of reference) | 46% |
| SEQ ID: 57 | 343 | 85% |
| SEQ ID: 60 | 381 | 83% |
| SEQ ID: 62 | 189 | 3% |
| SEQ ID: 63 | 439 | 78% |
| SEQ ID: 64 | 496 | 26% |
| SEQ ID: 65 | 173 | 86% |
| SEQ ID: 66 | 269 | 81% |
| SEQ ID: 67 | 310 | 0% |
| SEQ ID: 68 | 446 | 7% |
| SEQ ID: 69 | 230 | 77% |
| SEQ ID: 70 | 404 | 83% |

*Effector:target ratio of 1:2.

Thus, several attempts to modify the CDRs were unsuccessful, as they reduced BCMA binding. However, certain CARs, e.g. those comprising sequences of SEQ ID: 57, SEQ ID: 60, SEQ ID: 65, SEQ ID: 66, SEQ ID: 69, and SEQ ID: 70, were not only substantially modified in their CDR residues compared to the initial CAR of SEQ ID: 19, but also provided dramatically better CAR expression and killing of human myeloma cells.

Example 3. Humanization by Amino Acid Substitutions in CAR scFv Framework Regions Various amino acid substitutions were introduced in the scFv framework regions of a CAR in order to humanize the CAR. Fortuitously, these modifications substantially improved CAR T cell BCMA binding and tumor killing compared to the CAR T cells of the non-humanized CAR used in the clinical trial of Ali et al (2016), i.e., of SEQ ID: 19.

Numerous CAR-encoding mRNA constructs were prepared using the mRNA construct of SEQ ID: 29 as a starting point (which encodes a CAR of sequence SEQ ID: 19 and comprises the scFv of sequence SEQ ID: 48). These constructs encoded the same or substantially the same amino acid residues in the scFv complementary-determining regions (CDRs) but varied with respect to the amino acid residues in the scFv framework regions. In making these variations, the experimenter's intent was to humanize the scFv framework regions without reducing BCMA-binding and tumor-killing properties of CAR T cells that express the CAR. For each of the mRNA constructs, CAR T cells were prepared by transfection into human CD8+ cells, substantially as described in Example 1. The CAR T cells made from each mRNA construct were then tested 3 days after electroporation for BCMA binding and/or tumor killing, as substantially described in Example 1.

In a first iteration of experiments, various modifications were made to scFv framework residues of the CAR, with results shown in Table 5:

TABLE 5

BCMA binding results using CAR T cells expressing the corresponding scFv sequences having modifications to framework residues.

| scFv Sequence | BCMA Binding (relative to SEQ ID: 48) |
|---|---|
| SEQ ID: 48 | 100 (standard of reference) |
| SEQ ID: 54 | 141 |
| SEQ ID: 49 | 76 |
| SEQ ID: 50 | 51 |
| SEQ ID: 51 | 54 |
| SEQ ID: 52 | 82 |
| SEQ ID: 53 | 103 |
| SEQ ID: 55 | 12 |

Thus, several attempts to humanize the scFv framework were unsuccessful, as they reduced BCMA binding. However, a CAR comprising the scFv of SEQ ID: 54 provided a 41% improvement in CAR T cell BCMA binding over an otherwise comparable CAR comprising the reference scFv of SEQ ID: 48. Therefore, the scFv of SEQ ID: 54 was selected as a lead for further optimization. In a second iteration of experiments, further and various modifications were made to the scFv framework residues of the CAR, with the following results for BCMA binding, shown in Table 6:

TABLE 6

BCMA binding results using CAR T cells expressing the corresponding scFv sequences having further modifications to framework residues.

| scFv Sequence | BCMA Binding (relative to SEQ ID: 54) |
|---|---|
| SEQ ID: 54 | 100 (standard of reference) |
| SEQ ID: 56 | 58 |
| SEQ ID: 57 | 124 |
| SEQ ID: 58 | 40 |
| SEQ ID: 59 | 79 |

Several attempts to humanize the scFv framework were unsuccessful, as they reduced BCMA binding. However, the scFv of SEQ ID: 57 provided a further 24% improvement in CAR T cell BCMA binding over the scFv of SEQ ID: 54. Therefore, the CAR comprising the scFv of SEQ ID: 57 was selected as a lead for further optimization.

In a third iteration of experiments, the CAR comprising scFv of SEQ ID: 57 was compared: (1) to CARs comprising the initial scFv of SEQ ID: 48; (2) to an scFv of SEQ ID: 60, which was further modified from that of SEQ ID: 57; and (3) to an scFv of SEQ ID: 61, which was developed by an independent method from the scFv of SEQ ID: 48 (Antibody Humanization by a Single Cycle of CDR-Grafting, Hu et al. in Ricin Toxin; Bentham Science Publishers Eds. J W Cherwonwogrodzky). The following results, shown in table 7, were seen for BCMA binding and tumor killing:

TABLE 7

BCMA binding results and % of human myeloma cells killed using CAR T cells expressing the corresponding scFv portions.

| scFv Sequence | BCMA Binding* | Killing** (% killed) |
|---|---|---|
| SEQ ID: 48 | 100 (standard of reference) | 46% |
| SEQ ID: 57 | 460 | 85% |
| SEQ ID: 60 | 382 | 83% |
| SEQ ID: 61 | 34 | Not tested. |

**Effector:target ratio of 1:10.

Lastly, to measure the amount of humanization achieved, the amino acids in the framework regions of the scFv of each of the above sequences were compared to those of that sequence's closest germline neighbor as identified from sequences in the Immunogenetics Database (IMGT) (IMGT®, the international ImMunoGeneTics information system® 25 years on. Lefranc M-P et al., Nucleic Acids Res. 2015 January; 43:D413-22. The mean amino acid identity to the closest germline neighbor was 78% for SEQ ID: 48, 84% for SEQ ID: 57, and 88% for SEQ ID: 60. Thus, at the conclusion of this series of sequence modifications and assays, the CARs containing scFv of SEQ ID: 57 and SEQ ID: 60 were not only substantially humanized in their scFv framework residues compared to the initial CAR of SEQ ID: 19, but also provided CAR T cells with dramatically better BCMA binding and tumor killing.

Example 4. CARs Combining Humanized Framework and CDR Regions

Experiments were carried out to test various combinations of the humanized scFv framework and CDR sequences described in Examples 2 and 3. The purpose was to determine which of various combinations would provide CAR T cells with superior BCMA binding and tumor killing. Provided below is a reference table for the sequences of this example. For each combination shown in the table, CAR T cells were prepared and tested substantially as described in Example 1. For comparison, CAR T cells were also prepared with a CAR protein corresponding to that of Ali et al (2016), i.e., of SEQ ID: 19.

Table 8 indicates the respective parent sequence and sequence fragments included in each of the three heavy-chain and three light-chain CDRs: CDRH1, CDRH2, CDRH3, CDRL1, CDRL2, and CDRL3.

TABLE 8

Listing of sequence identification numbers (SEQ ID NOs) for "Full Length Car" sequences, including their parent sequence of scFv framework and corresponding CDR sequences.

| Full Length CAR Sequence | Parent sequence of scFv framework | HEAVY | | | LIGHT | | |
|---|---|---|---|---|---|---|---|
| | | CDRH1 | CDRH2 | CDRH3 | CDRL1 | CDRL2 | CDRL3 |
| 19 | 48 | 1 | 4 | 7 | 10 | 12 | 16 |
| 28 | 60 | 1 | 4 | 7 | 10 | 12 | 16 |
| 20 | 60 | 2* | 6* | 9* | 11* | 14* | 17* |
| 21 | 60 | 2* | 6* | 9* | 11* | 14* | 17* |
| 22 | 60 | 2* | 6* | 9* | 11* | 14* | 18* |
| 23 | 60 | 2* | 6* | 9* | 11* | 14* | 18* |
| 24 | 60 | 1 | 4 | 8* | 10 | 15* | 17* |
| 25 | 60 | 1 | 4 | 8* | 10 | 15* | 17* |

An asterisk (*) indicates an amino acid substitution with respect to the parent sequence and is not part of the sequence ID. CAR Sequences SEQ ID NOs: 21, 23, and 25 are versions of SEQ ID NOs: 20, 22, and 24, respectively, that further comprise a 41BB intracellular costimulatory domain.

CAR T cells made from each mRNA construct were tested about 3 days after electroporation for BCMA binding and tumor killing. The results of which are indicated in Table 9:

TABLE 9

BCMA binding results and % of human myeloma cells killed using CAR T cells expressing the corresponding CAR portions.

| CAR Sequence | BCMA Binding* | Killing** (% killed) |
|---|---|---|
| SEQ ID: 19 | 100 (standard of reference) | 46% (prior experiment) |
| SEQ ID: 28 | 377 | 83% |
| SEQ ID: 20 | 189 | 84% |
| SEQ ID: 21 | 439 | 69% |
| SEQ ID: 22 | 496 | 73% |
| SEQ ID: 23 | 173 | 67% |
| SEQ ID: 24 | 269 | 74% |
| SEQ ID: 25 | 310 | 60% |

Thus, the humanized constructs of SEQ ID: 28, SEQ ID: 20, SEQ ID: 21, SEQ ID: 22, SEQ ID: 23, SEQ ID: 24, and SEQ ID: 25 provided CAR T cells with superior BCMA binding and killing of human myeloma cells, as compared to SEQ ID: 19.

The degree of humanization of the combined framework and CDR regions in the scFv of these constructs was measured using the method of Lazar (A molecular immunology approach to antibody humanization and functional optimization, Lazar GA. et al. Molecular Immunology (2007) 44:1986) to determine Human String Content and Perfect 9mer scores. The results are summarized in Table 10:

TABLE 10

Degree of humanization for each indicated CAR amino acid sequence, including the human string content and perfect 9mer score.

| Sequence | Human String Content | Perfect 9mer Score |
|---|---|---|
| SEQ ID: 19 | 72% | 13 |
| SEQ ID: 28 | 81% | 69 |
| SEQ ID: 20 | 86% | 92 |
| SEQ ID: 21 | 86% | 92 |
| SEQ ID: 22 | 87% | 96 |
| SEQ ID: 23 | 87% | 96 |
| SEQ ID: 24 | 81% | 69 |
| SEQ ID: 25 | 81% | 69 |

The Human String Content and Perfect 9mer Scores showed that successful humanization of the parent sequence had been achieved. In conclusion, after an extensive series of iterative, empirical residue modifications to the scFv regions of a CAR, several CARs were obtained that were not only humanized in their scFv regions with respect to the CAR of SEQ ID: 19, but also provided CAR T cells with dramatically better BCMA binding and killing of myeloma cells.

Example 5: Amino Acid Substitutions in CAR Costimulatory Domains

A controlled experiment was conducted to test whether inclusion or modification of certain intracellular costimulatory domains in the CAR protein improved expression of the CAR protein and improved BCMA binding and tumor killing by the corresponding CAR T cells.

Multiple mRNA constructs were prepared, wherein the CAR proteins they encoded comprised the same signal peptide, scFv, stalk, and transmembrane domains but differed by one or more amino acids in their costimulatory domains. For each of the mRNA constructs, CAR T cells were prepared by transfection into human CD8+ cells, substantially as described in Example 1. The CAR T cells made from each mRNA construct were then tested around 24 hours after electroporation for CAR expression and antitumor cytotoxicity, substantially as described in Example 1. The mRNA construct used in the clinical trial of Ali et al (2016) was tested as a control (SEQ ID: 29). The mRNA constructs and their expression results are shown below, in Table 11. For each costimulatory domain, the SEQ ID number and natural source of the sequence are shown.

TABLE 11

Relative expression and % of human myeloma cells killed using CAR T cells expressing the corresponding CAR costimulatory domains.

| Sequence | Gene Source for Costimulatory Domain | Relative expression | Killing* (% killed) |
|---|---|---|---|
| SEQ ID: 29 | CD28-CD3z | 100 (standard of reference) | 50% |
| SEQ ID: 103 | CD28-CD3z | 136 | 52% |
| SEQ ID: 107 | CD3z | 206 | 64% |
| SEQ ID: 104 | 41BB-CD3z | 197 | 58% |
| SEQ ID: 105 | OX40-CD3z | 214 | 46% |
| SEQ ID: 106 | 41BB-OX40-CD3z | 217 | 43% |

*Effector:target ratio of 1:10.

Compared to constructs that comprised a CD28-CD3z domain, those that comprised CD3z only, 41BB-CD3z, OX40-CD3z, or 41BB-OX40-CD3z showed superior expression. This was unexpected, because the substitution of one naturally occurring costimulatory domain for another would not normally be expected to affect protein expression.

Constructs that comprised a costimulatory domain that was CD3z only or 41BB-CD3z also provided better killing of BCMA+ tumor cells. Despite their excellent expression, constructs that comprised OX40-CD3z or 41BB-OX40-CD3z showed inferior tumor killing compared to constructs that comprised a CD28-CD3z domain.

Thus, in a controlled experiment that tested variations in costimulatory regions, the constructs of SEQ ID: 107 and SEQ ID: 104 provided a combination of superior expression and tumor killing. Improved expression did not necessarily coincide with improved killing.

Example 6: Substitution of Untranslated Regions in a CAR-Encoding mRNA Construct An experiment was conducted to test how variation in the 5' and/or 3' untranslated regions of a CAR-encoding mRNA construct would affect CAR expression in human T cells.

Numerous mRNA constructs were prepared that encoded the same CAR protein (i.e., of SEQ ID: 59) but differed in the nucleotide sequences of their 5' and/or 3' untranslated regions (UTRs). These constructs were otherwise identical, e.g., with respect to the 5' cap and polyadenine tail. The intention was to compare several constructs that incorporated different 5' and 3' UTR sequences that naturally occurred in one or more human genes, e.g., the CD3D and CD8B2 genes.

For one construct, a 218-nucleotide portion that occurs in the ORF of the GATA3 gene (i.e., SEQ ID NO: 92), not its 3' UTR, was used as the 3'UTR and functioned particularly well.

For each of the mRNA constructs, CAR T cells were prepared substantially as described in Example 1. About 24 hours after transfection, CAR T cells made from each mRNA construct were tested for level of CAR expression substantially by the methods described in Example 1. The mRNA constructs and their expression results are shown below in Table 12. For each construct, the respective SEQ ID numbers and natural source of the sequence are shown.

TABLE 12

Relative expression of the CAR of SEQ ID NO: 59 (Y34) using the indicated combination of 5' and 3' UTR sequences. The sequence of SEQ ID NO: 92, which is the open reading frame (ORF) of GATA3, worked particularly well to improve expression.

| Construct | 5' UTR Sequence (Natural source) | CAR ORF Sequence | 3'UTR Sequence (Natural source) | Relative expression* |
|---|---|---|---|---|
| A | SEQ ID: 77 (CD3D) | SEQ ID: 59 | SEQ ID: 87 (CD3D) | 100 |
| B | SEQ ID: 75 (CD8B2) | SEQ ID: 59 | SEQ ID: 87 (CD3D) | 146 |
| C | SEQ ID: 75 (CD8B2) | SEQ ID: 59 | SEQ ID: 89 (MYH8) | 63 |
| D | SEQ ID: 74 (IgG) | SEQ ID: 59 | SEQ ID: 86 (AFP) | 103 |
| E | SEQ ID: 74 (IgG) | SEQ ID: 59 | SEQ ID: 87 (CD3D) | 165 |
| F | SEQ ID: 74 (IgG) | SEQ ID: 59 | SEQ ID: 92 (GATA3 ORF) | 264 |
| G | SEQ ID: 74 (IgG) | SEQ ID: 59 | SEQ ID: 84 (IgG) | 136 |
| H | SEQ ID: 74 (IgG) | SEQ ID: 59 | SEQ ID: 89 (MYH8) | 70 |

*Mean fluorescence intensity, normalized to Construct A = 100.
IgG = IgG heavy chain, chromosome 14.

For the 5' UTR, SEQ ID: 74 conferred best expression (compare Constructs A, B and E). For the 3' UTR, SEQ ID: 92 conferred the best expression (compare Constructs E and F).

In conclusion, an experiment tested how variation in the 5' and/or 3' untranslated regions of a CAR-encoding mRNA construct would affect CAR expression in human T cells. Among several alternatives that appeared equally reasonable a priori, Construct F showed the best expression, more than 2.6-fold better than the mean expression of the other seven constructs. The superior performance of Construct F was due to the inclusion of a 5' UTR comprising nucleotides of SEQ ID: 74 and a 3' UTR comprising nucleotides of SEQ ID: 92.

This result was surprising, in part because SEQ ID: 92 is not a naturally-occurring UTR. SEQ ID: 92, which was included in Construct F, was expected to reduce, rather than increase, CAR expression.

Example 7: Improved Polyadenine Tail for a CAR-Encoding mRNA Construct

A controlled experiment was conducted to test the addition of certain 3' polyadenine tails to a CAR-encoding mRNA construct.

Numerous mRNA constructs were prepared that comprised the same 5'UTR, open reading frame and 3'UTR encoding an anti-BCMA CAR protein but included or did not include a 3' polyadenine tail of 78 or more nucleotides. Each construct comprised exactly one mRNA sequence selected from: SEQ ID:46, SEQ ID:41, SEQ ID:42, SEQ ID:43, SEQ ID:44 or SEQ ID:45. In each construct the polyadenine tail was located 3' with respect to the 3' UTR, as such 3' UTR is described in Example 2. Additional polyadenylation was performed enzymatically on an mRNA construct that comprised the nucleotide sequence of SEQ ID: 36 to obtain an otherwise identical mRNA construct wherein the polyadenine tail comprised over 150 nucleotides. For each of the mRNA constructs, CAR T cells were prepared by transfection into human CD8+ cells, substantially as described in Example 1. About 24 hours after transfection, the CAR T cells were tested for level of CAR expression substantially as described in Example 1. Results from the two experiments are shown below in Tables 13 and 14.

TABLE 13

Relative expression of full-length CARs having a 78-mer PolyA tail as compared to CARs having no PolyA tail. Fold improvement of expression is provided for each CAR construct.

| | Relative Expression* | | |
|---|---|---|---|
| Construct | Without PolyA | 78-mer PolyA | Fold Improvement |
| SEQ ID: 46 | 100 | 578 | 5.8 |
| SEQ ID: 41 | 99 | 310 | 3.1 |
| SEQ ID: 42 | 50 | 210 | 4.2 |
| SEQ ID: 43 | 105 | 222 | 2.1 |
| SEQ ID: 44 | 106 | 335 | 3.2 |
| SEQ ID: 45 | 57 | 425 | 7.5 |
| Mean | 86 | 347 | 4.3 (p < 0.001) |

*Mean fluorescence intensity, normalized to SEQ ID: 46 without PolyA = 100.

TABLE 14

Fold improvement in expression of the CAR of SEQ ID NO 36 having a 78-mer PolyA tail or a PolyA tail that has more than 150 A residues. Fold improvement of expression is provided for the CAR construct of SEQ ID NO: 36.

| | Relative Expression* | | |
|---|---|---|---|
| Construct | 78-mer PolyA | >150-mer PolyA | Fold Improvement |
| SEQ ID: 36 | 100 | 243 | 2.4 |

*Mean fluorescence intensity, normalized to SEQ ID: 46 without PolyA = 100.
*Mean fluorescence intensity, normalized to SEQ ID: 36 with 78-mer PolyA = 100.

Thus, direct experimental comparison showed that inclusion of a 78-mer polyadenine tail in the mRNA construct improved expression of inventive CAR proteins by a factor of 4.3 (p<0.001). Compared the 78-mer, inclusion of a >150-mer polyadenine tail further improved CAR expression by a factor of 2.4.

Example 8: Synonymous Nucleotide Substitutions in a CAR-Encoding mRNA Construct

A controlled experiment was conducted to test whether certain synonymous nucleotide substitutions to the ORF of CAR-encoding mRNA construct the function of anti-BCMA CAR T cells.

Multiple mRNA constructs were prepared wherein ORFs encoded the same CAR protein of SEQ ID: 26, but wherein the nucleotide sequences of those ORFs differed, i.e., by the introduction of synonymous nucleotide substitutions. A construct comprising the ORF nucleotide sequence of SEQ ID: 116 served as the control. For each of the mRNA constructs, CAR T cells were prepared by transfection of mRNA into human CD8+ T cells, as described in Example 1. About 24 hours after transfection, the CAR T cells were tested for BCMA binding, as described in Example 1.

As compared to the construct of SEQ ID: 116, the constructs of SEQ ID: 122 (II new codon optimization) and SEQ ID: 123 (II dU) yielded CAR T cells for which BCMA binding was 1.65- and 3.43-fold higher, respectively. This was surprising, because the synonymous nucleotide substitutions did not alter the CAR protein sequences. In conclusion, certain synonymous nucleotide substitutions in the ORF of a CAR-encoding mRNA construct improved the BCMA binding properties of CAR T cells.

Example 9: Test of CAR Specificity and Cross-Reactivity

CAR T cells produced from inventive mRNA constructs comprising the nucleotide sequences of SEQ ID: 31 were tested for CAR interactions with a cell microarray library that included 5528 human plasma membrane proteins and cell-surface-tethered human secreted proteins (Retrogenix, High Peak, UK). Otherwise comparable CAR T cells, wherein the mRNA constructs were of SEQ ID: 35 or SEQ ID: 40, were tested on a smaller subset of protein for confirmatory purposes. Otherwise comparable T cells that lacked the CAR were used to test for non-CAR-specific interactions. Each of the CARs of SEQ ID: 31, SEQ ID: 35, and SEQ ID: 40 specifically interacted with human BCMA but no interaction between the CAR and any other protein was observed. In conclusion, three inventive CARs specifically bound to BCMA but did not cross-react with another antigen.

Example 10: In Vivo Assessment of CAR T Cell Antitumor Activity

CAR T cells produced from inventive mRNA constructs comprising the nucleotide sequences of SEQ ID: 30, SEQ ID: 31, and SEQ ID: 35 were tested in an animal model that measures the growth of human myeloma tumor cells in the animal. These mRNA constructs encoded CAR proteins that comprised, respectively, the sequences of SEQ ID: 20, SEQ ID: 21, and SEQ ID: 25.

Figure 2:
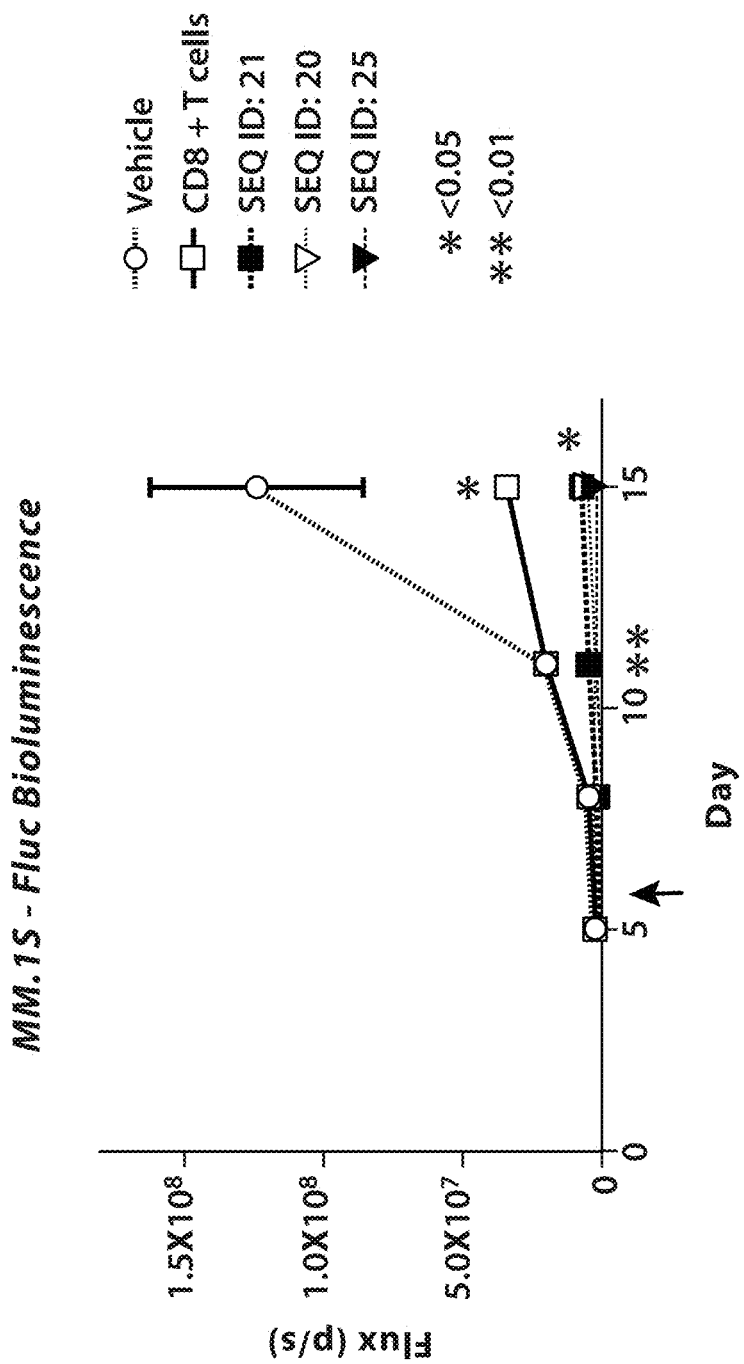
FIG. 2 shows measurements of multiple myeloma MM.1S cell tumors in vivo following treatment with humanized anti-BCMA CAR T cells generated with a CAR of SEQ ID: 20, 21 or 25. The CAR T cells or control (CAR-negative) cells were administered as a single dose on day 6. Tumor burden is indicated as mean bioluminescence intensity (Flux, photons/second) from fluorescent tumor cells.

CAR T cells were prepared by transfection of the mRNA CAR construct into human CD8+ cells, as described in Example 1. Negative controls used in this study included (1) unmodified CD8+ cells and (2) vehicle only. NOD-scid-gamma (NSG) mice were inoculated with 2 million MM. 1S-fluc human myeloma tumor cells. Tumor growth was monitored by serial bioluminescence imaging. On Day 6 mice were randomized to receive the vehicle, unmodified CD8+ T Cells, or CAR T Cells transfected to express a CAR of SEQ ID: 20, SEQ ID: 21, or SEQ ID: 25. FIG. 2 shows the results of tumor measurements. By Day 11, tumors grew extensively in mice treated with vehicle or modified CD8+ cells. In contrast, CAR T Cells transfected to express a CAR of SEQ ID: 20 (p=0.006), SEQ ID: 21 (p=0.01), or SEQ ID: 25 (p=0.004) significantly inhibited tumor growth. In conclusion, CAR T Cells prepared from three examples of the inventive, anti-BCMA CAR-encoding mRNA constructs significantly inhibited growth of human myeloma tumors in an animal model.

Example 11: Effect of mRNA on CAR T Cell Survival

A controlled experiment was conducted to assess the effect of CAR-encoding mRNA on the survival of CAR T cells produced from cells donated by two myeloma patients. Two lots of CAR T cells, each lot produced from cells from two myeloma patients and by use of an inventive mRNA construct comprising the nucleotide sequences of SEQ ID: 31, were compared to two corresponding lots of CAR T cells, each lot produced from cells from the same two myeloma patients but by use of the reference mRNA construct comprising the nucleotide sequences of SEQ ID: 29. Except as noted here, each lot of CAR T cells was produced substantially by the methods described in Example 1. Cells were cultured for 21 hours after mRNA electroporation, whereupon cells were harvested, and viability was assessed. Results were as follows:

|            |           | Viability (%) |
|------------|-----------|---------------|
| SEQ ID: 31 | Patient 1 | 90            |
|            | Patient 2 | 81            |
| SEQ ID: 29 | Patient 1 | 83            |
|            | Patient 2 | 67            |

The viability of CAR T cells of SEQ ID:29 was substantially lower than that of CAR T cells of SEQ ID:31. In conclusion, an inventive mRNA construct of SEQ ID:31 conferred better viability upon CAR T cells than a comparator mRNA construct of SEQ ID:29.

Example 12: Use of Sleeping Beauty Transposon System to Make Permanently Modified CAR T Cells Expressing an Inventive Chimeric Antigen Receptor The Sleeping Beauty transposon system was used to make permanently modified CAR T Cells that expressed an inventive Chimeric Antigen Receptor.

A first plasmid was constructed comprising the elements of an EF1a promoter, an IgG 5'UTR, an open reading frame encoding the amino acid sequence of SEQ ID:21, and a polyA tail, wherein the foregoing elements were collectively flanked by the Inverted Terminal Repeats of the Sleeping Beauty transposon (the "Seq-21 Transposon Plasmid"). A second plasmid was constructed comprising an EF1a promoter, an IgG 5'UTR, a Kozak consensus sequence, an open reading frame encoding SB11, and a polyA tail (the "SB11 plasmid")

Figure 3B:
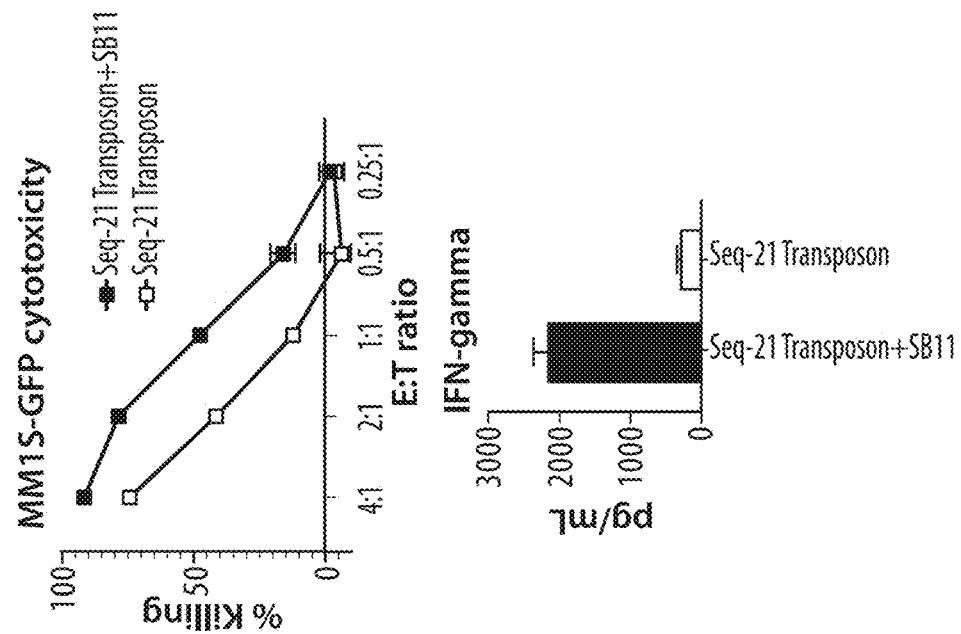
FIG. 3B shows anti-BCMA cytotoxicity and interferon-γ secretion by T cells that were modified by the Sleeping Beauty transposon system to express a CAR of SEQ ID: 31.
Figure 3A:
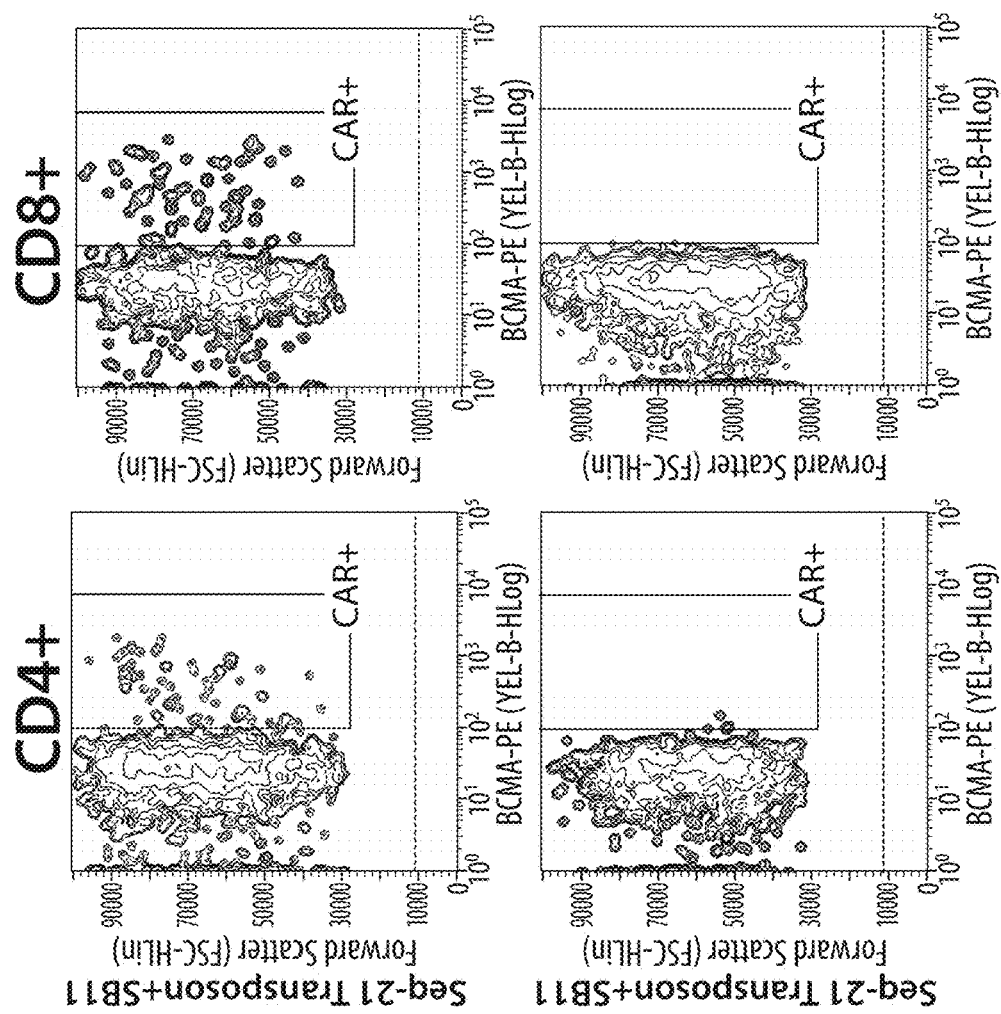
FIG. 3A shows measurements of CAR expression.

Peripheral Blood Mononuclear cells from a normal human donor were washed and resuspended in P3 buffer (Lonza) in the presence of Seq-21 Transposon plasmid alone or in the presence of both the Seq-21 Transposon plasmid and the SB11 plasmid. Cells were electroporated (4D Nucleofector®, Lonza) to introduce the plasmid(s) into cells. The cells were then transferred to culture for 5 hours. Cells were transferred to a stimulation culture comprising CD3/CD28 Dynabeads® (ThermoFisher). During expansion CD4+ and CD8+ T cells were analyzed for expression of the CAR by staining with BCMA-PE reagent and flow cytometry as described in Example 1. By day 14, T cells had expanded by 30-fold. Cells modified with both the SB11 and Seq-21 Transposon plasmids showed 5-10% of cells reactive for BCMA-PE (FIG. 3A). Cells expanded after transfection with the Seq-21 Transposon Plasmid alone showed no reactivity. Functional CAR T cell activity was evaluated using cytotoxicity assays with the multiple myeloma target cell line MM1S-GFP as described in Example 1 using multiple Effector:Target ratios using cell numbers based on total viable cells. Cytokine (interferon-γ) production was also evaluated on coculture supernatants from the 4:1 Effector:Target ratio by ELISA. FIG. 3B shows data from Day 9 cells illustrating specific cytotoxicity and interferon-γ production conferred by permanent modification with the anti-BCMA CAR delivered with the Seq-21 Transposon Plasmid and SB11 Plasmid, but not conferred by the Seq-21 Transposon Plasmid alone.

Thus, the Sleeping Beauty transposon system was successfully used to produce CAR T Cells that expressed an inventive anti-BCMA CAR. These cells demonstrated anti-BCMA cytotoxicity and cytokine secretion. They are expected to express the CAR permanently.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which two or more members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A chimeric antigen receptor (CAR) comprising:
   (i) an anti-B-Cell Maturation Antigen (BCMA) binding domain;
   (ii) a transmembrane domain; and
   (iii) a cytoplasmic domain,
   wherein the anti-BCMA binding domain comprises:
   a heavy chain complementarity determining region 1 (CDRH1) comprising any one of SEQ ID NOs: 1-3;
   a heavy chain complementarity determining region 2 (CDRH2) comprising any one of SEQ ID NOs: 4-6;
   a heavy chain complementarity determining region 3 (CDRH3) comprising any one of SEQ ID NOs: 7-9;
   a light chain complementarity determining region 1 (CDRL1) comprising any one of SEQ ID NOs: 10-11;
   a light chain complementarity determining region 2 (CDRL2) comprising any one of SEQ ID NOs: 12-15; and
   a light chain complementarity determining region 3 (CDRL3) comprising any one of SEQ ID NOs: 16-18;
   provided that the anti-BCMA binding domain does not comprise all six of the following:
   a CDRH1 comprising SEQ ID NO: 1;
   a CDHR2 comprising SEQ ID NO: 4;
   a CDHR3 comprising SEQ ID NO: 7;
   a CDRL1 comprising SEQ ID NO: 10;
   a CDRL2 comprising SEQ ID NO: 12; and
   a CDRL3 comprising SEQ ID NO: 16.

2. The CAR of claim 1, wherein the CDRH3 comprises SEQ ID NO: 7.

3. The CAR of claim 1, wherein the CDRH3 comprises SEQ ID NO: 8.

4. The CAR of claim 1, wherein the CDRH3 comprises SEQ ID NO: 9.

5. The CAR of claim 1, wherein the CDRL3 comprises SEQ ID NO: 16.

6. The CAR of claim 1, wherein the CDRL3 comprises SEQ ID NO: 17.

7. The CAR of claim 1, wherein the CDRL3 comprises SEQ ID NO: 18.

8. The CAR of claim 1, wherein:
   (i) the CDRH1 comprises SEQ ID NO: 3;
   (ii) the CDRH2 comprises SEQ ID NO: 4;
   (iii) the CDRH3 comprises SEQ ID NO: 7;
   (iv) the CDRL1 comprises SEQ ID NO: 10;
   (v) the CDRL2 comprises SEQ ID NO: 12; and
   (vi) the CDRL3 comprises SEQ ID NO: 16.

9. The CAR of claim 1, wherein:
   (i) the CDRH1 comprises SEQ ID NO: 1;
   (ii) the CDRH2 comprises SEQ ID NO: 4;
   (iii) the CDRH3 comprises SEQ ID NO: 8;
   (iv) the CDRL1 comprises SEQ ID NO: 10;
   (v) the CDRL2 comprises SEQ ID NO: 12; and
   (vi) the CDRL3 comprises SEQ ID NO: 16.

10. The CAR of claim 1, wherein:
    (i) the CDRH1 comprises SEQ ID NO: 1;
    (ii) the CDRH2 comprises SEQ ID NO: 4;
    (iii) the CDRH3 comprises SEQ ID NO: 7;
    (iv) the CDRL1 comprises SEQ ID NO: 11;
    (v) the CDRL2 comprises SEQ ID NO: 14; and
    (vi) the CDRL3 comprises SEQ ID NO: 17.

11. The CAR of claim 1, wherein:
    (i) the CDRH1 comprises SEQ ID NO: 1;
    (ii) the CDRH2 comprises SEQ ID NO: 4;
    (iii) the CDRH3 comprises SEQ ID NO: 7;
    (iv) the CDRL1 comprises SEQ ID NO: 11;
    (v) the CDRL2 comprises SEQ ID NO: 14; and
    (vi) the CDRL3 comprises SEQ ID NO: 18.

12. The CAR of claim 1, wherein:
    (i) the CDRH1 comprises SEQ ID NO: 2;
    (ii) the CDRH2 comprises SEQ ID NO: 6;
    (iii) the CDRH3 comprises SEQ ID NO: 9;
    (iv) the CDRL1 comprises SEQ ID NO: 10;
    (v) the CDRL2 comprises SEQ ID NO: 12; and
    (vi) the CDRL3 comprises SEQ ID NO: 16.

13. The CAR of claim 1, wherein:
(i) the CDRH1 comprises SEQ ID NO: 3;
(ii) the CDRH2 comprises SEQ ID NO: 5;
(iii) the CDRH3 comprises SEQ ID NO: 8;
(iv) the CDRL1 comprises SEQ ID NO: 10;
(v) the CDRL2 comprises SEQ ID NO: 12; and
(vi) the CDRL3 comprises SEQ ID NO: 16.
14. The CAR of claim 1, wherein:
(i) the CDRH1 comprises SEQ ID NO: 3;
(ii) the CDRH2 comprises SEQ ID NO: 4;
(iii) the CDRH3 comprises SEQ ID NO: 9;
(iv) the CDRL1 comprises SEQ ID NO: 10;
(v) the CDRL2 comprises SEQ ID NO: 12; and
(vi) the CDRL3 comprises SEQ ID NO: 18.
15. The CAR of claim 1, wherein:
(i) the CDRH1 comprises SEQ ID NO: 2;
(ii) the CDRH2 comprises SEQ ID NO: 6;
(iii) the CDRH3 comprises SEQ ID NO: 9;
(iv) the CDRL1 comprises SEQ ID NO: 11;
(v) the CDRL2 comprises SEQ ID NO: 13; and
(vi) the CDRL3 comprises SEQ ID NO: 17.
16. The CAR of claim 1, wherein:
(i) the CDRH1 comprises SEQ ID NO: 1;
(ii) the CDRH2 comprises SEQ ID NO: 4;
(iii) the CDRH3 comprises SEQ ID NO: 7;
(iv) the CDRL1 comprises SEQ ID NO: 10;
(v) the CDRL2 comprises SEQ ID NO: 15; and
(vi) the CDRL3 comprises SEQ ID NO: 16.
17. The CAR of claim 1, wherein:
(i) the CDRH1 comprises SEQ ID NO: 2;
(ii) the CDRH2 comprises SEQ ID NO: 6;
(iii) the CDRH3 comprises SEQ ID NO: 9;
(iv) the CDRL1 comprises SEQ ID NO: 11;
(v) the CDRL2 comprises SEQ ID NO: 14; and
(vi) the CDRL3 comprises SEQ ID NO: 17.

18. The CAR of claim 1, wherein:
(i) the CDRH1 comprises SEQ ID NO: 2;
(ii) the CDRH2 comprises SEQ ID NO: 6;
(iii) the CDRH3 comprises SEQ ID NO: 9;
(iv) the CDRL1 comprises SEQ ID NO: 11;
(v) the CDRL2 comprises SEQ ID NO: 14; and
(vi) the CDRL3 comprises SEQ ID NO: 18.
19. The CAR of claim 1, wherein the CDRH1 comprises SEQ ID NO: 1.
20. The CAR of claim 1, wherein the CDRH1 comprises SEQ ID NO: 2.
21. The CAR of claim 1, wherein the CDRH1 comprises SEQ ID NO: 3.
22. The CAR of claim 1, wherein the CDRH2 comprises SEQ ID NO: 4.
23. The CAR of claim 1, wherein the CDRH2 comprises SEQ ID NO: 5.
24. The CAR of claim 1, wherein the CDRH2 comprises SEQ ID NO: 6.
25. The CAR of claim 1, wherein the CDRL1 comprises SEQ ID NO: 10.
26. The CAR of claim 1, wherein the CDRL1 comprises SEQ ID NO: 11.
27. The CAR of claim 1, wherein the CDRL2 comprises SEQ ID NO: 12.
28. The CAR of claim 1, wherein the CDRL2 comprises SEQ ID NO: 13.
29. The CAR of claim 1, wherein the CDRL2 comprises SEQ ID NO: 14.
30. The CAR of claim 1, wherein the CDRL2 comprises SEQ ID NO: 15.

* * * * *